(12) United States Patent
Devlin et al.

(10) Patent No.: US 12,186,329 B2
(45) Date of Patent: Jan. 7, 2025

(54) COMPOSITIONS AND METHODS RELATED TO CHOLIC ACID 7-SULFATE AS A TREATMENT FOR DIABETES

(71) Applicants: President and Fellows of Harvard College, Cambridge, MA (US); The Brigham and Women's Hospital, Inc., Boston, MA (US)

(72) Inventors: Abigail Sloan Devlin, Cambridge, MA (US); Snehal N. Chaudhari, Cambridge, MA (US); Eric Garland Sheu, Brookline, MA (US); David A. Harris, Arlington, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 865 days.

(21) Appl. No.: 17/270,201

(22) PCT Filed: Aug. 23, 2019

(86) PCT No.: PCT/US2019/047856
§ 371 (c)(1),
(2) Date: Feb. 22, 2021

(87) PCT Pub. No.: WO2020/041673
PCT Pub. Date: Feb. 27, 2020

(65) Prior Publication Data
US 2021/0315908 A1 Oct. 14, 2021

Related U.S. Application Data

(60) Provisional application No. 62/722,010, filed on Aug. 23, 2018.

(51) Int. Cl.
| | | |
|---|---|---|
| A61K 31/575 | (2006.01) | |
| A61K 45/06 | (2006.01) | |
| A61P 3/00 | (2006.01) | |
| A61P 3/04 | (2006.01) | |
| A61P 3/10 | (2006.01) | |
| A61P 37/02 | (2006.01) | |

(52) U.S. Cl.
CPC ............ *A61K 31/575* (2013.01); *A61K 45/06* (2013.01); *A61P 3/00* (2018.01); *A61P 3/04* (2018.01); *A61P 3/10* (2018.01); *A61P 37/02* (2018.01)

(58) Field of Classification Search
CPC .... A61K 31/575; A61K 45/06; A61K 31/155; A61K 31/198; A61K 31/4439; A61K 31/4985; A61K 38/28; A61P 3/10; A61P 3/00; A61P 3/04; A61P 37/02; A61P 5/48; A61P 5/50
See application file for complete search history.

(56) References Cited

U.S. PATENT DOCUMENTS

| | | |
|---|---|---|
| 5,210,272 A | 5/1993 | Palmer |
| 5,695,738 A | 12/1997 | Anderson et al. |
| 5,733,566 A | 3/1998 | Lewis |
| 6,451,355 B1 | 9/2002 | Reisner et al. |
| 9,345,715 B2 | 5/2016 | Young et al. |
| 9,580,459 B2 | 2/2017 | Dosa et al. |
| 2007/0032464 A1 | 2/2007 | Liao et al. |
| 2009/0118306 A1 | 5/2009 | Husson et al. |
| 2010/0130426 A1 | 5/2010 | Yung et al. |
| 2011/0059932 A1 | 3/2011 | Peng et al. |
| 2012/0277198 A1 | 11/2012 | Ling et al. |
| 2014/0323748 A1 | 1/2014 | Dosa et al. |
| 2014/0206657 A1 | 7/2014 | Yu et al. |
| 2014/0234256 A1 | 8/2014 | March et al. |
| 2016/0184266 A9 | 6/2016 | Szewczyk |
| 2018/0319836 A1 | 11/2018 | Yu et al. |
| 2018/0340006 A1 | 11/2018 | Weymouth-Wilson et al. |
| 2022/0016138 A1 | 1/2022 | Devlin et al. |
| 2022/0204548 A1 | 6/2022 | Devlin et al. |
| 2023/0174988 A1 | 6/2023 | Devlin et al. |

FOREIGN PATENT DOCUMENTS

| | | |
|---|---|---|
| CN | 106478759 A | 3/2017 |
| DE | 19941764 A1 | 3/2001 |
| EP | 0117570 A1 | 9/1986 |
| EP | 548793 A2 | 6/1993 |
| EP | 624593 A2 | 11/1994 |
| EP | 2221313 A1 | 8/2010 |
| RU | 2665685 C1 | 9/2018 |

(Continued)

OTHER PUBLICATIONS

Skyler et al, Differentiation of Diabetes by Pathophysiology, Natural History, and Prognosis,(Feb. 2017), Diabetes, 66, 241-255 (Year: 2017).*
U.S. Appl. No. 17/610,037, filed Nov. 9, 2021, Devlin et al.
U.S. Appl. No. 17/923,891, filed Nov. 7, 2022, Devlin et al.
EP 20805532.7, Jan. 5, 2023, Extended European Search Report.
PCT/US2020/032016, Nov. 25, 2021, International Preliminary Report on Patentability.
EP 19892790.7, Aug. 18, 2022, Extended European Search Report.
PCT/US2021/031277, Aug. 11, 2021, Invitation to Pay Additional Fees.
PCT/US2021/031277, Oct. 14, 2021, International Search Report and Written Opinion.
PCT/US2021/031277, Nov. 17, 2022, International Preliminary Report on Patentability.

(Continued)

*Primary Examiner* — Juliet C Switzer
*Assistant Examiner* — Dawanna Shar-Day White
(74) *Attorney, Agent, or Firm* — Wolf, Greenfield & Sacks, P.C.

(57) ABSTRACT

Provided are methods of treating diabetes and/or obesity in a subject in need thereof, and methods of increasing the amount of cholic acid-7-sulfate (CA7S) in a subject. Further provided herein are methods of administering CA7S to a subject. Also provided are compositions and kits comprising cholic acid-7-sulfate, or a salt thereof for use in the treatment of diabetes and/or obesity.

20 Claims, 26 Drawing Sheets
Specification includes a Sequence Listing.

(56) References Cited

FOREIGN PATENT DOCUMENTS

| TW | 201700447 A | 1/2017 | | |
|---|---|---|---|---|
| WO | WO 94/00126 A1 | 1/1994 | | |
| WO | WO 95/07089 A1 | 3/1995 | | |
| WO | WO 97/18816 A1 | 5/1997 | | |
| WO | WO 98/52585 A1 | 11/1998 | | |
| WO | WO 2000/024761 A1 | 5/2000 | | |
| WO | WO 2000/066611 A1 | 11/2000 | | |
| WO | WO 2001/021642 A1 | 3/2001 | | |
| WO | WO 2003/066657 A1 | 8/2003 | | |
| WO | WO 2004/092193 A1 | 10/2004 | | |
| WO | WO 2011/022838 A1 | 3/2011 | | |
| WO | WO 2013/096771 A1 | 6/2013 | | |
| WO | WO 2013/113680 A1 | 8/2013 | | |
| WO | WO 2016/100619 A2 | 6/2016 | | |
| WO | WO-2016205475 A2 * | 12/2016 | ................ | A61P 1/16 |
| WO | WO 2017/035501 A1 | 3/2017 | | |
| WO | WO 2017/106818 A1 | 6/2017 | | |
| WO | WO 2017/142895 A1 | 8/2017 | | |
| WO | WO 2019/075365 A1 | 4/2019 | | |
| WO | WO 2019/191637 A1 | 10/2019 | | |
| WO | WO 2020/041673 A1 | 2/2020 | | |
| WO | WO 2020/117945 A1 | 6/2020 | | |

OTHER PUBLICATIONS

Extended European Search Report for Application No. 20805532.7, mailed Jan. 5, 2023.
International Preliminary Report on Patentability for Application No. PCT/US2020/032016, mailed Nov. 25, 2021.
Extended European Search Report for Application No. 19892790.7, mailed Aug. 18, 2022.
Invitation to Pay Additional Fees for Application No. PCT/US2021/031277, mailed Aug. 11, 2021.
International Search Report and Written Opinion for Application No. PCT/US2021/031277, mailed Oct. 14, 2021.
International Preliminary Report on Patentability for Application No. PCT/US2021/031277, mailed Nov. 17, 2022.
Adhikari et al., Development of a covalent inhibitor of gut bacterial bile salt hydrolases. Nat Chem Biol. Mar. 2020;16(3):318-326. doi: 10.1038/s41589-020-0467-3. Epub Feb. 10, 2020.
Adhikari et al., Development of a covalent inhibitor of gut bacterial bile salt hydrolases. bioRxiv. May 17, 2019. URL: https://www.biorxiv.org/content/10.1101/640086v1.full/ [retrieved from the internet: Dec. 14, 2022].
D'Amore et al., Design, synthesis, and biological evaluation of potent dual agonists of nuclear and membrane bile acid receptors. J Med Chem. Feb. 13, 2014;57(3):937-54. doi: 10.1021/jm401873d. Epub Jan. 17, 2014.
Fader et al., 2,3,7,8-Tetrachlorodibenzo-p-dioxin (TCDD)-elicited effects on bile acid homeostasis: Alterations in biosynthesis, enterohepatic circulation, and microbial metabolism. Sci Rep. Jul. 19, 2017;7(1):5921. doi: 10.1038/s41598-017-05656-8.
Ferrell et al., Understanding Bile Acid Signaling in Diabetes: From Pathophysiology to Therapeutic Targets. Diabetes Metab J. Jun. 2019;43(3):257-272. doi: 10.4093/dmj.2019.0043.
Festa et al., Exploitation of cholane scaffold for the discovery of potent and selective farnesoid X receptor (FXR) and G-protein coupled bile acid receptor 1 (GP-BAR1) ligands. J Med Chem. Oct. 23, 2014;57(20):8477-95. doi: 10.1021/jm501273r. Epub Oct. 9, 2014.
Fried et al., The synthesis of diazo, halo, and sulfoxy bile acid derivatives: potential affinity labels. Steroids. Aug. 1979;34(2):171-87. doi: 10.1016/0039-128x(79)90046-1.
Ishihara et al., Uber Den Systematischen Abbau Der Chenodeoxycholsaure. Journal of Biochemistry. 1938; 27(2):265-277. DOI: 10.1093/oxfordjournals.jbchem.a125715.
Lööf, Enzymatic sulphation of bile salts in man. Bile salt sulphotransferase activity in human adrenal. Digestion. 1981;21(6):297-303. doi: 10.1159/000198580.
Nakhi et al., 7-Methylation of Chenodeoxycholic Acid Derivatives Yields a Substantial Increase in TGR5 Receptor Potency. J Med Chem. Jul. 25, 2019;62(14):6824-6830. doi: 10.1021/acs.jmedchem.9b00770. Epub Jul. 3, 2019.
Rearick et al., Increase in cholesterol sulfotransferase activity during in vitro squamous differentiation of rabbit tracheal epithelial cells and its inhibition by retinoic acid. J Biol Chem. Sep. 25, 1987;262(27):13069-74.
Sepe et al., Modification on ursodeoxycholic acid (UDCA) scaffold. discovery of bile acid derivatives as selective agonists of cell-surface G-protein coupled bile acid receptor 1 (GP-BAR1). J Med Chem. Sep. 25, 2014;57(18):7687-701. doi: 10.1021/jm500889f. Epub Sep. 7, 2014.
Wu et al., Vitamin D receptor negatively regulates bacterial-stimulated NF-kappaB activity in intestine. Am J Pathol. Aug. 2010;177(2):686-97. doi: 10.2353/ajpath.2010.090998. Epub Jun. 21, 2010.
International Search Report and Written Opinion for Application No. PCT/US2019/047856, mailed Dec. 10, 2019.
International Preliminary Report on Patentability for Application No. PCT/US2019/047856, mailed Mar. 4, 2021.
Invitation to Pay Additional Fees for Application No. PCT/US2020/032016, mailed Jul. 16, 2020.
International Search Report and Written Opinion for Application No. PCT/US2020/032016, mailed Sep. 22, 2020.
International Search Report and Written Opinion for Application No. PCT/US2019/064488, mailed Apr. 9, 2020.
International Preliminary Report on Patentability for Application No. PCT/US2019/064488, mailed Jun. 17, 2021.
Genbank Submission. NCBI; Accession No. ABC26911, version ABC26911.1. bile salt hydrolase [Bifidobacterium breve DSM 20213 = JCM 1192]. Goswami et al.; Dec. 19, 2005.
Genbank Submission. NCBI; Accession No. ABC26910, version ABC26910.1. bile salt hydrolase [Bifidobacterium bifidum]. Goswami et al.; Dec. 19, 2005.
Genbank Submission. NCBI; Accession No. ACL98203, version ACL98203.1; bile salt hydrolase (plasmid) [Ligilactobacillus salivarius]. Fang et al.; Jul. 24, 2016.
Genbank Submission. NCBI; Accession No. AAS98803, version AAS98803.1; bile salt hydrolase [Bifidobacterium animalis]. Kim et al.; Aug. 25, 2008.
Genbank Submission. NCBI; Accession No. AKI55714, version AKI55714.1; bile salt hydrolase [Listeria monocytogenes]. Bergholz et al.; Jun. 3, 2015.
Genbank Submission. NCBI; Accession No. Accession: AAP20760, version AAP20760.1; bile salt hydrolase [Enterococcus faecium]. Wijaya et al.; Apr. 28, 2003.
Genbank Submission. NCBI; Accession No. Accession: NM_006143, version NM_006143.2; Homo sapiens G protein-coupled receptor 19 (GPR19), mRNA. Rao et al.; Nov. 11, 2018.
Genbank Submission. NCBI; Accession No. Accession: NP_006134, version NP_006134.1; probable G-protein coupled receptor 19 [Homo sapiens]. Yang et al.; Nov. 11, 2018.
Genbank Submission. NCBI; Accession No. Accession: NG_008731, version NG_008731.1; Homo sapiens vitamin D receptor (VDR), RefSeqGene on chromosome 12. Loughran et al.; Feb. 15, 2021.
Genbank Submission. NCBI; Accession No. Accession: NP_001017535, version NP_001017535.1; vitamin D3 receptor isoform VDRA [Homo sapiens]. Moosavi et al.; Apr. 19, 2021.
Genbank Submission. NCBI; Accession No. Accession: NP_001017536, version NP_001017536.1; vitamin D3 receptor isoform VDRB1 [Homo sapiens]. Moosavi et al.; Apr. 18, 2021.
Genbank Submission. NCBI; Accession No. Accession: NM_000376, version NM_000376.2; Homo sapiens vitamin D receptor (VDR), transcript variant 1, mRNA. Kirac et al.; May 28, 2019.
Genbank Submission. NCBI; Accession No. Accession: NG_016745, version NG_016745.1; Homo sapiens sulfotransferase family 2A member 1 (SULT2A1), RefSeqGene on chromosome 19. No Author Listed; Dec. 14, 2020.
Genbank Submission. NCBI; Accession No. Accession: NP_003158, version NP_003158.2; sulfotransferase 2A1 [Homo sapiens]. Luck et al.; Apr. 15, 2021.

(56) References Cited

OTHER PUBLICATIONS

Genbank Submission. NCBI; Accession No. Accession: NM_003167, version NM_003167.4; Homo sapiens sulfotransferase family 2A member 1 (SULT2A1), mRNA. Luck et al.; Apr. 15, 2021.
[No Author Listed] Chemical Abstracts STN Database Record for RN 1240039-42-2. Entered Sep. 7, 2020. 4 pages.
[No Author Listed], Pubchem Compound for CID 129820655. Sep. 13, 2017. 9 pages.
[No Author Listed], Pubchem Compound for CID 126738689. Apr. 22, 2017. 8 pages.
[No Author Listed], Supplementary Information. Harvard University. Dec. 2019. 62 pages.
Abbasi, Unveiling the "Magic" of Diabetes Remission After Weight-Loss Surgery. JAMA. Feb. 14, 2017;317(6):571-574. doi: 10.1001/jama.2017.0020.
Adachi et al., Selective activation of vitamin D receptor by lithocholic acid acetate, a bile acid derivative. J Lipid Res. Jan. 2005;46(1):46-57. doi: 10.1194/jlr.M400294-JLR200. Epub Oct. 16, 2004.
Afonine et al., Towards automated crystallographic structure refinement with phenix.refine. Acta Crystallogr D Biol Crystallogr. Apr. 2012;68(Pt 4):352-67. doi: 10.1107/S0907444912001308. Epub Mar. 16, 2012.
Alexander et al., multiplierz v2.0: A Python-based ecosystem for shared access and analysis of native mass spectrometry data. Proteomics. Aug. 2017;17(15-16). doi: 10.1002/pmic.201700091.
Alnouti, Bile Acid sulfation: a pathway of bile acid elimination and detoxification. Toxicol Sci. Apr. 2009;108(2):225-46. doi: 10.1093/toxsci/kfn268. Epub Jan. 8, 2009.
Angliker et al., The Synthesis of Lysylfluoromethanes and Their Properties as Inhibitors of Trypsin, Plasmin and Cathepsin B. Biochem. J. 1987; 241(3): 871-875.
Assimakopoulos et al., Altered intestinal tight junctions' expression in patients with liver cirrhosis: a pathogenetic mechanism of intestinal hyperpermeability. Eur J Clin Invest. Apr. 2012;42(4):439-46. doi: 10.1111/j.1365-2362.2011.02609.x. Epub Oct. 24, 2011.
Atarashi et al., Treg Induction by a Rationally Selected Mixture of Clostridia Strains From the Human Microbiota. Nature. Aug. 8, 2013; 500 (7461): 232-236.
Baba et al., Selective activity of several cholic acid derivatives against human immunodeficiency virus replication in vitro. J Acquir Immune Defic Syndr (1988). 1989;2(3):264-71.
Bäckhed et al., Mechanisms Underlying the Resistance to Diet-Induced Obesity in Germ-Free Mice. PNAS. 2007; 104(3):979-84.
Bandiera et al., A convenient procedure for the synthesis of ursodeoxycholic acid sulfated derivatives. Synthetic Communications. 1987; 17(9): 1111-17.
Barnes et al., Renal mechanisms influencing the bile acid composition of cholestatic urine. Bile Acid Metab. Health Dis., Proc. Bile Acid Meeting. 1977; 89-92.
Barnes et al., The role of tubular reabsorption in the renal excretion of bile acids. Biochem J. Jul. 15, 1977;166(1):65-73. doi: 10.1042/bj1660065.
Batterham et al., Mechanisms of Diabetes Improvement Following Bariatric/Metabolic Surgery. Diabetes Care. Jun. 2016;39(6):893-901. doi: 10.2337/dc16-0145.
Begley et al., Bile Salt Hydrolase Activity in Probiotics. Appl. Environ. Microbiol. 2006; 72(3): 1729-1738.
Bernier-Latmani et al., Intestinal lymphatic vasculature: structure, mechanisms and functions. Nat Rev Gastroenterol Hepatol. Sep. 2017;14(9):510-526. doi: 10.1038/nrgastro.2017.79. Epub Jun. 28, 2017.
Besnard et al., Is the ileal bile acid-binding protein (I-BABP) gene involved in cholesterol homeostasis ?. Med Sci (Paris). Jan. 2004;20(1):73-7. doi: 10.1051/medsci/200420173.
Bhutta et al., Effect of Roux-en-Y gastric bypass surgery on bile acid metabolism in normal and obese diabetic rats. PLoS One. Mar. 23, 2015;10(3):e0122273. doi: 10.1371/journal.pone.0122273. eCollection 2015.
Blosser et al., A method to assess target gene involvement in angiogenesis in vitro and in vivo using lentiviral vectors expressing shRNA. PLoS One. Apr. 23, 2014;9(4):e96036. doi: 10.1371/journal.pone.0096036. eCollection 2014.
Brighton et al., Bile Acids Trigger GLP-1 Release Predominantly by Accessing Basolaterally Located G Protein-Coupled Bile Acid Receptors. Endocrinology. Nov. 2015;156(11):3961-70. doi: 10.1210/en.2015-1321. Epub Aug. 17, 2015.
Bureeva et al., Selective inhibition of the interaction of C1q with immunoglobulins and the classical pathway of complement activation by steroids and triterpenoids sulfates. Bioorg Med Chem. May 15, 2007;15(10):3489-98. doi: 10.1016/j.bmc.2007.03.002. Epub Mar. 6, 2007.
Callahan et al., DADA2: High-resolution sample inference from Illumina amplicon data. Nat Methods. Jul. 2016;13(7):581-3. doi: 10.1038/nmeth.3869. Epub May 23, 2016.
Cao et al., Intestinally-targeted TGR5 agonists equipped with quaternary ammonium have an improved hypoglycemic effect and reduced gallbladder filling effect. Sci Rep. Jun. 24, 2016;6:28676. doi: 10.1038/srep28676.
Cao et al., Liposomes Coated with Isolated Macrophage Membrane Can Target Lung Metastasis of Breast Cancer. ACS Nano. Aug. 23, 2016;10(8):7738-48. doi: 10.1021/acsnano.6b03148. Epub Jul. 27, 2016.
Caporaso et al., QIIME allows analysis of high-throughput community sequencing data. Nat Methods. May 2010;7(5):335-6. doi: 10.1038/nmeth.f.303. Epub Apr. 11, 2010.
Castro-Perez et al., Attenuation of Slc27a5 gene expression followed by LC-MS measurement of bile acid reconjugation using metabolomics and a stable isotope tracer strategy. J Proteome Res. Oct. 7, 2011;10(10):4683-91. doi: 10.1021/pr200475g. Epub Aug. 26, 2011.
Chand et al., Structure and Function of a Highly Active Bile Salt Hydrolase (BSH) From Enterococcus Faecalis and Post-Translational Processing of BSH Enzymes. Biochim Biophys Acta Proteins Proteom. 2018; 1866(4): 507-518.
Chaudhari et al., A microbial metabolite remodels the gut-liver axis following bariatric surgery. Cell Host Microbe. Mar. 10, 2021;29(3):408-424.e7. doi: 10.1016/j.chom.2020.12.004. Epub Jan. 11, 2021.
Chaudhari et al., Bariatric surgery reveals a gut-restricted TGR5 agonist with anti-diabetic effects. Nat Chem Biol. Jan. 2021;17(1):20-29. doi: 10.1038/s41589-020-0604-z. Epub Aug. 3, 2020.
Chen et al., Design of Gut-Restricted Thiazolidine Agonists of G Protein-Coupled Bile Acid Receptor 1 (GPBAR1, TGR5). J Med Chem. Sep. 13, 2018;61(17):7589-7613. doi: 10.1021/acs.jmedchem.8b00308. Epub Aug. 24, 2018.
Chen et al., MolProbity: all-atom structure validation for macromolecular crystallography. Acta Crystallogr D Biol Crystallogr. Jan. 2010;66(Pt 1):12-21. doi: 10.1107/S0907444909042073. Epub Dec. 21, 2009.
Chiang, Recent Advances in Understanding Bile Acid Homeostasis. F1000Res. Nov. 20, 2017;6:2029. doi: 10.12688/f1000research.12449.1. eCollection 2017.
Cohen et al., Differing effects of nor-ursodeoxycholic or ursodeoxycholic acid on hepatic histology and bile acid metabolism in the rabbit. Gastroenterology. Jul. 1986;91(1):189-97. doi: 10.1016/0016-5085(86)90457-9.
Cohen et al., Solvolysis of chenodeoxycholic acid sulfates. Steroids. Jun. 1981;37(6):621-6. doi: 10.1016/s0039-128x(81)90149-5.
Cohen et al., Structural Bioinformatics-Based Design of Selective, Irreversible Kinase Inhibitors. Science. 2005; 308(5726):1318-1321.
Coleman et al., Cloning and Characterization of a Conjugated Bile Acid Hydrolase Gene From Clostridium Perfringens. Appl Environ Microbiol. 1995; 61(7): 2514-2520.
Compher et al., Vitamin D and the bariatric surgical patient: a review. Obes Surg. Feb. 2008;18(2):220-4. doi: 10.1007/s11695-007-9289-6. Epub Jan. 5, 2008.
Craddock et al., Expression and transport properties of the human ileal and renal sodiumdependent bile acid transporter. Am J Physiol. Jan. 1998;274(1):G157-69. doi: 10.1152/ajpgi.1998.274.1.G157.
Cross et al., The Isothiocyanate Class of Bioactive Nutrients Covalently Inhibit the MEKK1 Protein Kinase. BMC Cancer. 2007; 7(1): 183.

(56) References Cited

OTHER PUBLICATIONS

Czygan et al., Synthesis and excretion of bile acid sulfate esters in the isolated perfused rat kidney. Bile Acid Metab. Health Dis., Proc. Bile Acid Meet., 4th (1977), Meeting Date 1976, 83-7.

Dawson et al., Targeted deletion of the ileal bile acid transporter eliminates enterohepatic cycling of bile acids in mice. J Biol Chem. Sep. 5, 2003;278(36):33920-7. doi: 10.1074/jbc.M306370200. Epub Jun. 20, 2003.

Dawson, Roles of Ileal ASBT and OSTalpha-OSTbeta in Regulating Bile Acid Signaling. Dig Dis. 2017;35(3):261-266. doi: 10.1159/000450987. Epub Mar. 1, 2017.

De Witt et al., Effects of sulfation patterns on intestinal transport of bile salt sulfate esters. Am J Physiol. Jan. 1980;238(1):G34-9. doi: 10.1152/ajpgi.1980.238.1.G34.

Devlin, Gut Bacterial Modification of Bile Acids Alters Host Physiology. Harvard Chan Microbiome in Public Health Center Symposium. May 8, 2020. 55 pages.

Diaz et al., Normal Gut Microbiota Modulates Brain Development and Behavior. Proc. Natl. Acad. Sci. U.S.A. 2011; 108(7):3047-3052.

Ding et al., Vertical sleeve gastrectomy activates GPBAR-1/TGR5 to sustain weight loss, improve fatty liver, and remit insulin resistance in mice. Hepatology. Sep. 2016;64(3):760-73. doi: 10.1002/hep.28689. Epub Jul. 25, 2016.

Disibio et al., Metastatic patterns of cancers: results from a large autopsy study. Arch Pathol Lab Med. Jun. 2008; 132(6):931-9. doi: 10.5858/2008-132-931-MPOCRF.

Dong et al., Bile Salt Hydrolases: Structure and Function, Substrate Preference, and Inhibitor Development. Protein Sci. 2018; 27(10): 1742-1754.

Donia et al., Human Microbiota. Small Molecules From the Human Microbiota. Science. 2015; 349(6246): 1254766.

Dosa et al., Synthesis and evaluation of water-soluble prodrugs of ursodeoxycholic acid (UDCA), an anti-apoptotic bile acid. ChemMedChem. Jun. 2013;8(6):1002-11. doi: 10.1002/cmdc.201300059. Epub May 2, 2013.

Duboc et al., The bile acid TGR5 membrane receptor: from basic research to clinical application. Dig Liver Dis. Apr. 2014;46(4):302-12. doi: 10.1016/j.dld.2013.10.021. Epub Jan. 9, 2014.

Eissele et al., Glucagon-like peptide-1 cells in the gastrointestinal tract and pancreas of rat, pig and man. Eur J Clin Invest. Apr. 1992;22(4):283-91. doi: 10.1111/j.1365-2362.1992.tb01464.x.

Eriksson et al., Occurrence of sulfated 5alpha-cholanoates in rat bile. J Lipid Res. Feb. 1978;19(2):177-86.

Eyssen et al., Sulfate bile acids in germ-free and conventional mice. Eur J Biochem. Jul. 15, 1976;66(3):507-14. doi: 10.1111/j.1432-1033.1976.tb10576.x.

Ferruzza et al., A protocol for differentiation of human intestinal Caco-2 cells in asymmetric serum-containing medium. Toxicol In Vitro. Dec. 2012;26(8):1252-5. doi: 10.1016/j.tiv.2012.01.008. Epub Jan. 15, 2012.

Ficarro et al., Improved electrospray ionization efficiency compensates for diminished chromatographic resolution and enables proteomics analysis of tyrosine signaling in embryonic stem cells. Anal Chem. May 1, 2009;81(9):3440-7. doi: 10.1021/ac802720e.

Ficarro et al., mzStudio: A Dynamic Digital Canvas for User-Driven Interrogation of Mass Spectrometry Data. Proteomes. Aug. 1, 2017;5(3):20. doi: 10.3390/proteomes5030020.

Fiorucci et al., Bile Acid-Activated Receptors, Intestinal Microbiota, and the Treatment of Metabolic Disorders. Trends Mol Med. 2015; 21(11): 702-714.

Frank et al., Molecular-Phylogenetic Characterization of Microbial Community Imbalances in Human Inflammatory Bowel Diseases. PNAS. 2007; 104 (34):13780-13785.

Franzone et al., [Pharmacokinetics and hepatic metabolism of ursulcholic acid (a soluble form of ursodeoxycholic acid in the rat]. Boll Chim Farm. Jul. 1987;126(7):289-93.

Franzone et al., [The pharmacologic activity of ursulcholic acid, a soluble form of ursodeoxycholic acid]. Boll Chim Farm. Jul. 1987;126(7):282-8.

Fukui, Gut-liver axis in liver cirrhosis: How to manage leaky gut and endotoxemia. World J Hepatol. Mar. 27, 2015;7(3):425-42. doi: 10.4254/wjh.v7.i3.425.

Garland et al., Covalent Modifiers of Botulinum Neurotoxin Counteract Toxin Persistence. ACS Chem Biol. 2019; 14(1): 76-87.

Gartner et al., Transport of chenodeoxycholic acid and its 3-alpha- and 7-alpha-sulfates by isolated perfused rat liver. Hepatology. Oct. 1990; 12(4 Pt 1):738-42. doi: 10.1002/hep.1840120419.
Gehringer et al., Emerging and Re-Emerging Warheads for Targeted Covalent Inhibitors: Applications in Medicinal Chemistry and Chemical Biology. J Med Chem. 2019; 62:5673-5724.
Gehringer et al., Solution-Phase Parallel Synthesis of Ruxolitinib-Derived Janus Kinase Inhibitors via Copper-Catalyzed Azide-Alkyne Cycloaddition. ACS Comb Sci. 2015; 17(1): 5-10.
Ghosh et al., c-Fos mediates repression of the apical sodium-dependent bile acid transporter by fibroblast growth factor-19 in mice. Am J Physiol Gastrointest Liver Physiol. Jan. 2014;306(2):G163-71. doi: 10.1152/ajpgi.00276.2013. Epub Dec. 5, 2013.
Gloy et al., Bariatric surgery versus non-surgical treatment for obesity: a systematic review and meta-analysis of randomised controlled trials. BMJ. Oct. 22, 2013;347:f5934. doi: 10.1136/bmj.f5934.
Gonzalez et al., Putative irreversible inhibitors of the human sodium-dependent bile acid transporter (hASBT; SLC10A2) support the role of transmembrane domain 7 in substrate binding/translocation. Pharm Res. Jul. 2012;29(7):1821-31. doi: 10.1007/s11095-012-0706-8. Epub Feb. 22, 2012.
Goto et al., Separation of monosulfated bile acids by high-performance liquid chromatography. J Chromatogr. 1980;3(5): 645-55.
Goto et al., Studies on steroids. Part CCXXXII. Synthesis of disulfates of unconjugated and conjugated bile acids. Chem Pharm Bull (Tokyo). Nov. 1987;35(11):4562-7. doi: 10.1248/cpb.35.4562.
Goto et al., Studies on steroids. CCXXVII. Separation and determination of bile acid 7- and 12-sulphates in urine by high-performance liquid chromatography with fluorescence labelling. J Chromatogr. Mar. 20, 1987;415(1):45-52.
Goto et al., Studies on steroids. CCXXXIII. Separation and characterization of bile acid disulphates in human urine by high-performance liquid chromatography. J Chromatogr. Mar. 4, 1988;425(1):59-66. doi: 10.1016/0378-4347(88)80006-9.
Goto et al., Studies on steroids. CLXIII. Synthesis of monosulfates of cholic acid derivatives. Chem Pharm Bull. 1980; 28(11):3389-94.
Goto et al., Studies on steroids. CLXX. Separation and determination of bile acid 3-sulfates in human bile by high-performance liquid chromatography. J Chromatogr. Nov. 13, 1981;226(1):13-24.
Goto et al., Synthesis of monosulfates of unconjugated and conjugated bile acids. Chem Pharm Bull (Tokyo). Jun. 1979;27(6):1402-11. doi: 10.1248/cpb.27.1402.
Goto, [Chromatographic determination of bile acids in biological fluids with sensitive and selective detection]. Yakugaku Zasshi. Nov. 1990;110(11):807-21. doi: 10.1248/yakushi1947.110.11_807.
Goudarzi et al., An Integrated Multi-Omic Approach to Assess Radiation Injury on the Host-Microbiome Axis. Radiat Res. Sep. 2016;186(3):219-34. doi: 10.1667/RR14306.1. Epub Aug. 11, 2016.
Griffiths et al., Charge-remote fragmentation of sulfated and glucuronidated bile acids and their 2-aminoethanesulfonic acid derivatives. Rapid Commun Mass Spectrom. 1994; 8(3): 227-36.
Hamilton et al., Human Cecal Bile Acids: Concentration and Spectrum. Am. J. Physiol. Gastrointest. Liver Physiol. 2007; 293(1): G256-G263.
Harach et al., TGR5 potentiates GLP-1 secretion in response to anionic exchange resins. Sci Rep. 2012;2:430. doi: 10.1038/srep00430. Epub May 30, 2012.
Hasegawa et al., Effect of ursodeoxycholate-3,7-disulfate on biliary excretion of lithocholate-3-O-glucuronide in Eisai hyperbilirubinemic rat (EHBR). Hepatol Res. Aug. 2002;23(4):296-300. doi: 10.1016/s1386-6346(01)00188-7.
He et al., Gut microbiota as a potential target of metabolic syndrome: the role of probiotics and prebiotics. Cell Biosci. Oct. 25, 2017;7:54. doi: 10.1186/s13578-017-0183-1. eCollection 2017.
Henise et al., Irreversible Nek2 Kinase Inhibitors with Cellular Activity. Journal of Medicinal Chemistry. 2011; 54(12):4133-4146.

(56) References Cited

OTHER PUBLICATIONS

Hodge et al., Therapeutic potential of Takeda-G-protein-receptor-5 (TGR5) agonists. Hope or hype? Diabetes Obes Metab. May 2016;18(5):439-43. doi: 10.1111/dom.12636. Epub Mar. 17, 2016.
Hofmann, The Function of Bile Salts in Fat Absorption. the Solvent Properties of Dilute Micellar Solutions of Conjugated Bile Acids. Biochem J. 1963; 89(1): 57-68.
Huijghebaert et al., Influence of the Amino Acid Moiety on Deconjugation of Bile Acid Amidates by Cholylglycine Hydrolase or Human Fecal Cultures. J Lipid Res. 1986; 27(7): 742-752.
Huijghebaert et al., Specificity of bile salt sulfatase activity from *Clostridium* sp. strains S1. Appl Environ Microbiol. Nov. 1982;44(5):1030-4. doi: 10.1128/AEM.44.5.1030-1034.1982.
Iguchi et al., Effects of chemical modification of ursodeoxycholic acid on TGR5 activation. Biol Pharm Bull. 2011;34(1):1-7. doi: 10.1248/bpb.34.1.
Ivanov et al., Induction of Intestinal Th17 Cells by Segmented Filamentous Bacteria. Cell. 2009; 139(3): 485-98.
Jacobs et al., A Disease-Associated Microbial and Metabolomics State in Relatives of Pediatric Inflammatory Bowel Disease Patients. Cell Mol Gastroenterol Hepatol. Jul. 2, 2016;2(6):750-766. doi: 10.1016/j.jcmgh.2016.06.004. eCollection Nov. 2016.
Jahansouz et al., Antibiotic-induced Disruption of Intestinal Microbiota Contributes to Failure of Vertical Sleeve Gastrectomy. Ann Surg. Jun. 2019;269(6):1092-1100. doi: 10.1097/SLA.0000000000002729.
Jarocki et al., A New Insight into the Physiological Role of Bile Salt Hydrolase among Intestinal Bacteria from the Genus Bifidobacterium. PLoS One. Dec. 3, 2014;9(12):e114379. doi: 10.1371/journal.pone. 0114379. eCollection 2014.
Joyce et al., Bacterial bile salt hydrolase in host metabolism: Potential for influencing gastrointestinal microbe-host crosstalk. Gut Microbes. 2014;5(5):669-74. doi: 10.4161/19490976.2014. 969986.
Joyce et al., Regulation of Host Weight Gain and Lipid Metabolism by Bacterial Bile Acid Modification in the Gut. Proc. Natl. Acad. Sci. U.S.A. 2014; 111(20): 7421-7426.
Kakizaki et al., Xenobiotic-sensing nuclear receptors CAR and PXR as drug targets in cholestatic liver disease. Curr Drug Targets. Nov. 2009; 10(11):1156-1163. doi: 10.2174/138945009789735174.
Kaplan et al., Monitoring dynamic changes in lymph metabolome of fasting and fed rats by electrospray ionization-ion mobility mass spectrometry (ESI-IMMS). Anal Chem. Oct. 1, 2009;81(19):7944-53. doi: 10.1021/ac901030k.
Kaska et al., Improved glucose metabolism following bariatric surgery is associated with increased circulating bile acid concentrations and remodeling of the gut microbiome. World J Gastroenterol. Oct. 21, 2016;22(39):8698-8719. doi: 10.3748/wjg.v22.i39.8698.
Katsuma et al., Bile acids promote glucagon-like peptide-1 secretion through TGR5 in a murine enteroendocrine cell line STC-1. Biochem Biophys Res Commun. Apr. 1, 2005;329(1):386-90. doi: 10.1016/j.bbrc.2005.01.139.
Kawamoto et al., Purification and Characterization of a New Hydrolase for Conjugated Bile Acids, Chenodeoxycholyltaurine Hydrolase, From Bacteroides Vulgatus. J. Biochem. 1989; 106(6): 1049-1053.
Khorgami et al., Trends in utilization of bariatric surgery, 2010-2014: sleeve gastrectomy dominates. Surg Obes Relat Dis. May 2017;13(5):774-778. doi: 10.1016/j.soard.2017.01.031. Epub Jan. 25, 2017.
Kraal et al., The Prevalence of Species and Strains in the Human Microbiome: a Resource for Experimental Efforts. PLOS One. 2014; 9(5): e97279.
Kuhre et al., Peptide production and secretion in GLUTag, NCI-H716, and STC-1 cells: a comparison to native L-cells. J Mol Endocrinol. Apr. 2016;56(3):201-11. doi: 10.1530/JME-15-0293. Epub Jan. 27, 2016.
Larraufie et al., Important Role of the GLP-1 Axis for Glucose Homeostasis after Bariatric Surgery. Cell Rep. Feb. 5, 2019;26(6):1399-1408.e6. doi: 10.1016/j.celrep.2019.01.047.

Lastya et al., The low level of glucagon-like peptide-1 (glp-1) is a risk factor of type 2 diabetes mellitus. BMC Res Notes. Nov. 26, 2014;7:849. doi: 10.1186/1756-0500-7-849.
Lebel et al., Boc-Protected Amines via a Mild and Efficient One-Pot Curtius Rearrangement. Org Lett. 2005; 7(19): 4107-4110.
Lepage et al., Separation of sulfated from non-sulfated serum bile acids without the use of Sephadex cols. J Lipid Res. May 1981;22(4):705-11.
Lespessailles et al., Vitamin D alteration associated with obesity and bariatric surgery. Exp Biol Med (Maywood). May 2017;242(10):1086-1094. doi: 10.1177/1535370216688567. Epub Jan. 1, 2017.
Lewis et al., Inactivation of Protein Tyrosine Phosphatases by Dietary Isothiocyanates. Bioorganic & Medicinal Chemistry Letters. 2015; 25(20):4549-52.
Li et al., Bile acids as metabolic regulators. Curr Opin Gastroenterol. Mar. 2015 ; 31(2): 159-165. doi:10.1097/MOG.0000000000000156.
Li et al., Microbiome Remodelling Leads to Inhibition of Intestinal Farnesoid X Receptor Signalling and Decreased Obesity. Nat Commun. 2013;4:2384. doi: 10.1038/ncomms3384.
Lianidou et al., Enzymic fluorimetric determination of sulphated and non-sulphated primary bile acids in urine using a rapid solvolysis technique. Analyst. Sep. 1988;113(9):1459-63. doi: 10.1039/an9881301459.
Liu et al., Developing Irreversible Inhibitors of the Protein Kinase Cysteinome. Chemistry & Biology. 2013; 20(2): 146-159.
Liu et al., Role of gut microbiota, bile acids and their cross-talk in the effects of bariatric surgery on obesity and type 2 diabetes. J Diabetes Investig. Jan. 2018;9(1):13-20. doi: 10.1111/jdi.12687. Epub Jun. 12, 2017.
Lutz et al., M. The Use of Rat and Mouse Models in Bariatric Surgery Experiments. Front Nutr. Aug. 5, 2016;3:25. doi: 10.3389/fnut.2016.00025. eCollection 2016.
Ma et al., Gut Microbiome-Mediated Bile Acid Metabolism Regulates Liver Cancer via NKT Cells. Science. 2018; 360 (6391): eaan5931.
Madsbad, The role of glucagon-like peptide-1 impairment in obesity and potential therapeutic implications. Diabetes Obes Metab. Jan. 2014; 16(1):9-21. doi: 10.1111/dom.12119. Epub May 26, 2013.
Magouliotis et al., Impact of Bariatric Surgery on Metabolic and Gut Microbiota Profile: a Systematic Review and Meta-analysis. Obes Surg. May 2017;27(5):1345-1357. doi: 10.1007/s11695-017-2595-8.
Mahowald et al., Characterizing a model human gut microbiota composed of members of its two dominant bacterial phyla. Proc Natl Acad Sci U S A. Apr. 7, 2009;106(14):5859-64. doi: 10.1073/pnas.0901529106. Epub Mar. 24, 2009.
Makishima et al., Vitamin D Receptor as an Intestinal Bile Acid Sensor. Science. May 17, 2002; 296 (5571): 1313-1316.
Manchanda et al., Vitamin D receptor and type 2 diabetes mellitus: Growing therapeutic opportunities. Indian J Hum Genet. Sep. 2012; 18(3):274-5. doi: 10.4103/0971-6866.107975.
Marschall et al., The major metabolites of ursodeoxycholic acid in human urine are conjugated with N-acetylglucosamine. Hepatology. Oct. 1994;20(4 Pt 1):845-53. doi: 10.1002/hep.1840200412.
Martinez-Augustin et al., Intestinal bile acid physiology and pathophysiology. World J Gastroenterol. Oct. 7, 2008;14(37):5630-40. doi: 10.3748/wjg.14.5630.
McCoy et al., Phaser crystallographic software. J Appl Crystallogr. Aug. 1, 2007;40(Pt 4):658-674. doi: 10.1107/S0021889807021206. Epub Jul. 13, 2007.
McDonald et al., Partitioning of polar fatty acids into lymph and portal vein after intestinal absorption in the rat. Q J Exp Physiol. Apr. 1987;72(2):153-9. doi: 10.1113/expphysiol.1987.sp003059.
McDonald et al., Portal venous transport of long-chain fatty acids absorbed from rat intestine. Am J Physiol. Sep. 1980;239(3):G141-50. doi: 10.1152/ajpgi.1980.239.3.G141.
McGavigan et al., TGR5 contributes to glucoregulatory improvements after vertical sleeve gastrectomy in mice. Gut. Feb. 2017;66(2):226-234. doi: 10.1136/gutjnl-2015-309871. Epub Oct. 28, 2015.
Medina et al., Distinct patterns in the gut microbiota after surgical or medical therapy in obese patients. PeerJ. Jun. 20, 2017;5:e3443. doi: 10.7717/peerj.3443. eCollection 2017.

(56) References Cited

OTHER PUBLICATIONS

Mertens et al., Bile Acid Signaling Pathways from the Enterohepatic Circulation to the Central Nervous System. Front Neurosci. Nov. 7, 2017;11:617. doi: 10.3389/fnins.2017.00617. eCollection 2017.
Mi et al., Covalent Binding to Tubulin by Isothiocyanates. a Mechanism of Cell Growth Arrest and Apoptosis. J Biol Chem. 2008; 283(32): 22136-22146.
Miller et al., Targeting Protein Kinases with Selective and Semipromiscuous Covalent Inhibitors. Meth Enzymol. 2014; 548: 93-116.
Miyata et al., Enterobacteria modulate intestinal bile acid transport and homeostasis through apical sodium-dependent bile acid transporter (SLC10A2) expression. J Pharmacol Exp Ther. Jan. 2011;336(1):188-96. doi: 10.1124/jpet.110.171736. Epub Sep. 30, 2010.
Modica et al., Deciphering the Nuclear Bile Acid Receptor FXR Paradigm. Nucl Recept Signal. 2010; 8:e005.
Moore et al., Intestinal Floras of Populations That Have a High Risk of Colon Cancer. Appl Environ Microbiol. 1995; 61(9): 3202-7.
Morin et al., Collaboration gets the most out of software. Elife. Sep. 10, 2013;2:e01456. doi: 10.7554/eLife.01456.
Moser et al., Bile Salt Hydrolase Activity and Resistance to Toxicity of Conjugated Bile Salts Are Unrelated Properties in Lactobacilli. Appl Environ Microbiol. Aug. 2001;67(8):3476-80. doi: 10.1128/AEM.67.8.3476-3480.2001.
Myronovych et al., Vertical sleeve gastrectomy reduces hepatic steatosis while increasing serum bile acids in a weight-loss-independent manner. Obesity (Silver Spring). Feb. 2014;22(2):390-400. doi: 10.1002/oby.20548. Epub Sep. 5, 2013.
Nair et al., The enzymatic cleavage of the carbon-nitrogen bond in 3-alpha, 7-alpha, 12-alpha-trihydroxy-5-beta-cholan-24-oylglycine. J Biol Chem. Jan. 10, 1967;242(1):7-11.
Nemati et al., Increased Bile Acids and FGF19 After Sleeve Gastrectomy and Roux-en-Y Gastric Bypass Correlate with Improvement in Type 2 Diabetes in a Randomized Trial. Obes Surg. Sep. 2018;28(9):2672-2686. doi: 10.1007/s11695-018-3216-x.
Nishida et al., Modulation of bile acid metabolism by 1alphahydroxyvitamin D3 administration in mice. Drug Metab Dispos. Oct. 2009;37(10):2037-44. doi: 10.1124/dmd.109.027334. Epub Jul. 6, 2009.
Ogasawara et al., Biliary excretion of phenolphthalein glucuronide in the rat. Hepatol Res. Jun. 2001;20(2):221-231. doi: 10.1016/s1386-6346(00)00143-1.
Pageaux et al., Bile acid sulfates in serum bile acids determination. Steroids. Jul. 1979;34(1):73-88. doi: 10.1016/0039-128x(79)90127-2.
Park et al., Metabolism of fluorine-containing drugs. Annu Rev Pharmacol Toxicol. 2001;41:443-70. doi: 10.1146/annurev.pharmtox.41.1.443.
Parmentier et al., Cholic acid-7-sulfate, a major bile acid in the large intestine of the mouse. Adv. Bile Acid Res., Bile Acid Meet., 3rd (1975), Meeting Date 1974, 139-44.
Parmentier et al., Synthesis and characteristics of the specific monosulfates of chenodeoxycholate, deoxycholate and their taurine or glycine conjugates. Steroids. Nov. 1977;30(5):583-90. doi: 10.1016/0039-128x(77)90049-6.
Parmentier et al., Synthesis of the specific monosulfates of cholic acid. Steroids. Dec. 1975;26(6):721-9. doi: 10.1016/0039-128x(75)90105-1.
Parmentier et al., Thin-layer chromatography of bile salt sulfates. Journal of Chromatography. 1978; 152(1):285-9.
Patti et al., Serum bile acids are higher in humans with prior gastric bypass: potential contribution to improved glucose and lipid metabolism. Obesity (Silver Spring). Sep. 2009;17(9):1671-7. doi: 10.1038/oby.2009.102. Epub Apr. 9, 2009.
Peng et al., Liquid-liquid extraction combined with differential isotope dimethylaminophenacyl labeling for improved metabolomic profiling of organic acids. Anal Chim Acta. Nov. 25, 2013;803:97-105. doi: 10.1016/j.aca.2013.07.045. Epub Jul. 27, 2013.

Pols et al., Lithocholic Acid Controls Adaptive Immune Responses by Inhibition of Th1 Activation Through the Vitamin D Receptor. PLOS One. 2017; 12(5): e0176715.
Princen et al., One-step solvolysis of 3-, 7- and 12-sulfated free and conjugated bile acids. Clin Chim Acta. Nov. 15, 1990;192(1):77-83. doi: 10.1016/0009-8981(90)90274-v.
Quintás-Cardama et al., Kinase Inhibitors for the Treatment of Myeloproliferative Neoplasias and Beyond. Nature Reviews Drug Discovery. 2011; 10(2): 127-140.
Raedsch et al., Separation of individual sulfated bile acid conjugates as calcium complexes using reversed-phase partition thin-layer chromatography. J Lipid Res. Aug. 1979;20(6):789-95.
Ridaura et al., Gut Microbiota From Twins Discordant for Obesity Modulate Metabolism in Mice. Science. 2013; 341(6150): 1241214.
Ridlon et al., Bile Salt Biotransformations by Human Intestinal Bacteria. J Lipid Res. 2006; 47(2): 241-259.
Rizzo et al., Functional characterization of the semisynthetic bile acid derivative INT-767, a dual farnesoid X receptor and TGR5 agonist. Mol Pharmacol. Oct. 2010;78(4):617-30. doi: 10.1124/mol.110.064501. Epub Jul. 14, 2010.
Robben et al., Formation of delta 2- and delta 3-cholenoic acids from bile acid 3-sulfates by a human intestinal Fusobacterium strain. Appl Environ Microbiol. Nov. 1989;55(11):2954-9. doi: 10.1128/AEM.55.11.2954-2959.1989.
Roberts et al., Development of a Gut Microbe-Targeted Nonlethal Therapeutic to Inhibit Thrombosis Potential. Nat. Med. 2018; 24(9): 1407-1417.
Roda et al., Quantitative aspects of the interaction of bile acids with human serum albumin. J Lipid Res. Mar. 1982;23(3):490-5.
Rodrigues et al., The site-specific delivery of ursodeoxycholic acid to the rat colon by sulfate conjugation. Gastroenterology. Dec. 1995; 109(6):1835-44. doi: 10.1016/0016-5085(95)90750-5.
Rossocha et al., Conjugated Bile Acid Hydrolase Is a Tetrameric N-Terminal Thiol Hydrolase with Specific Recognition of Its Cholyl but Not of Its Tauryl Product. Biochem. 2005; 44(15): 5739-5748.
Runge-Morris et al., Regulation of the cytosolic sulfotransferases by nuclear receptors. Drug Metab Rev. Feb. 2013;45(1):15-33. doi: 10.3109/03602532.2012.748794.
Ryan et al., FXR is a molecular target for the effects of vertical sleeve gastrectomy. Nature. May 8, 2014;509(7499):183-8. doi: 10.1038/nature13135. Epub Mar. 26, 2014.
Sampson et al., Gut Microbiota Regulate Motor Deficits and Neuroinflammation in a Model of Parkinson's Disease. Cell. 2016; 167(6): 1469-80.
Sandler et al., Short-Term Benefit From Oral Vancomycin Treatment of Regressive-Onset Autism. Journal of Child Neurology. 2016; 15(7): 429-435.
Sano et al., Estradiol-17 beta-glucuronide-induced cholestasis. Effects of ursodeoxycholate-3-O-glucuronide and 3,7-disulfate. J Hepatol. Feb. 1993;17(2):241-6. doi: 10.1016/s0168-8278(05)80045-5.
Santhekadur et al., Preclinical models of non-alcoholic fatty liver disease. J Hepatol. Feb. 2018;68(2):230-237. doi: 10.1016/j.jhep.2017.10.031. Epub Nov. 9, 2017.
Sasaki et al., Separation of double conjugates of bile acids by two-dimensional high-performance thin-layer chromatography with tetra-n-butylammonium phosphate and methyl β-cyclodextrin. Chromatographia. 1999; 49(11/12): 681-685.
Sato et al., Novel Potent and Selective Bile Acid Derivatives as TGR5 Agonists: Biological Screening, Structure-Activity Relationships, and Molecular Modeling Studies. J Med Chem. Mar. 27, 2008;51(6):1831-41. doi: 10.1021/jm7015864. Epub Feb. 29, 2008.
Sayin et al., Gut Microbiota Regulates Bile Acid Metabolism by Reducing the Levels of Tauro-Beta-Muricholic Acid, a Naturally Occurring FXR Antagonist. Cell Metab. 2013; 17(2): 225-235.
Schloss et al., Introducing mothur: open-source, platform-independent, community-supported software for describing and comparing microbial communities. Appl Environ Microbiol. Dec. 2009;75(23):7537-41. doi: 10.1128/AEM.01541-09. Epub Oct. 2, 2009.
Serafimova et al., Reversible Targeting of Noncatalytic Cysteines with Chemically Tuned Electrophiles. Nature Chemical Biology. 2012; 8(5): 471-476.

(56) References Cited

OTHER PUBLICATIONS

Setchell et al., General methods for the analysis of metabolic profiles of bile acids and related compounds in feces. J Lipid Res. 1983; 24: 1085-1100.
Setchell et al., Serum bile acid analysis. Clin Chim Acta. Jan. 7, 1983;127(1):1-17. doi: 10.1016/0009-8981(83)90070-0.
Setchell et al., Ursodeoxycholic acid-disulphate (SUDCA)—a potent chemopreventive agent against colon cancer in: Bile Acids: Biological Actions and Clinical Relevance. Falk Symposium 155. 2007; 194-200.
Shang et al., Colesevelam improves insulin resistance in a diet-induced obesity (F-DIO) rat model by increasing the release of GLP-1. Am J Physiol Gastrointest Liver Physiol. Mar. 2010;298(3):G419-24. doi: 10.1152/ajpgi.00362.2009. Epub Dec. 31, 2009.
Sisley et al., Hypothalamic Vitamin D Improves Glucose Homeostasis and Reduces Weight. Diabetes. Sep. 2016;65(9):2732-41. doi: 10.2337/db16-0309. Epub May 23, 2016.
Smith et al., Discovery of Bile Salt Hydrolase Inhibitors Using an Efficient High-Throughput Screening System. PLOS One. 2014; 9(1): e85344.
Solbach et al., BaiCD gene cluster abundance is negatively correlated with Clostridium difficile infection. PLOS One. May 8, 2018;13(5):e0196977. doi: 10.1371/journal.pone.0196977. eCollection 2018.
Song et al., Selective Activation of Liver X Receptor Alpha by 6alpha-Hydroxy Bile Acids and Analogs. Steroids. 2000; 65(8): 423-427.
Song et al., Taxonomic Profiling and Populational Patterns of Bacterial Bile Salt Hydrolase (BSH) Genes Based on Worldwide Human Gut Microbiome. Microbiome. 2019; 7(1): 9.
Spiljar et al., The Immune System Bridges the Gut Microbiota with Systemic Energy Homeostasis: Focus on TLRs, Mucosal Barrier, and SCFAs. Front Immunol. 2017; 8: 1353.
Staudinger et al., The Nuclear Receptor PXR Is a Lithocholic Acid Sensor That Protects Against Liver Toxicity. PNAS. 2001; 98(6):3369-3374.
Steinert et al., Intestinal GLP-1 and satiation: from man to rodents and back. Int J Obes (Lond). Feb. 2016;40(2):198-205. doi: 10.1038/ijo.2015.172. Epub Aug. 28, 2015.
Stellwag et al., Purification and Characterization of Bile Salt Hydrolase From Bacteroides Fragilis Subsp. Fragilis. Biochim Biophys Acta. Nov. 8, 1976;452(1):165-76. doi: 10.1016/0005-2744(76)90068-1.
Stoltz et al., Synthesis and Biological Evaluation of Bile Acid Analogues Inhibitory to Clostridium difficile Spore Germination. J Med Chem. Apr. 27, 2017;60(8):3451-3471. doi: 10.1021/acs.jmedchem.7b00295. Epub Apr. 12, 2017.
Strelow, A Perspective on the Kinetics of Covalent and Irreversible Inhibition. SLAS Discov. 2017; 22(1): 3-20.
Summerfield et al., Renal synthesis of bile acid sulphates: evidence from man and the isolated perfused rat kidney. Clinical Science and Molecular Medicine. 1976; 50(2): 25P-26P.
Summerfield et al., Synthesis of bile acid monosulphates by the isolated perfused rat kidney. Biochem J. May 15, 1976;156(2):339-45. doi: 10.1042/bj1560339.
Sun et al., Gut Microbiota and Intestinal FXR Mediate the Clinical Benefits of Metformin. Nat. Med. 2018; 24(12): 1919-1929.
Sun et al., Identification of functionally relevant residues of the rat ileal apical sodium-dependent bile acid cotransporter. J Biol Chem. Jun. 16, 2006;281(24):16410-8. doi: 10.1074/jbc.M600034200. Epub Apr. 11, 2006.
Takikawa et al., Binding of bile acids by glutathione S-transferases from rat liver. J Lipid Res. Sep. 1986;27(9):955-66.
Takikawa et al., Comparison of the affinities of newly identified human bile acid binder and cationic glutathione S-transferase for bile acids. J Lipid Res. Jun. 1986;27(6):652-7.
Takikawa et al., Effects of organic anions and bile acids on biliary lipid excretion in hyperbilirubinemic mutant Sprague-Dawley rats. J Hepatol. Feb. 1993;17(2):247-52. doi: 10.1016/s0168-8278(05)80046-7.
Takikawa et al., Effects of ursodeoxycholate and its conjugates on biliary glutathione excretion in rats. Dig Dis Sci. Oct. 1996;41(10):1953-8. doi: 10.1007/BF02093595.
Takikawa et al., Effects of ursodeoxycholate, its glucuronide and disulfate and beta-muricholate on biliary bicarbonate concentration and biliary lipid excretion. J Hepatol. May 1992; 15(1-2):77-84. doi: 10.1016/0168-8278(92)90015-h.
Takikawa et al., Enhanced biliary excretion of lithocholate-3-sulfate by ursodeoxycholate-3,7-disulfate infusion in Eisai hyperbilirubinemic rat (EHBR). Dig Dis Sci. Jan. 1998;43(1):188-92. doi: 10.1023/a:1018809028425.
Tan et al., A multi-chamber microfluidic intestinal barrier model using Caco-2 cells for drug transport studies. PLoS One. May 10, 2018;13(5):e0197101. doi: 10.1371/journal.pone.0197101. eCollection 2018.
Tanaka et al., Bile Salt Hydrolase of Bifidobacterium Longum-Biochemical and Genetic Characterization. Appl Environ Microbiol. 2000; 66(6): 2502-2512.
Thaiss et al., The Microbiome and Innate Immunity. Nature. 2016; 535 (7610): 65-74.
Tiscornia et al., A general method for gene knockdown in mice by using lentiviral vectors expressing small interfering RNA. Proc Natl Acad Sci U S A. Feb. 18, 2003;100(4):1844-8. doi: 10.1073/pnas.0437912100. Epub Jan. 27, 2003.
Tremaroli et al., Roux-en-Y Gastric Bypass and Vertical Banded Gastroplasty Induce Long-Term Changes on the Human Gut Microbiome Contributing to Fat Mass Regulation. Cell Metab. Aug. 4, 2015;22(2):228-38. doi: 10.1016/j.cmet.2015.07.009.
Tserng et al., Bile acid sulfates. III. Synthesis of 7- and 12-monosulfates of bile acids and their conjugates using a sulfur trioxide-triethylamine complex. Steroids. Feb. 1979;33(2):167-82. doi: 10.1016/0039-128x(79)90024-2.
Turnbaugh et al., An Obesity-Associated Gut Microbiome with Increased Capacity for Energy Harvest. Nature. 2006; 444(7122): 1027-31.
Uegaki et al., Effect of organic anions and bile acid conjugates on biliary excretion of taurine-conjugated bile acid sulfates in the rat. Steroids. Nov. 1999;64(11):790-5. doi: 10.1016/s0039-128x(99)00071-9.
Van De Laarschot et al., The role of bile salts in liver regeneration. Hepatol Int. Sep. 2016;10(5):733-40. doi: 10.1007/s12072-016-9723-8. Epub Apr. 5, 2016.
Vavassori et al., The Bile Acid Receptor FXR Is a Modulator of Intestinal Innate Immunity. J. Immunol. 2009; 183(10): 6251-6261.
Verhoeckx et al., Caco-2 Cell Line. The Impact of Food Bioactives on Health. 2015; 175:103-111.
Wahlstrom et al., Intestinal Crosstalk between Bile Acids and Microbiota and Its Impact on Host Metabolism. Cell Metab. Jul. 12, 2016;24(1):41-50. doi: 10.1016/j.cmet.2016.05.005. Epub Jun. 16, 2016.
Walker et al., Importance of sulfur-containing metabolites in discriminating fecal extracts between normal and type-2 diabetic mice. J Proteome Res. Oct. 3, 2014;13(10):4220-31. doi: 10.1021/pr500046b. Epub Sep. 2, 2014.
Wallace et al., Alleviating Cancer Drug Toxicity by Inhibiting a Bacterial Enzyme. Science. 2010; 330(6005): 831-835.
Wang et al., Identification and Characterization of a Bile Salt Hydrolase From Lactobacillus Salivarius for Development of Novel Alternatives to Antibiotic Growth Promoters. Appl. Environ. Microbiol. 2012; 78(24): 8795-8802.
Weber et al., Nephele: a cloud platform for simplified, standardized and reproducible microbiome data analysis. Bioinformatics. Apr. 15, 2018;34(8):1411-1413. doi: 10.1093/bioinformatics/btx617.
Weerapana et al., Tandem orthogonal proteolysis-activity-based protein profiling (TOP-ABPP)—a general method for mapping sites of probe modification in proteomes. Nat Protoc. 2007;2(6):1414-25. doi: 10.1038/nprot.2007.194.

(56) References Cited

OTHER PUBLICATIONS

Wilson et al., Keap Calm, and Carry on Covalently. J Med Chem. Oct. 10, 2013;56(19):7463-76. doi: 10.1021/jm400224q. Epub Jul. 25, 2013.

Wrzosek et al. Transplantation of human microbiota into conventional mice durably reshapes the gut microbiota. Sci Rep. May 1, 2018;8(1):6854. doi: 10.1038/s41598-018-25300-3.

Xie et al., An Intestinal Farnesoid X Receptor-Ceramide Signaling Axis Modulates Hepatic Gluconeogenesis in Mice. Diabetes. 2017; 66 (3): 613-626.

Xie et al., Pharmacological Targeting of the Pseudokinase Her3. Nature Chemical Biology. 2014; 10(12): 1006-1012.

Yang et al., MX1013, a Dipeptide Caspase Inhibitor with Potent in Vivo Antiapoptotic Activity. Br. J. Pharmacol. 2003; 140(2): 402-412.

Yao et al., A selective gut bacterial bile salt hydrolase alters host metabolism. Elife. Jul. 17, 2018;7:e37182. doi: 10.7554/eLife. 37182.

Yao et al., Nontargeted analysis of the urine nonpolar sulfateome: a pathway to the nonpolar xenobiotic exposome. Rapid Commun Mass Spectrom. Nov. 15, 2016;30(21):2341-2350. doi: 10.1002/rcm.7726.

Yousef et al., Effect of complete sulfation of bile acids on bile formation: role of conjugation and number of sulfate groups. Hepatology. Mar. 1992;15(3):438-45. doi: 10.1002/hep. 1840150314.

Zhang et al., Effects of feeding bile acids and a bile acid sequestrant on hepatic bile acid composition in mice. J Lipid Res. Nov. 2010;51(11):3230-42. doi: 10.1194/jlr.M007641. Epub Jul. 29, 2010.

Zhang et al., Lake char (*Salvelinus namaycush*) olfactory neurons are highly sensitive and specific to bile acids. J Comp Physiol A Neuroethol Sens Neural Behav Physiol. Feb. 2009;195(2):203-15. doi: 10.1007/s00359-008-0399-y. Epub Jan. 10, 2009.

Zybailov et al., Statistical analysis of membrane proteome expression changes in *Saccharomyces cerevisiae*. J Proteome. Sep. 2006;5(9):2339-47. doi: 10.1021/pr060161n.

U.S. Appl. No. 17/309,520, filed Jun. 3, 2021, Devlin et al.

PCT/US2019/047856, Dec. 10, 2019, International Search Report and Written Opinion.

PCT/US2019/047856, Mar. 4, 2021, International Preliminary Report on Patentability.

PCT/US2019/047856, Jul. 16, 2020, Invitation to Pay Additional Fees.

PCT/US2020/032016, Sep. 22, 2020, International Search Report and Written Opinion.

PCT/US2019/064488, Apr. 9, 2020, International Search Report and Written Opinion.

PCT/US2019/064488, Jun. 17, 2021, International Preliminary Report on Patentability.

\* cited by examiner

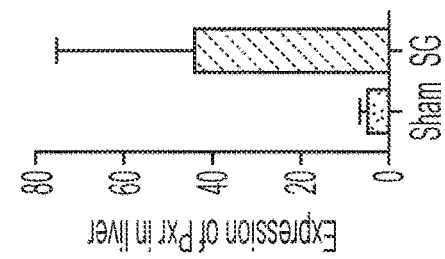
FIG. 6F
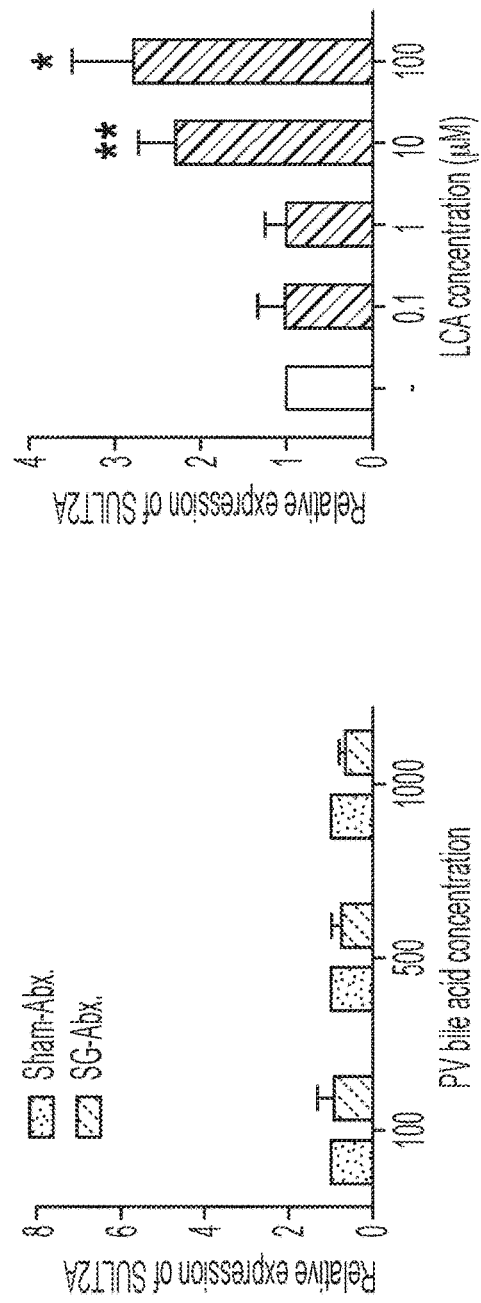
FIG. 6E
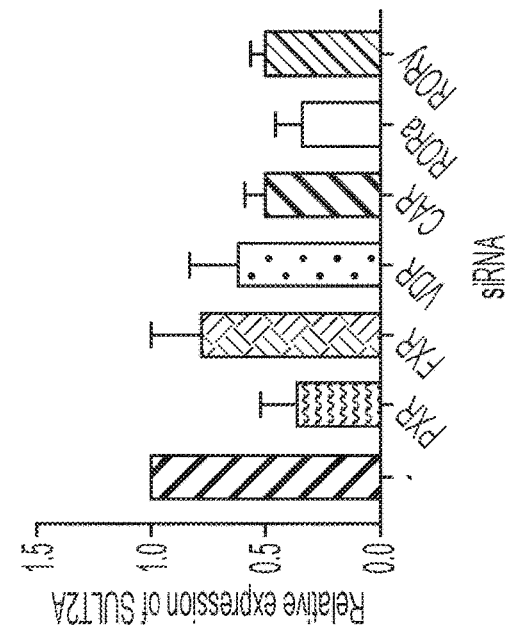
FIG. 6H
FIG. 6G cholic acid-7-sulfate (CA7S)

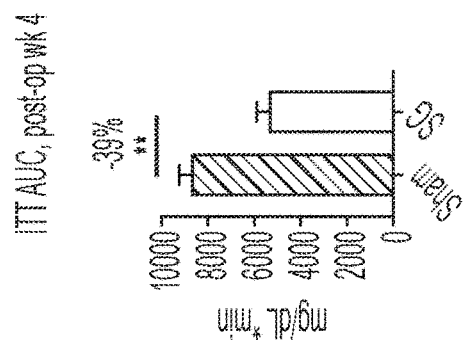
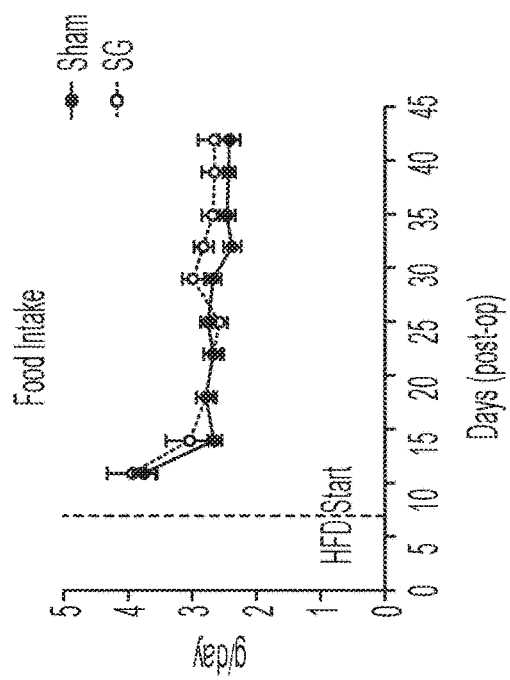
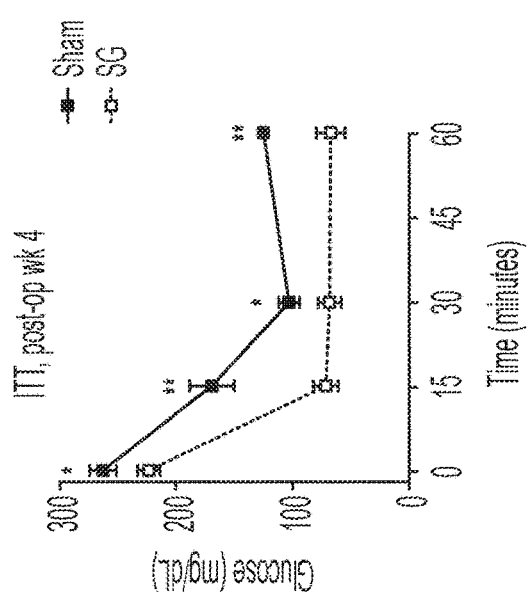
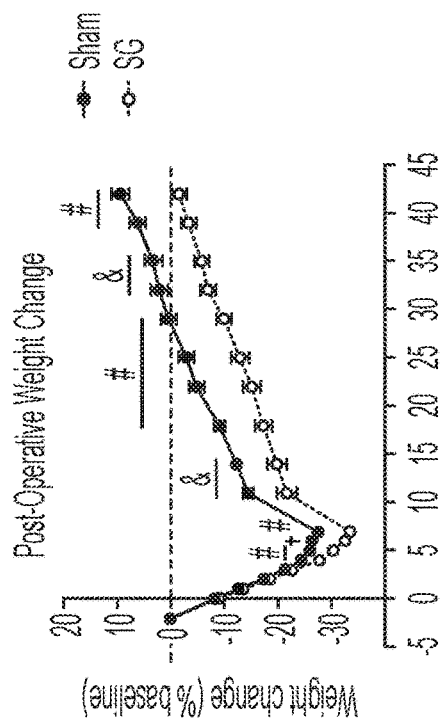
FIG. 20A
FIG. 20B
FIG. 20C
FIG. 20D

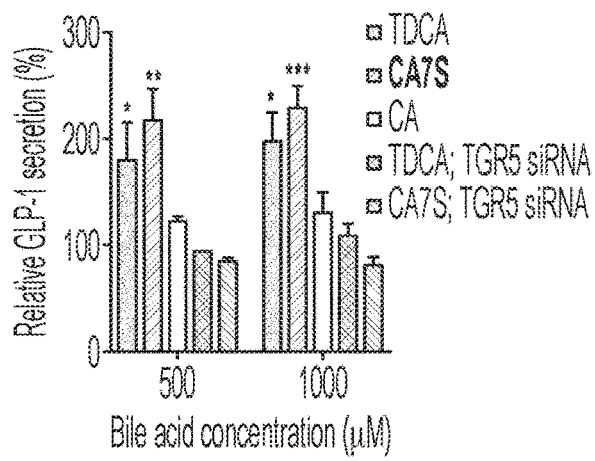
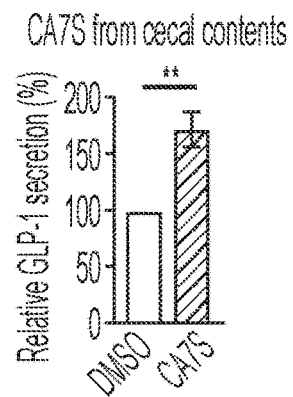
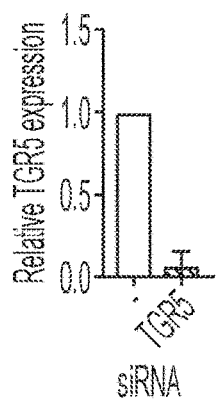
FIG. 21A
FIG. 21B
FIG. 21C
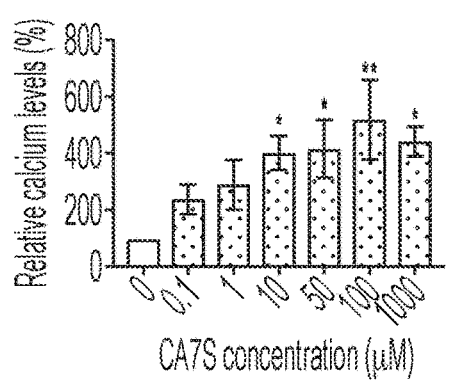
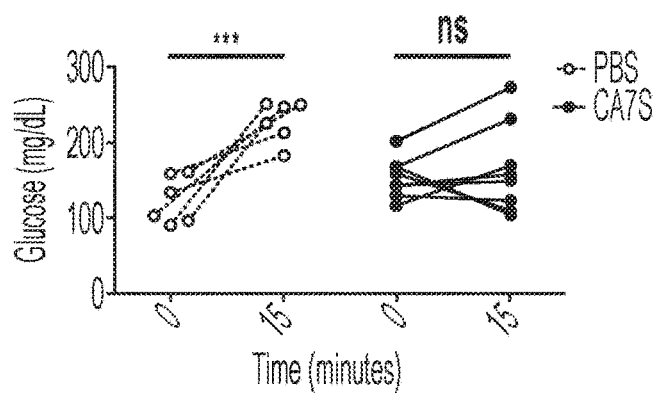
FIG. 21D
FIG. 21E 
COMPOSITIONS AND METHODS RELATED TO CHOLIC ACID 7-SULFATE AS A TREATMENT FOR DIABETES

RELATED APPLICATIONS

This application is a national stage filing under 35 U.S.C. § 371 of International PCT Application, PCT/US2019/047856, filed Aug. 23, 2019, which claims priority under 35 U.S.C. § 119 (e) to U.S. Provisional Application, U.S. Ser. No. 62/722,010, filed Aug. 23, 2018, each of which is incorporated herein by reference.

GOVERNMENT SUPPORT

This invention was made with government support under GM128618 and DK057521 awarded by the National Institutes of Health. The government has certain rights in the invention.

REFERENCE TO AN ELECTRONIC SEQUENCE LISTING

The contents of the electronic sequence listing (H082470338US03-SEQ-DCS.txt; Size: 1,967 bytes; and Date of Creation: Sep. 10, 2024) is herein incorporated by reference in its entirety.

FIELD OF THE INVENTION

The present disclosure relates to the treatment of obesity and diabetes.

BACKGROUND

Obesity and type 2 diabetes (T2D) are medical pandemics. Bariatric surgery, in the form of Roux-en-Y gastric bypass or sleeve gastrectomy (SG), is currently the most effective and lasting treatment for obesity and related comorbidities (Batterham, R. L., et al. Diabetes Care 2016 39, 893-901; Gloy, V. L. et al., BMJ 2013, 347, f5934-f5934). While maximal weight-loss occurs at 1 year, remarkably, many patients see resolution of their T2D within hours to days of surgery (Abbasi, J. JAMA, 2017, 317, 571-574). For a majority of patients, remission is durable and lasts for years after surgery.

Two changes consistently observed following bariatric surgery are increased levels of Glucagon-like peptide-1 (GLP-1), a circulating incretin hormone, and changes in the systemic repertoire of bile acids (BAs) (Kaska, L., et al. J. World J. Gastroenterol. 2016, 22, 8698-8719). BAs are cholesterol-derived metabolites that play crucial roles in host metabolism by acting as detergents that aid in the absorption of lipids and vitamins, and as ligands for host receptors (Fiorucci, S., et al., Trends Mol Med. 2015, 21, 702-714). BAs have been implicated in post-SG therapeutic benefits due to their ability to mediate farnesoid X receptor (FXR) signaling (Ryan, K. K. et al. Nature 2014, 509, 183-188). However, the causal role of BAs in eliciting beneficial metabolic changes post-surgery remains unclear. Thus far, research efforts have focused on overall changes in the total BA pool or in levels of BAs conjugated to amino acids (Patti, M.-E. et al. Obesity (Silver Spring) 2009, 17, 1671-1677). Individual BAs, however, have different binding affinities for nuclear hormone receptors (NhRs) and GPCRs, and thus unique abilities to modulate glucose homeostasis, lipid accumulation, and energy expenditure (Patti, M.-E. et al. Obesity (Silver Spring) 2009, 17, 1671-1677; Sayin, S. I. et al. Cell Metab., 2013, 17, 225-235).

Diabetes mellitus is a disease that characterized by the lack of insulin production (e.g. type 1 diabetes) by the pancreas or a lack of insulin sensitivity (e.g. type II diabetes). Patients with diabetes mellitus are diagnosed by a glucose tolerance test. The plasma glucose levels are elevated in patients diagnosed with diabetes compared with healthy patients. Diabetes can result in a number of long term complications including diabetic ketoacidosis, hyperosmolar hyperglycemic state, or death. Serious long-term complications include cardiovascular disease, stroke, chronic kidney disease, foot ulcers, and damage to the eyes. Current treatments, such as insulin injections, manage the symptoms but do not prevent the long term complications of the disease and require constant monitoring of blood glucose levels. New treatments for diabetes are needed to improve the quality of life and prevent future complications of the disease.

SUMMARY OF THE INVENTION

The compositions and methods described herein are related, in part, to the discovery of cholic acid-7-sulfate as a treatment for diabetes and obesity.

In one aspect, provided herein is a method for treating or preventing diabetes, the method comprising: administering to a subject in need thereof an agent that increases the level of cholic acid-7-sulfate in the subject.

In another aspect, provided herein is a method for treating or preventing obesity, the method comprising: administering to a subject in need thereof an agent that increases the level of cholic acid-7-sulfate in the subject. In another aspect, provided herein are methods for treating or preventing diabetes and/or obesity, comprising administering to a subject in need thereof an effective amount of cholic acid-7-sulfate. In certain aspects, the agent that increases the level of cholic acid-7-sulfate in a subject is cholic acid-7-sulfate.

Compositions and kits comprising cholic acid-7-sulfate and/or compositions, and methods of treatment using cholic acid-7-sulfate or compositions thereof are provided herein.

The details of certain embodiments of the invention are set forth in the Detailed Description of Certain Embodiments, as described below. Other features, objects, and advantages of the invention will be apparent from the Definitions, Examples, and Claims.

In one embodiment, the agent is cholic acid-7-sulfate.
In one embodiment, the agent is a TGR5 agonist.
In one embodiment, the TGR5 agonist induces GLP-1 secretion from a target cell. In some embodiments, the activity of TGR5 is increased by at least 50%, at least 60%, at least 70%, at least 80%, at least 90%, or more as compared to a control. In some embodiments, the secretion of GLP1 is increased by at least 50%, at least 60%, at least 70%, at least 80%, at least 90%, or more as compared to a control.

In one embodiment, the agent is selected from the group consisting of a small molecule, an antibody, a peptide, a genome editing system, an antisense oligonucleotide, and an RNAi.

In some embodiments, the agent is a vector that encodes the agent. In one embodiment, the vector is non-integrative or integrative. In one embodiment, the vector is a viral vector.

In one embodiment, the agent is formulated with a pharmaceutical composition.

In one embodiment, the pharmaceutical composition is formulated to restrict delivery of an agent to the gastrointestinal tract of the subject.

In one embodiment, the diabetes is type I, type II, neonatal, or maturity onset diabetes in the young.

In one embodiment, the administering reduces glucose levels in the serum of a subject.

In one embodiment, wherein the subject is a mammal.

In one embodiment, the mammal is a human.

In one embodiment, the target cell is an enteroendocrine cell, an epithelial cell, an L-cell, or a neuron.

In one aspect, described herein is a composition comprising an agent that increases the level of cholic acid-7-sulfate in a subject.

In one embodiment, wherein the agent is cholic acid-7-sulfate.

In one embodiment, the composition is formulated for treating or preventing diabetes.

In one embodiment, the composition further comprises a pharmaceutically acceptable carrier or excipient.

In one embodiment, the carrier or excipient restricts delivery of the composition to the gastrointestinal tract.

In one aspect, described herein is a method for treating or preventing diabetes, the method comprising: administering to a subject in need thereof a genetically engineered microorganism or population thereof, that expresses an agent that increases the level of cholic acid-7-sulfate.

In one embodiment, the genetically engineered microorganism is a bacterium.

In one aspect, described herein is a method for treating or preventing diabetes, the method comprising: administering to a subject in need thereof a genetically engineered microorganism or population thereof, that secretes cholic acid-7-sulfate.

In one embodiment, the genetically engineered microorganism is a bacterium.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

An "obesity-related condition" as used herein, includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity, and pre-obesity (e.g., being "over-weight") as defined by the World Health Organization.

As used herein the term "an inflammatory disease" refers to any disease that affects the immune system. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. The inflammatory disease can cause at least one symptom of the disease. These symptoms can include but are not limited to, diarrhea, vomiting, nausea, upset stomach, pain, swollen joints, malaise, fever, weight loss, weight gain, bleeding, any change in the consistency or frequency of a bowel movement or stool, or any other symptom associated with an inflammatory disease in a subject. In some embodiments, the inflammatory disease is an autoimmune disease.

Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, food intolerance, psoriasis, cystic fibrosis, diverticulitis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, gastroesophageal reflux disease (GERD), Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response.

Exemplary autoimmune diseases include, but are not limited to, Exemplary autoimmune diseases include, but are not limited to, celiac disease, glomerulonephritis, Goodpasture's syndrome, necrotizing vasculitis, lymphadenitis, periarteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst), and polyphagia (increased hunger).

Generally, diabetes is characterized and diagnosed by high blood glucose levels in a subject's serum (e.g. hyperglycemia). The diagnosis can be carried out by a physician with a glucose challenge test and/or a glucose tolerance test. For an oral glucose tolerance test in humans, a blood sugar level less than about 140 mg/dL (7.8 mmol/L) is normal. A reading of more than about 200 mg/dL (11.1 mmol/L) after two hours indicates that the subject has diabetes. A reading between about 140 and about 199 mg/dL (7.8 mmol/L and 11.0 mmol/L) can indicate prediabetes.

There are several types of diabetes. Type I diabetes results from the body's failure to produce insulin, and presently requires the person to inject insulin or wear an insulin pump. Type 2 diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes.

All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

As used herein, the terms "treat," "treatment," "treating," or "amelioration" refer to therapeutic treatments, wherein the object is to reverse, alleviate, ameliorate, inhibit, slow down, or stop the progression or severity of a condition associated with diabetes, e.g., type II diabetes. The term "treating" includes reducing or alleviating at least one adverse effect or symptom of diabetes. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "prevent" or "preventing" refers to the prevention of at least one symptom associated with diabetes, or complete prevention of diabetes, or the lessening of the severity of diabetes (e.g., preventing the progression of diabetes or complications) in a subject, and/or delaying one or more symptoms of a diabetes, and/or delaying the onset of diabetes and/or symptoms.

As used herein, the term "administering," refers to the placement of a therapeutic (e.g., an agent that increases cholic acid-7 sulfate levels) or pharmaceutical composition as disclosed herein into a subject by a method or route which results in at least partial delivery of the agent to the subject. Pharmaceutical compositions comprising agents as disclosed herein can be administered by any appropriate route which results in an effective treatment in the subject.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., diabetic or obesity model. A subject can be male or female. A subject can be at any stage of development.

A subject can be one who has been previously diagnosed with or identified as suffering from or having a disease or disorder in need of treatment (e.g., diabetes) or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

As used herein, an "agent" refers to e.g., a molecule, protein, peptide, antibody, or nucleic acid, that inhibits activity of a polypeptide or polynucleotide, or binds to, partially or totally blocks stimulation, decreases, prevents, delays activation, inactivates, desensitizes, or down-regulates the activity of the polypeptide or the polynucleotide. Agents that increase cholic acid-7-sulfate, e.g., increase secretion or act as an agonist of TGR5 receptors, e.g., improve stability, degradation, dissociation, or localization, secretion, metabolism, partially or totally enhance stimulation, activity or enzymatic activity, decrease, prevent, delay activation, inactivate, desensitize, or down regulate the activity of a polypeptide or polynucleotide. An agent can act directly or indirectly.

The term "agent" as used herein means any compound or substance such as, but not limited to, a small molecule, nucleic acid, polypeptide, peptide, drug, ion, lipid, polymer, etc. An "agent" can be any chemical (e.g., an acid or sulfate), entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, mRNAs, lipoproteins, aptamers, and modifications and combinations thereof, etc. In certain embodiments, agents are small molecule having a chemical moiety. For example, chemical moieties included unsubstituted or substituted alkyl, aromatic, or heterocyclyl moieties including macrolides, leptomycins, and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion, and other variants.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of cholic acid-7-sulfate include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\,alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA.

As used herein, the term "antibody" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include broadly neutralizing antibodies, midibodies, nanobodies, humanized antibodies, chimeric antibodies, and the like.

As used herein, the term "polypeptide" is intended to encompass a singular "polypeptide" as well as plural "polypeptides," and includes any chain or chains of two or more amino acids. Thus, as used herein, terms including, but not limited to "peptide", "dipeptide", "tripeptide", "protein", "enzyme", "amino acid chain", and "contiguous amino acid sequence" are all encompassed within the definition of a "polypeptide", and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

Methods and compositions described herein require that the levels and/or activity cholic acid-7-sulfate, TGR5, and/or GLP-1 are increased. TGR5 as described herein is specifically targeted to increase secretion of GLP-1 from a target cell.

In some embodiments, the methods increase the activity of G-protein coupled bile acid receptor 1 (GPBAR1, i.e., TGR5).

As used herein, an "control" refers to an untreated, otherwise identical cell or population (e.g., a subject who was not administered an agent described herein, or was administered by only a subset of agents described herein, as compared to a non-control cell).

As used herein the term "comprising" or "comprises" is used in reference to compositions, methods, and respective component(s) thereof, that are essential to the method or composition, yet open to the inclusion of unspecified elements, whether essential or not.

The singular terms "a", "an", and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

BRIEF DESCRIPTION OF THE DRAWINGS

FIG. 1 shows that mice are a suitable model for bariatric surgery-induced amelioration of diabetic phenotypes.

FIG. 2 shows that mice 6 weeks post-sleeve have higher levels of cholic acid-7-sulfate in their cecum compared to sham-operated mice.

FIG. 4 shows that cholic acid-7-sulfate is a TGR5 agonist and induces GLP-1 secretion in vitro.

FIG. 5 shows that acute cholic acid-7-sulfate treatment induces GLP-1 and reduces serum glucose levels in vivo.

FIG. 6 shows that portal vein bile acids induce synthesis of cholic acid-7-sulfate via SULT2A1 enzyme. FIG. 6D-E show that there was no difference in induction of SULT2A1 between the pools of bile acids mimicking those observed in the antibiotic-treated sleeve- and sham-operated mouse portal veins. FIG. 6D also shows that lithocholic acid (LCA), TDCA, cholic acid (CA), and CDCA were absent in the antibiotic-treated mouse portal veins. FIG. 6F shows that LCA induced SULT2A1 in HepG2, while others did not in all concentrations tested. FIG. 6G shows the relative expression of SULT2A of siRNA treated groups. FIG. 6H shows the relative expression of Pxr in the liver of Sham and SG mice.

FIG. 9 shows that cholic acid-7-sulfate-mediated induction of GLP-1 requires TGR5.

FIG. 20 shows diet induced obese (DIO) mice show improved insulin sensitivity and a reduction in percent body weight post-SG.

FIG. 21 shows CA7S activates TGR5, induces GLP-1 secretion, and reduces systemic glucose levels.

DETAILED DESCRIPTION OF CERTAIN EMBODIMENTS

Figure 1A:
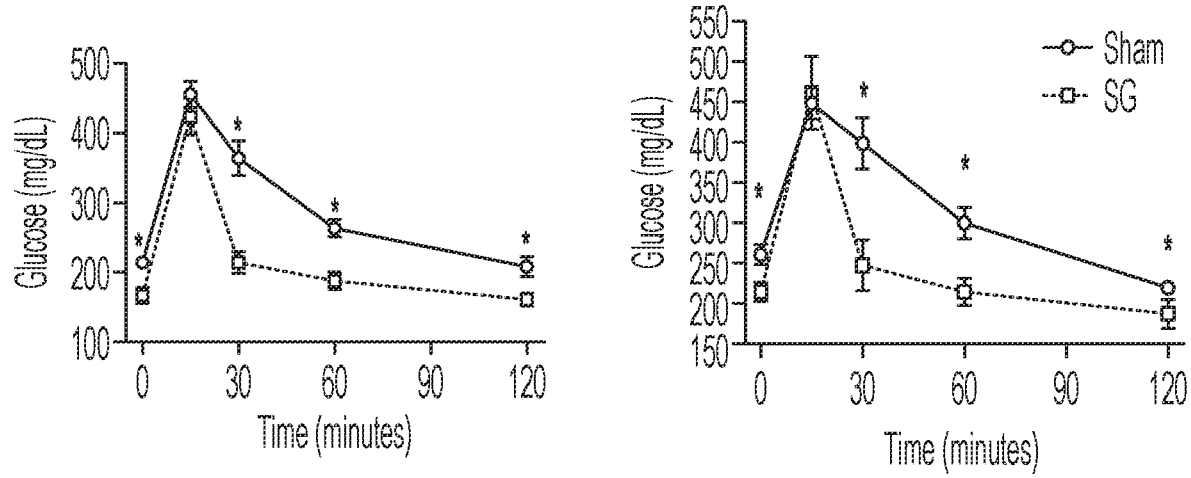
FIG. 1A shows the glucose levels from sham and sleeve gastrectomy (SG) mice following a glucose tolerance test.

The compositions and methods described herein are related, in part, to the discovery that cholic acid-7 sulfate is increased in subjects following bariatric surgery and ameliorates the symptoms of diabetes. Cholic acid-7 sulfate is a TGR5 agonist and induces GLP-1 secretion in vivo and in vitro.

Methods of Treatment and Uses

As generally described herein, provided is a method of treating or preventing diabetes, the method comprising administering to a subject in need thereof an agent that increases the level of cholic acid-7-sulfate in the subject. In one embodiment, the agent is cholic acid-7-sulfate. In one embodiment, the agent is a TGR5 agonist. In one embodiment, the TGR5 agonist is cholic acid-7-sulfate.

In one embodiment, the TGR5 agonist induces GLP-1 secretion from a target cell. In some embodiments, the activity of TGR5 is increased by at least 50%, at least 60%, at least 70%, at least 80%, at least 90%, or more as compared to a control. In some embodiments, the secretion of GLP1 is increased by at least 50%, at least 60%, at least 70%, at least 80%, at least 90%, or more as compared to a control.

In one embodiment, the agent is selected from the group consisting of a small molecule, an antibody, a peptide, a genome editing system, an antisense oligonucleotide, and an RNAi.

In some embodiments, the agent is a vector that encodes the agent. In one embodiment, the vector is non-integrative or integrative. In one embodiment, the vector is a viral vector.

In one embodiment, the agent is formulated with a pharmaceutical composition.

In one embodiment, the pharmaceutical composition is formulated to restrict delivery of an agent to the gastrointestinal tract of the subject.

In one embodiment, the diabetes is type I, type II, neonatal, or maturity onset diabetes in the young.

In one embodiment, the administering reduces glucose levels in the serum of a subject.

In one embodiment, wherein the subject is a mammal.

In one embodiment, the mammal is a human. In certain embodiments, the human is an adult human.

In one embodiment, the target cell is an enteroendocrine cell, an epithelial cell, an L-cell, or a neuron. In certain embodiments, the target cell is an immune cell, leukocyte, muscle cell, or an adipocyte.

In one aspect, described herein is a composition comprising an agent that increases the level of cholic acid-7-sulfate in a subject.

In one embodiment, wherein the agent is cholic acid-7-sulfate.

In one embodiment, the composition is formulated for treating or preventing diabetes.

In one embodiment, the composition further comprises a pharmaceutically acceptable carrier or excipient.

In one embodiment, the carrier or excipient restricts delivery of the composition to the gastrointestinal tract.

In one aspect, described herein is a method for treating or preventing diabetes, the method comprising administering to a subject in need thereof a genetically engineered microorganism or population thereof, that expresses an agent that increases the level of cholic acid-7-sulfate.

In one embodiment, the genetically engineered microorganism is a bacterium.

In one aspect, described herein is a method for treating or preventing diabetes, the method comprising administering to a subject in need thereof a genetically engineered microorganism or population thereof, that secretes cholic acid-7-sulfate.

In one embodiment, the genetically engineered microorganism is a bacterium.

The present disclosure contemplates using cholic acid-7-sulfate for the treatment of diabetes and/or obesity.

Thus, as generally described herein, provided is a method of treating diabetes and/or obesity comprising administering an effective amount of cholic acid-7-sulfate, or a pharmaceutically acceptable salt thereof, to a subject in need thereof. Such a method can be conducted in vivo (i.e., by administration to a subject). Treating, as used herein, encompasses therapeutic treatment and prophylactic treatment.

In some embodiments, the diabetes is type I diabetes, type II diabetes, neonatal diabetes, maturity onset diabetes in the young, or gestational diabetes.

In some embodiments, the diabetes is type II diabetes.

Diabetes can cause many complications. Acute complications (e.g., hypoglycemia, ketoacidosis, or nonketotic hyperosmolar coma) may occur if the disease is not adequately controlled. Serious long-term complications (i.e., chronic side effects) include cardiovascular disease (doubled risk), inflammatory diseases, chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation.

In some embodiments, the diabetes caused by obesity. In one aspect, provided herein is a method of treating obesity in a subject. The term "obesity" refers to excess fat in the body. Obesity can be determined by any measure accepted and utilized by those of skill in the art. Currently, an accepted measure of obesity is body mass index (BMI), which is a measure of body weight in kilograms relative to the square of height in meters. Generally, for an adult over age 20, a BMI between about 18.5 and 24.9 is considered normal, a BMI between about 25.0 and 29.9 is considered overweight, a BMI at or above about 30.0 is considered obese, and a BMI at or above about 40 is considered morbidly obese. (See, e.g., Gallagher et al. (2000) *Am J Clin Nutr* 72:694-701.) These BMI ranges are based on the effect of body weight on increased risk for disease. Some common conditions related to high BMI and obesity include cardiovascular disease, high blood pressure (i.e., hypertension), osteoarthritis, cancer, and diabetes. Although BMI correlates with body fat, the relation between BMI and actual body fat differs with age and gender. For example, women are more likely to have a higher percent of body fat than men for the same BMI. Furthermore, the BMI threshold that separates normal, overweight, and obese can vary, e.g., with age, gender, ethnicity, fitness, and body type, amongst other factors. In some embodiments, a subject with obesity can be a subject with a body mass index of at least about 25 kg/m$^2$ prior to administration of a treatment as described herein. In some embodiments, a subject with obesity can be a subject with a body mass index of at least about 30 kg/m$^2$ prior to administration of a treatment, compound, or agent as described herein.

In one aspect, provided herein is a method of treating an inflammatory disease in a subject. As used herein, the term "inflammation" or "inflamed" or "inflammatory" refers to activation or recruitment of the immune system or immune cells (e.g., T cells, B cells, macrophages). A tissue that has inflammation can become reddened, white, swollen, hot, painful, exhibit a loss of function, or have a film or mucus. Methods of identifying inflammation are well known in the art. Inflammation generally occurs following injury or infection by a microorganism.

In certain embodiments, the inflammatory disease is Crohn's disease. In certain embodiments, the inflammatory disease is ulcerative colitis. In certain embodiments, the inflammatory disease is pancreatitis. In certain embodiments, the inflammatory disease is hepatitis. In certain embodiments, the inflammatory disease is appendicitis. In certain embodiments, the inflammatory disease is gastritis. In certain embodiments, the inflammatory disease is diverticulitis. In certain embodiments, the inflammatory disease is celiac disease. In certain embodiments, the inflammatory disease is food intolerance. In certain embodiments, the inflammatory disease is enteritis. In certain embodiments, the inflammatory disease is ulcer. In certain embodiments, the inflammatory disease is gastroesophageal reflux disease (GERD). In certain embodiments, the inflammatory disease is psoriatic arthritis. In certain embodiments, the inflammatory disease is psoriasis. In certain embodiments, the inflammatory disease is rheumatoid arthritis.

In some embodiments, the inflammatory disease is an intestinal inflammatory disease. In certain embodiments, the inflammatory disease is associated with inflammation of the gastrointestinal tract. In certain embodiments, the inflammatory disease is selected from the group consisting of: Crohn's disease, inflammatory bowel disease, ulcerative colitis, pancreatitis, hepatitis, appendicitis, gastritis, diverticulitis, celiac disease, food intolerance, enteritis, ulcer, and gastroesophageal reflux disease (GERD), psoriatic arthritis, psoriasis, and rheumatoid arthritis.

In certain embodiments, the inflammatory disease is an inflammatory bowel disease. In certain embodiments, the inflammatory bowel disease is Crohn's disease. In certain embodiments, the inflammatory bowel disease is ulcerative colitis.

In certain embodiments, the inflammatory disease is an autoimmune disease. In certain embodiments, the autoimmune disease is celiac disease.

In certain embodiments, the effective amount is a therapeutically effective amount. For example, in certain embodiments, the method slows the progression of diabetes and/or obesity in the subject. In certain embodiments, the method improves the condition of the subject suffering from diabetes and/or obesity.

In certain embodiments, the effective amount is a prophylactically effective amount. For example, in certain embodiments, the method prevents or reduces the likelihood of obesity and/or diabetes, e.g., in certain embodiments, the method comprises administering CA7S to a subject in need thereof in an amount sufficient to prevent or reduce the likelihood of obesity and/or diabetes. In certain embodiments, the subject is at risk of obesity and/or diabetes.

As generally described herein, further provided is a method of increasing the amount of cholic acid-7-sulfate in a subject comprising administering an effective amount of cholic acid-7-sulfate, or a pharmaceutically acceptable salt thereof, to a subject in need thereof. Such a method can be conducted in vivo (i.e., by administration to a subject).

As generally described herein, further provided is a method of increasing the activity of TGR5 comprising administering an effective amount of cholic acid-7-sulfate, or a pharmaceutically acceptable salt thereof, to a subject in need thereof. Such a method can be conducted in vivo (i.e., by administration to a subject).

As generally described herein, further provided is a method of increasing GLP-1 secretion in a subject comprising administering an effective amount of cholic acid-7-sulfate, or a pharmaceutically acceptable salt thereof, to a subject in need thereof. Such a method can be conducted in vivo (i.e., by administration to a subject).

Pharmaceutical Compositions and Administration

The present disclosure provides pharmaceutical compositions comprising cholic acid-7-sulfate, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the cholic acid-7-sulfate into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of cholic acid-7-sulfate. The amount of cholic acid-7-sulfate is generally equal to the dosage of cholic acid-7-sulfate which would be administered to a subject and/or a convenient fraction of such a dosage such as, for example, one-half or one-third of such a dosage.

Relative amounts of cholic acid-7-sulfate, the pharmaceutically acceptable excipient, and/or any additional ingredients in a pharmaceutical composition will vary, depending upon the identity, size, and/or condition of the subject treated and further depending upon the route by which the composition is to be administered. By way of example, the composition may comprise between 0.1% and 100% (w/w) cholic acid-7-sulfate.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to cholic acid-7-sulfate, the liquid dosage forms may comprise inert diluents commonly used in the art such as, for example, water or other solvents, solubilizing agents, and emulsifiers, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates are mixed with solubilizing agents, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium.

Solid dosage forms for oral administration include capsules, tablets, pills, powders, and granules. In such solid dosage forms, the cholic acid-7-sulfate is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Dosage forms for topical and/or transdermal administration of cholic acid-7-sulfate may include ointments, pastes, creams, lotions, gels, powders, solutions, sprays, inhalants and/or patches. Generally, the cholic acid-7-sulfate is admixed under sterile conditions with a pharmaceutically acceptable carrier and/or any needed preservatives and/or buffers as can be required.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Cholic acid-7-sulfate may be formulated in dosage unit form for ease of administration and uniformity of dosage. It will be understood, however, that the total daily amount of CA7S will be decided by the attending physician within the scope of sound medical judgment. The specific therapeutically effective dose level for any particular subject will depend upon a variety of factors including the disease, disorder, or condition being treated and the severity of the disorder; the specific composition employed; the age, body weight, general health, sex and diet of the subject; the time of administration, route of administration, and rate of excretion of the specific compound employed; the duration of the treatment; drugs used in combination or coincidental with CA7S; and like factors well known in the medical arts.

Cholic acid-7-sulfate and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general, the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

An effective amount of cholic acid-7-sulfate may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of CA7S. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of CA7S.

It will be also appreciated that cholic acid-7-sulfate or a composition comprising CA7S, as described herein, can be administered in combination with one or more additional therapeutically active agents. CA7S or a composition comprising CA7S can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of CA7S with the additional therapeutically active agent and/or the desired therapeutic effect to be achieved. In general, it is expected that additional therapeutically active agents utilized in combination be utilized at levels that do not exceed the levels at which they are utilized individually. In certain embodiments, the levels utilized in combination will be lower than those utilized individually.

In certain embodiments, the additional therapeutic agent is an anti-diabetic agent. In certain embodiments, the anti-diabetic agent is selected from the group consisting of insulin, an insulin analog, nateglinide, repaglinide, metformin, thiazolinediones, glitazones such as troglitazone, pioglitazone and rosiglitazone, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride and gliclazide.

In certain embodiments, the additional pharmaceutical agent is a dipeptidyl peptidase 4 (DPP-4) inhibitor (e.g., sitagliptin, linagliptin, alogliptin, saxagliptin, vildagliptin).

Also provided herein are uses for cholic acid-7-sulfate in treating or preventing disease (e.g., diabetes, obesity) in a subject in need thereof. In certain embodiments, provided herein is cholic acid-7-sulfate, or a composition comprising CA7S, for use in treating or preventing diabetes in a subject. In certain embodiments, provided herein is cholic acid-7-sulfate, or a composition comprising CA7S, for use in treating or preventing obesity in a subject.

Also encompassed by this disclosure are kits (e.g., pharmaceutical packs). The kits provided may comprise a pharmaceutical composition, as described herein, or CA7S and a container (e.g., a vial, ampule, bottle, syringe, and/or dispenser package, or other suitable container). In certain embodiments, provided kits may optionally further include a second container comprising a pharmaceutical excipient for dilution or suspension of a pharmaceutical composition or CA7S. In certain embodiments, the pharmaceutical composition or CA7S provided in the container and the second container are combined to form one unit dosage form.

EXAMPLES

In order that the invention described herein may be more fully understood, the following examples are set forth. The synthetic and biological examples described in this application are offered to illustrate the compounds (e.g., cholic acid-7-sulfate), pharmaceutical compositions, uses, and methods provided herein and are not to be construed in any way as limiting their scope.

General Procedures

Animals. Diet induced obese (DIO), male, C57Bl/6J mice were purchased from Jackson Laboratory (Bar Harbor, ME) at 11-16 weeks of age. They were housed under standard conditions in a climate-controlled environment with 12 hour light and dark cycles and reared on a high fat diet (HFD, 60% Kcal fat; RD12492; Research Diets, NJ). They were allowed to acclimate for at least 1 week prior to undergoing any procedures. All animals were cared for according to guidelines set forth by the American Association for Laboratory Animal Science. All procedures were approved by the Institutional Animal Care and Use Committee.

Sleeve gastrectomy (SG) and sham procedures. 11-week-old DIG mice were purchased and housed as described above. Mice were weight-matched into two groups and either underwent SG or sham operation. SG was performed through a 1.5 cm midline laparotomy under isoflurane anesthesia. The stomach was gently dissected free from its surrounding attachments, the vessels between the spleen and stomach (short gastric vessels) were divided, and a tubular stomach was created by removing 80% of the glandular and 100% of the non-glandular stomach with a linear-cutting surgical stapler. Sham operation consisted of a similar laparotomy, stomach dissection, ligation of short gastric vessels, and manipulation of the stomach along the staple line equivalent. Mice were then individually housed thereafter to allow for monitoring of food intake, weight, and behavior. SG and Sham mice were maintained on Recovery Gel Diet (Clear $H_2O$, Westbrook, ME) from 1 day prior through 6 days after surgery and then were restarted on HFD on the morning of post-operative day (POD) 7. Mice were sacrificed 5-7 weeks post-surgery.

Functional glucose testing. After a 4 hour fast (8 am to noon), intraperitoneal glucose tolerance testing (IPGTT) and insulin tolerance testing (ITT) were performed at post-operative week 4 and 5, respectively. During IPGTT, mice received 2 mg/g of intraperitoneal D-Glucose (Sigma-Aldrich, St. Louis, MO) and serum glucose levels were measured from the tail vein at 15, 30, 60, and 120 min with a OneTouch Glucometer (Life technologies, San Diego, CA). ITT was performed by intraperitoneal instillation of 0.6u/kg of regular human insulin (Eli Lily and Company, Indianapolis, IN) and measurement of serum glucose levels at 15, 30, and 60 min. Baseline glucose was measured for each set prior to medication administration.

Body weight and food intake measurements. Mice were individually housed and weighed daily for the first post-operative week and then twice weekly until sacrifice. Food intake was measured twice weekly and daily food intake was calculated by averaging the grams eaten per day over the preceding days. Note that food intake measurements were started on POD 10 as animals were transitioned from Gel Diet to high fat diet on the morning of POD 7.

Bile acid analysis. Bile acid analyses were performed using a previously reported method (Yao, L. et al. eLife 2018, 7, 675).

Reagents. Stock solutions of all bile acids were prepared by dissolving the compounds in molecular biology grade DMSO (VWR International, Radnor, PA). These solutions were used to establish standard curves. CA7S was purchased from (Caymen Chemicals, Ann Arbor, MI. Cat. No. 9002532). Glycocholic acid (GCA) (Sigma) was used as the internal standard for measurements in mouse tissues. HPLC grade solvents were used for preparing and running UPLC-MS samples.

Extraction. Cecal, liver, and human fecal samples (approximately 50 mg each) and mouse portal veins were pre-weighed in lysis tubes containing ceramic beads (Precellys lysing kit tough micro-organism lysing VK05 tubes for cecal, fecal samples, and portal veins; tissue homogenizing CIKMix tubes for liver samples; Bertin technologies, Montigny-le-Bretonneux, France). 400p L of methanol containing 10 µM internal standard (GCA) was added and the tubes were homogenized in a MagNA Lyser (6000 speed for 90 s*2, 7000 speed for 60 s). 50 µl of mouse serum was collected in Eppendorf tubes, followed by addition of 50 µL of methanol containing 10 µM internal standard (GCA). After vortexing for 1 min, the sample was cooled to −20° C. for 20 min. All methanol-extracted tissue samples were centrifuged at 4° C. for 30 min at 15,000 rpm. The supernatant was diluted 1:1 in 50% methanol/water and centrifuged again at 4° C. for 30 min at 15000 rpm. The supernatant was transferred into mass spec vials and injected into the UPLC-MS.

UPLC-MS. Samples were injected onto a Phenomenex 1L7 µm, C18 100 Å, 100×21 mm LC column at room temperature and eluted using a 30 min gradient of 75% A to 100% B (A=water+0.05% formic acid; B=acetone+0.05% formic acid) at a flow rate of 0.350 mL/min. Samples were analyzed using an Agilent Technologies 12990 Infinity 11 UPLC system coupled online to an Agilent Technologies 6120 Quadrupole LC/MS spectrometer in negative electrospray mode with a scan range of 350-550 m/z (MSD settings: fragmentor—250, gain—3.00, threshold—150, Step size—0.10, speed (u/sec)—743). Capillary voltage was 4500 V, drying gas temperature was 300° C., and drying gas flow was 3 L/min. Analytes were identified according to their mass and retention time. For quantification of the analytes, standard curves were obtained using known bile acids, and then each analyte was quantified based on the standard curve and normalized based on the internal standard. The limit of detection for CA7S is 0.05 picomol/µL. Note that CA7S and cholic acid-3-sulfate can be distinguished based on retention time using this UPLC-MS method.

Figure 1B:
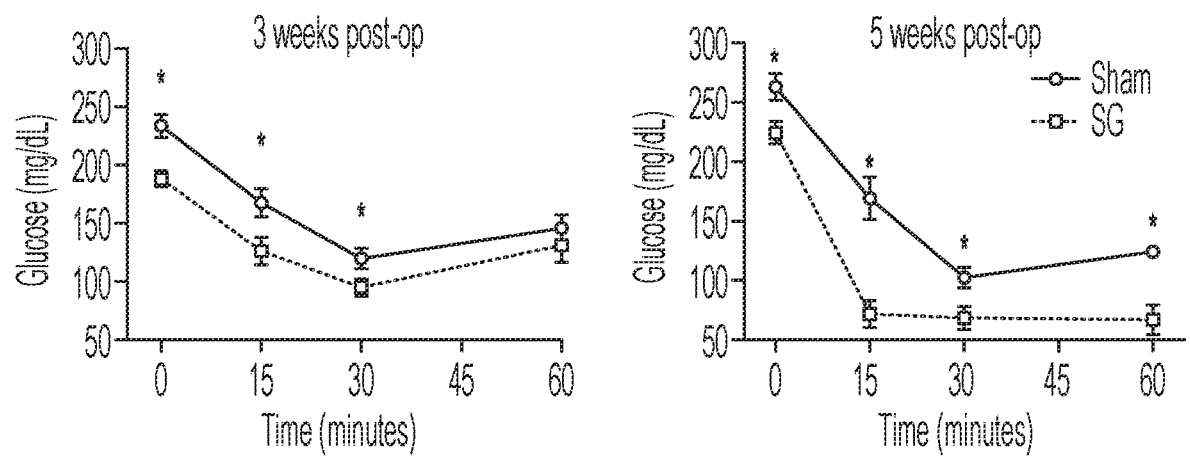
FIG. 1B shows sham and SG mice glucose levels following insulin tolerance tests. High fat diet (HFD) mice post-sleeve show improved glucose tolerance and insulin sensitivity.

Purification of CA7S. Extracted cecal contents from 11 SG mice (same shown in FIG. 1) were pooled to provide sufficient material for purification. Pooled extract was purified via MS-guided HPLC of m/z 487 using a Luna RP C18 semi-preparative column and water and acetonitrile with 0.1% formic acid as an additive.

NMR Spectroscopy. CA7S and purified m/z 487 (<1 mg) were dissolved in 250 µL DMSO-d6. Nuclear magnetic resonance (NMR) spectra were acquired on a Varian INOVA 500 MHz and are referenced internally according to residual solvent signals (DMSO to 2.50, HOD to 3.33).

Cell culture. NCI-H716 cells and Caco-2 cells were obtained from American Type Culture Collection (Manassas, VA). HEK-293T cells were a kind gift from the Blacklow lab (BCMP, HMS). Caco-2 and HEK-293T cells were maintained in Minimum Essential Medium (MEM) with GlutaMAX and Earle's Salts (Gibco, Life Technologies, UK). NCI-H716 cells were maintained in RPMI 1640 with L-glutamine (GenClone, San Diego, CA). All cell culture media were supplemented with 10% fetal bovine serum (FBS), 100 units/ml penicillin, and 100 µg/ml streptomycin (GenClone). Cells were grown in FBS- and antibiotic-supplemented 'complete' media at 37° C. in an atmosphere of 5% CO2.

In vitro bile acid treatments. NCI-H716 cells were seeded in cell culture plates coated with Matrigel (Corning, NY. Cat. No. 356234) diluted in Hank's Balanced Salt Solution (HBSS, Gibco) according to manufacturer's instructions. The cells were allowed to grow for 2 days in complete RPMI media. On the day of the treatment, cells were rinsed gently with low serum (0.5% FBS) RPMI 1640 medium without antibiotics. Bile acids cholic acid-7-sulfate (CA7S), cholic acid (CA) (Sigma) and taurodeoxycholic acid (TDCA) (Sigma) were diluted in dimethyl sulfoxide (DMSO, VWR International) and added to cells in the low serum media (0.5% FBS, RPMI 1640) without antibiotics. The concentration of DMSO was kept constant throughout the treatments and used as a negative control. Cells were incubated at 37° C. in an atmosphere of 5% CO2 for 2 hours. After the incubation period, cell culture media was collected in Eppendorf tubes containing 1% trifluoroacetic acid (TFA, Sigma) in sterile purified water (GenClone) to make a final TFA concentration of 0.1% and frozen at −80° C. for further GLP-1 measurements. Cells on cell culture plates were placed on ice and gently washed with PBS (GenClone). Cells used for GLP-1 measurements were treated with ice-cold cell lysis solution of 1% TFA, 1N hydrochloric acid, 5% formic acid, and 1% NaCl (all from Sigma), scraped off of the Matrigel coating, and collected in lysing tubes with ceramic beads (Precellys lysing kit tough micro-organism lysing VK05 tubes). For calcium measurements, PBS was added to cells, and were collected in lysing tubes containing ceramic beads (Precellys lysing kit tough micro-organism lysing VK05 tubes). Cells were thereafter lysed in a MagNA Lyser and stored at −80° C. for further analysis. Cells used for RNA extraction were treated with TRIzol (Ambion, Life Technologies, Thermo Fisher Scientific, Waltham, Mass.) and stored at −80° C. for further analysis.

GLP-1 and Insulin measurements. Total GLP-1 peptide measurements were performed using the GLP-1 EIA Kit (Sigma, Cat. No. RAB0201) and total insulin levels were measured using the Mouse Ins1/Insulin-1 ELISA kit (Sigma, Cat. No. RAB0817) according to manufacturer's instructions. Mouse serum samples, NCI-H716 cell lysates, and cell culture media samples were stored at −80° C. and thawed on ice prior to performance ELISA assay. 20 µl of mouse serum samples were used directly in the GLP-1 ELISA assay, while 50 µl of mouse serum samples were used directly in the Insulin ELISA assay. Cell culture media were centrifuged at 12000 rpm, and the supernatant was directly used in the GLP-1 ELISA assay. Cell lysates were subjected to peptide purification using Sep Pak C18 Classic columns (Waters Corporation, Milford, MA). The column was pretreated with a solution of 0.1% TFA in 80% isopropyl alcohol (EMD Millipore) and equilibrated with 0.1% TFA in water. Cell lysates were loaded onto the column and washed with 0.1% TFA in 80% isopropyl alcohol. The peptides were eluted in 0.1% TFA in water. The eluate was concentrated by drying under vacuum and resuspended in 0.1% TFA in water. Water was used as 'blank' reading for serum GLP-1 ELISA, while 0.1% TFA in water was used as 'blank' for cell culture media and purified cell lysate ELISAs. Excess samples were stored at −80° C. for later analyses. Total GLP-1 amounts in the cell culture media (secreted) and cell lysates were calculated using a standard curve provided in the EIA kit. Percentage GLP-1 secretion was calculated as follows: % GLP-1 secretion=total GLP-1 secreted (media)/(total GLP-1 secreted (media)+total GLP-1 in cell lysates)*100. Relative GLP-1 secretion was calculated compared to DMSO control.

Plasmids and transient transfections. Human TGR5 was cloned using cDNA from human Caco-2 cells as template and a forward primer with an EcoRI restriction-site (5'-CGGAATTCGCACTTGGTCCTTGTGCTCT-3') (SEQ ID NO: 1) and a reverse primer with a XhoI-site (5'-GTCTCGAGTTAGTTCAAGTCCAGGTCGA-3') (SEQ ID NO: 2). The PCR product was cloned into the pCDNA 3.1+ plasmid (Promega Corporation, Madison, WI) and transfected at a concentration of 0.4 µg/ml of media. For luciferase reporter assays for TGR5 activation, the pGL4.29[luc2P/CRE/Hygro] plasmid (Promega Corporation), and the pGL4.74[hRluc/CMV] plasmid (Promega Corporation) were used at concentration of 2 µg/ml and 0.05 µg/ml of media respectively. All plasmids were transfected using Opti-MEM (Gibco) and Lipofectamine 2000 (Invitrogen, Life Technologies, Grand Island, NY., USA) according to manufacturer's instructions. Plasmid transfection were performed in antibiotic-free media (MEM for HEK293T and RPMI for Matrigel-attached NCI-H716 cells) with 10% FBS. After overnight incubation, bile acids were added in complete media and incubated overnight. Cells were harvested the next day for luciferase assay. TGR5 siRNA (Santa Cruz Biotechnology, Dallas, TX) and negative siRNA (Ambion) transfection was performed using Opti-MEM and Lipofectamine 2000 according to manufacturer's instructions. After siRNA transfection, cells were incubated in antibiotic- and serum-free media (RPMI for Matrigel-attached NCI-H716 cells) for 24 hours. The next day, the media was replaced by complete media and incubated overnight. Bile acids were added 48 hours post-siRNA transfection in complete media and incubated overnight. Cells were harvested the next day for luciferase assay or RNA extraction.

Luciferase reporter assay. Luminescence was measured using the Dual-Luciferase Reporter Assay System (Promega Corporation) according to manufacturer's instructions. Cells were washed gently with PBS and lysed in PLB from the kit. Matrigel-attached cells were scraped in PLB. Luminescence was measured using the SpectraMax M5 plate reader (Molecular Devices, San Jose, CA) at the ICCB-Longwood Screening Facility at Harvard Medical School. Luminescence was normalized to Renilla luciferase activity and percentage relative luminescence was calculated compared to DMSO control.

Calcium measurement. CA7S-treated NCI-H716 cells collected in PBS were used to measure intracellular calcium using the Calcium Assay Kit (Fluorometric) (Abcam, UK). Cell lysates were centrifuged at 12000 rpm, and the supernatant was directly used in the calcium assay according to manufacturer's instructions. Fluorescence was measured using the SpectraMax M5 plate reader (Molecular Devices, San Jose, CA) at the ICCB-Longwood Screening Facility at HMS. Percentage relative fluorescence was calculated compared to DMSO control.

Cell viability assay. Caco-2 cells were treated with CA7S diluted in DMSO in complete MEM media. The concentration of DMSO was kept constant and used as a negative control. Cells were incubated with CA7S overnight at 37° C. in an atmosphere of 5% CO2. The next day, cells were treated with 0.25% trypsin in HBSS (GenClone) for 10 min at 37° C. Cell viability was measured in Countess II automated cell counter (Invitrogen). Percentage relative viability was calculated compared to DMSO control.

pH stability test. Stability of CA7S in physiological pH's was determined using the Waters pH stability test. Briefly, buffers of pH 1 (0.1 M HCl), pH 7.4 (PBS) and pH 9 (a 10 mM solution of ammonium formate adjusted to pH 9 with ammonium hydroxide) (all from Sigma) were prepared. CA7S was incubated in the pH buffers overnight at 37° C. with gentle shaking (50 rpm). The next day, the CA7S solution was diluted in methanol, transferred into mass spec vials and injected into the UPLC-MS.

RNA extraction and qPCR. Cells frozen in TRIzol (Ambion) were collected in RNase-free Eppendorf tubes and vortexed for 30 seconds. Tissues were collected in Precellys tubes with ceramic beads and TRIzol, followed by homogenization in a MagNA Lyser (Roche, Switzerland). Tubes were kept on ice whenever possible. Chloroform was added (200 µl chloroform/1 ml TRIzol) and vortexed for 30 seconds. Tubes were centrifuged at 12,000 rpm for 15 min at 4° C. The clear top layer was transferred to new RNase-free Eppendorf tubes containing 2-propanol and inverted to mix (500 µl 2-propanol/1 ml TRIzol). Tubes were centrifuged at 12,000 rpm for 10 min at 4° C. The pellet was washed with 70% EtOH and centrifuged at 14,000 rpm for 5 minutes at 4° C. The RNA pellet was air-dried and resuspended in RNase-free H$_2$O (GenClone). cDNA synthesis was performed using the High Capacity cDNA Reverse Transcription Kit (Applied Biosystems, Invitrogen, Foster City, CA). qPCR was performed using the Lightcycler 480 SYBR Green I Mater (Roche, Switzerland) in a 384-well format using a LightCycler 480 System (Roche) at the ICCB-Longwood Screening Facility at Harvard Medical School. The $2^{-\Delta\Delta ct}$ method was used to calculate the relative change in gene expression. Human TGR5 gene expression were normalized to the human HPRTI (HGPRT). Mouse GLP-1R gene expression was normalized to 18S. Primer sequences were:

```
human TGR5:
Forward:
                                   (SEQ ID NO: 3)
5'-CCTAGGAAGTGCCAGTGCAG-3', Reverse:
                                   (SEQ ID NO: 4)
5'-CTTGGGTGGTAGGCAATGCT-3';

human HGPRT:
Forward:
                                   (SEQ ID NO: 5)
5'-CCTGGCGTCGTGATTAGTGA-3',
```

```
-continued
Reverse:
                                         (SEQ ID NO: 6)
5'-CGAGCAAGACGTTCAGTCCT-3';

mouse GLP-1R:
Forward:
                                         (SEQ ID NO: 7)
5'-AGGGCTTGATGGTGGCTATC-3', Reverse:
                                         (SEQ ID NO: 8)
5'-GGACACTTGAGGGGCTTCAT-3';

mouse 18S:
Forward:
                                         (SEQ ID NO: 9)
5'-ATTTGGAGCTGGAATTACCGC-3', Reverse:
                                        (SEQ ID NO: 10)
5'-CGGCTACCACATCCAAGGAA-3'.
```

In vivo enteral treatment with CA7S. 13-week-old male C57Bl/6J mice were purchased, acclimated, and housed as above. They were weight matched into two groups (p=0.88). After an overnight fast (17:00 to 0800), mice received either CA7S or PBS via direct duodenal and rectal administration. The optimal, physiologic dose of CA7S was extrapolated from the average pmol concentration of CA7S found in cecal samples from SG animals (average of 3000 pmol/mg of stool with 500 mg of stool per animal corresponds to 0.75 mg of CA7S per cecum).

Under isoflurane general anesthesia, 0.25 mg and 0.75 mg of CA7S in PBS (pH 7.2) was delivered by slow infusion (5 min) antegrade into the duodenum and retrograde into the rectum, respectively. The total volume of instillation was 2 mL (0.5 mg CA7S/mL). Control animals received similar volumes of PBS alone. 15 min post infusion, serum glucose was measured via tail vein followed by whole blood collection via cardiac puncture into K+EDTA tubes containing DPPIV inhibitor (Merck Millipore, Billerica, Mass.), Perfabloc (Sigma), and apoprotinin (Sigma). Organs were harvested for analysis. In order to account for changes in fasting times and hormonal diurnal rhythms, this experiment was carried out on four consecutive days such that only four mice were tested per day.

In vivo CA7S gavage. 16-week-old DIG mice were purchased and housed as described above. Mice were gavaged orally with 100 mg/kg CA7S from 20 mg/mL solution, or equivalent volume of PBS using 20G×38 mm gavage needle. 5 hours after CA7S/PBS administration, whole blood and intestinal segments were collected.

In vivo CA7S and OGTT. Age matched, DIG mice were kept on HFD and their blood glucose levels were monitored until average fasting glucose levels were >160 mg/dL. Animals were fasted for 4 hours on the day of the experiment. Mice were matched into two groups based on fasting glucose levels and received either 100 mg/kg CA7S from a 20 mg/ml solution or an equivalent volume of PBS by oral gavage. Three hours later, an OGTT was performed using an oral gavage of 2 mg/g oral D-glucose (Sigma-Aldrich, St. Louis, Mo.). Blood glucose levels were measured at baseline and at minutes 15, 30, 60 and 120 with a OneTouch glucometer.

Lentiviral IP injection. GLP-1R shRNA-containing lentiviral particles (LVP) were purchased from the MISSION TRC library (Sigma-Aldrich, St. Louis, Mo.). LVPs containing a mixture of three GLP-1R shRNA plasmid clones (TRCN0000004629, TRCN0000004630, and TRCN0000004633) were purchased, stored at −80° C., and thawed on ice before use. DIG mice were maintained on a HFD until average fasting glucose >160 mg/dL in a BL2 facility. Under sterile conditions, mice were injected intraperitoneally with 0.2 ml of $5\times10^5$ GLP-1R shRNA LVPs with a 27G needle (Tiscornia, G., et al. PNAS 2003, 100, 1844-1848; Blosser, W. et al. PLOS ONE 2014, 9, e96036). 72 hours after LVP injection, mice underwent CA7S/PBS gavage followed by OGTT as above. After the OGTT was completed, mice were sacrificed and their tissues were harvested. GLP-1R knock-down efficiency was measured in tissues by qPCR as described above.

Human stool collection. After obtaining institutional review board approval, we prospectively collected stool specimen from obese human subjects undergoing SG. Preoperative stool specimens were collected on the day of surgery and post-operative stool specimen were obtained from post-operative day 14 to 99 (mode 15 days; median 36 days). Specimens were snap frozen in liquid nitrogen and stored at −80° C. until bile acid analysis was performed (as above).

Example 1. Glucose and Bile Acid Profiles Post-Gastric Sleeve Surgery Mouse Model The mouse model described herein is used to study the amelioration of diabetic phenotypes post-sleeve surgery. Mice are suitable model for bariatric surgery-induced amelioration of diabetic phenotypes. High fat diet-fed mice post-sleeve show improved glucose tolerance and insulin sensitivity (FIGS. 1A and 1B) consistent with what has been observed before in humans.

Figure 2:
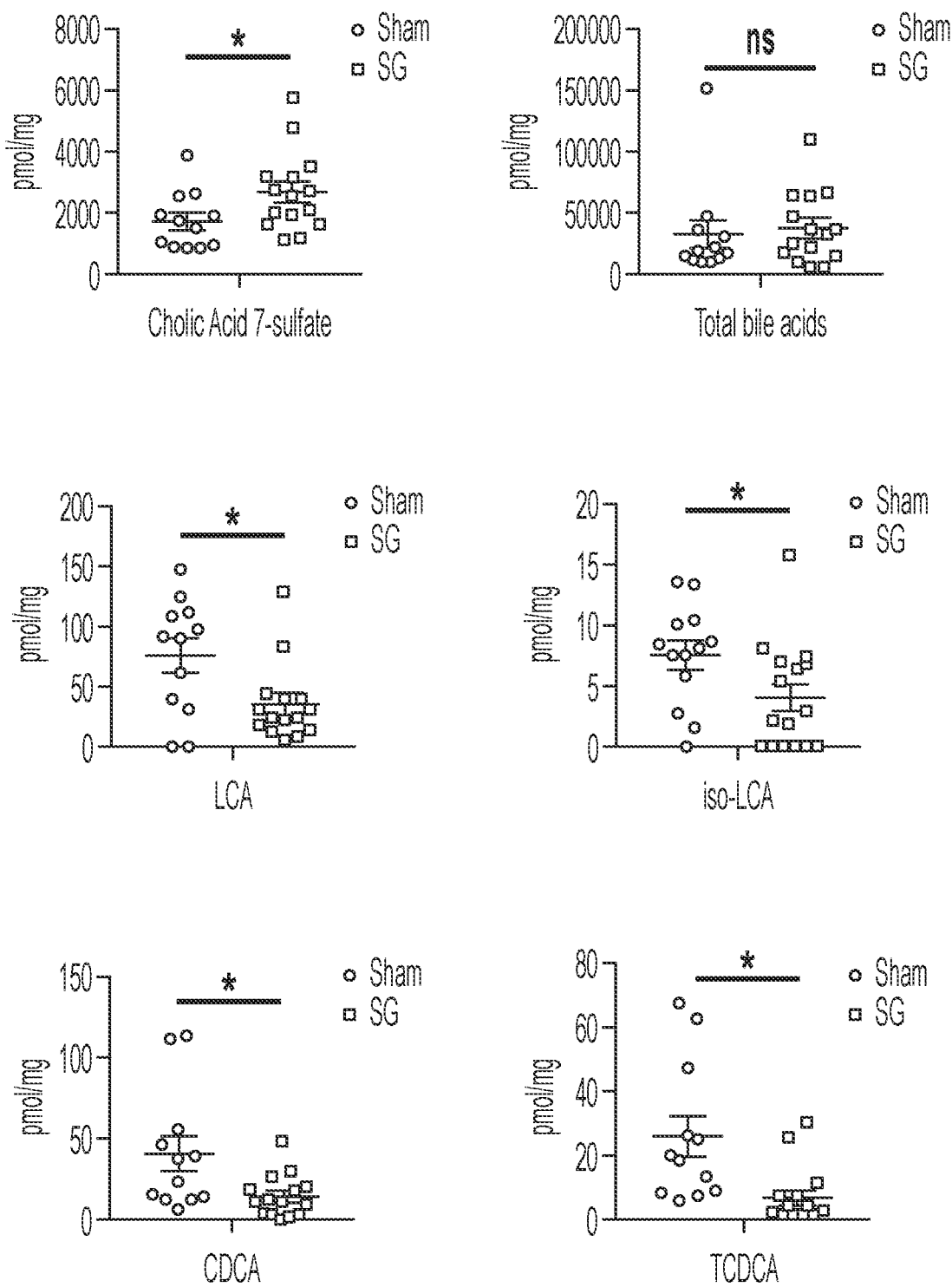
FIG. 2 shows that bile acid profiling reveals significant changes in individual bile acids including cholic acid-7-sulfate in mice post-sleeve.

Bile acid profiling was performed and revealed significant changes in individual bile acids in mice post-sleeve. Mice 6 weeks post-sleeve have higher levels of cholic acid-7-sulfate in their cecum compared to sham-operated mice (FIG. 2). It was confirmed that the molecule in the bile acid was cholic acid-7-sulfate by NMR. Furthermore, mice post-sleeve have lower levels of secondary bile acid LCA and components of the "CDCA pathway" including CDCA, TCDCA, and iso-LCA in their cecum (FIG. 2).

Figure 3:
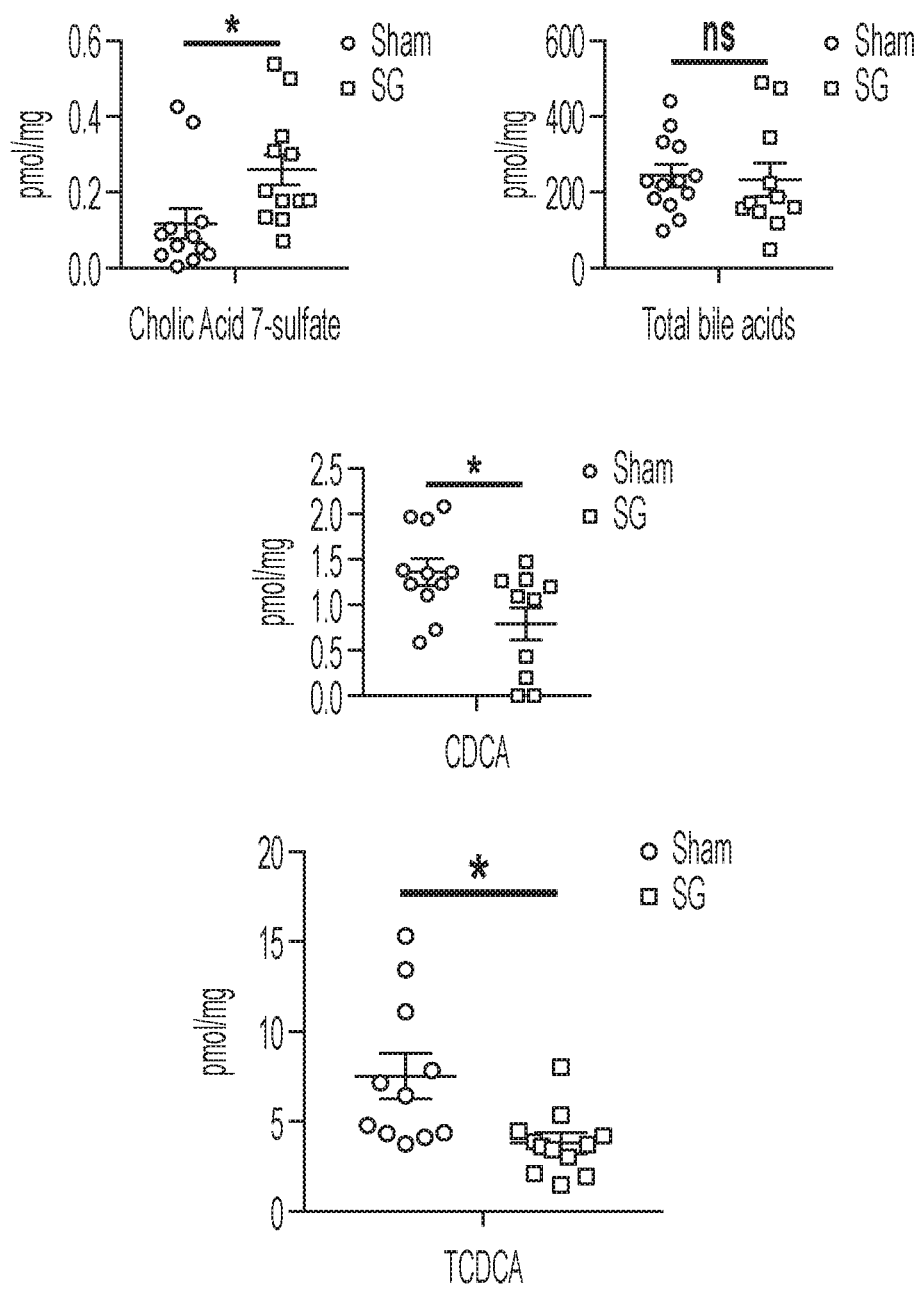
FIG. 3 shows that sleeve mice livers also showed increased cholic acid-7-sulfate, chenodeoxycholic acid (CDCA), and taurochenodeoxycholic acid (TCDCA).
Figure 7:
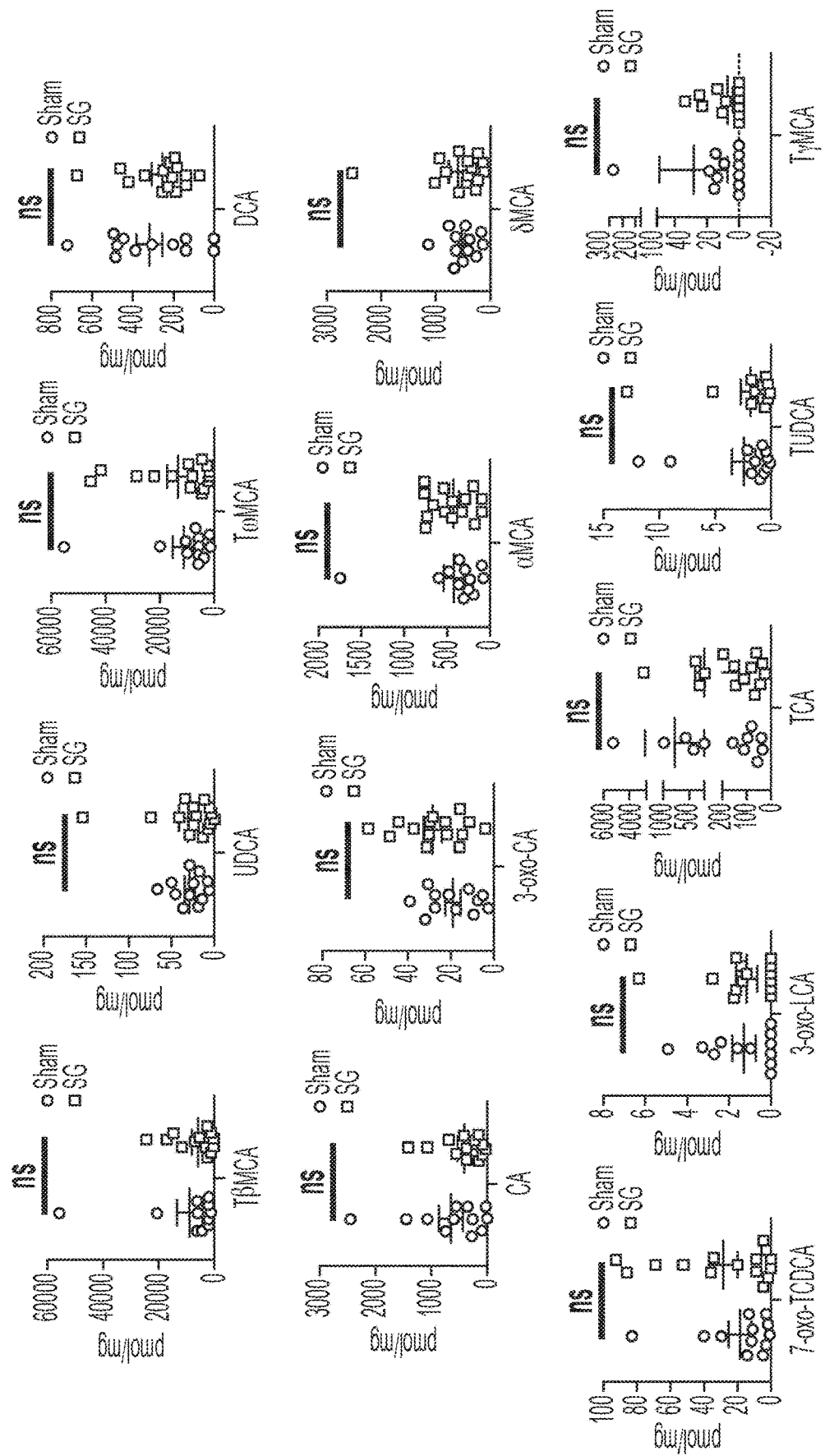
FIG. 7 shows that total bile acids and other bile acids did not differ significantly in cecum of mice operated with sleeve or sham surgery.
Figure 8:
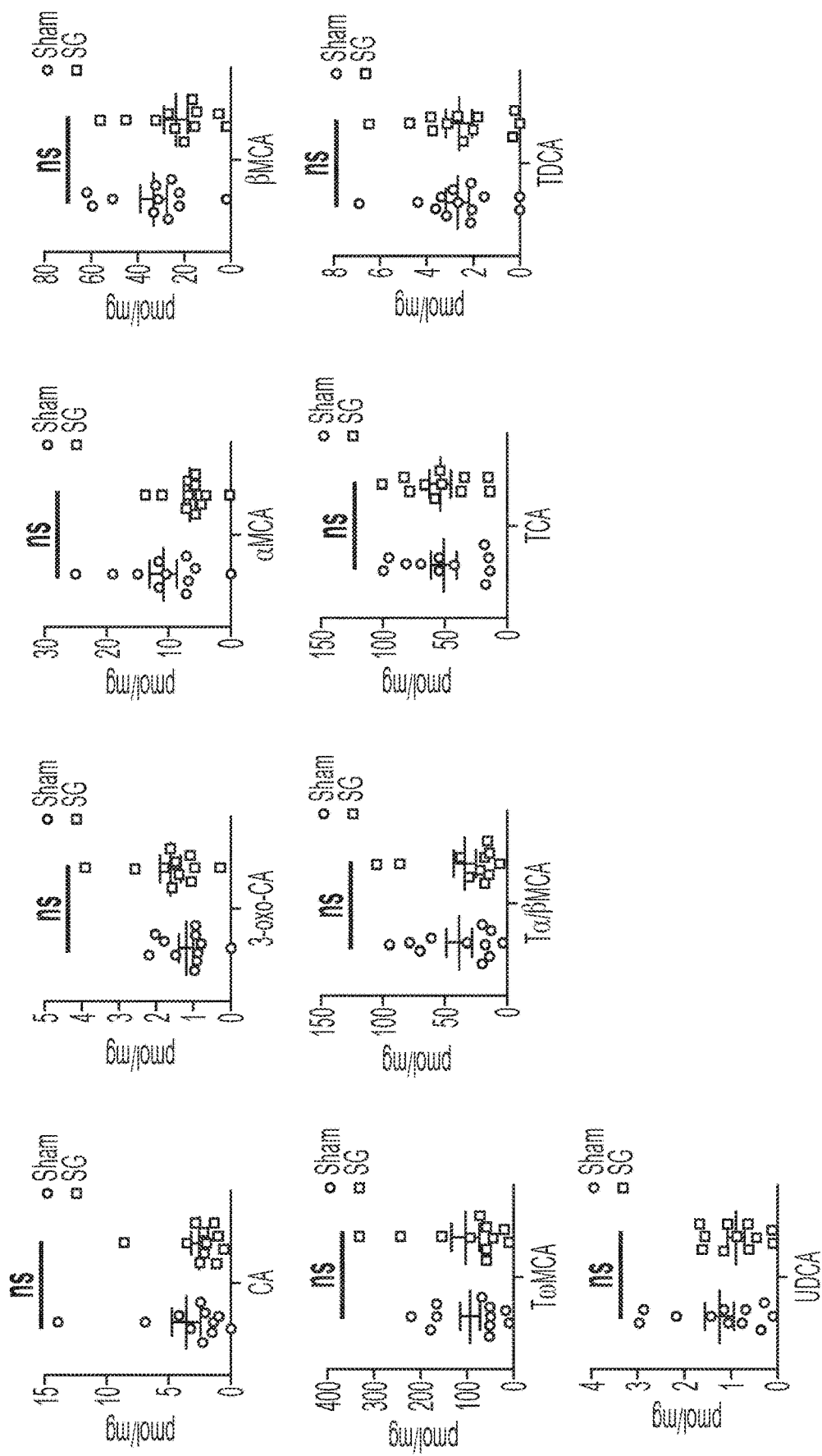
FIG. 8 shows that total bile acids and other bile acids did not differ significantly in liver of mice operated with sleeve or sham surgery.

The total bile acids and other bile acids did not differ significantly in cecum of mice operated with sleeve or sham surgery (FIG. 7). Sleeve mice livers showed increased cholic acid-7-sulfate, CDCA, and TCDCA (FIG. 3). However, total bile acids and other bile acids did not differ significantly in liver of mice operated with sleeve or sham surgery (FIG. 8).

Example 2. Increased GLP1 and TGR5 Activation with Cholic Acid-7-Sulfate

Figure 4A:
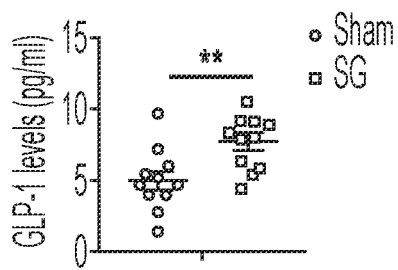
FIG. 4A shows that sleeve mice show increase in GLP-1 in systemic circulation.
Figure 4B:
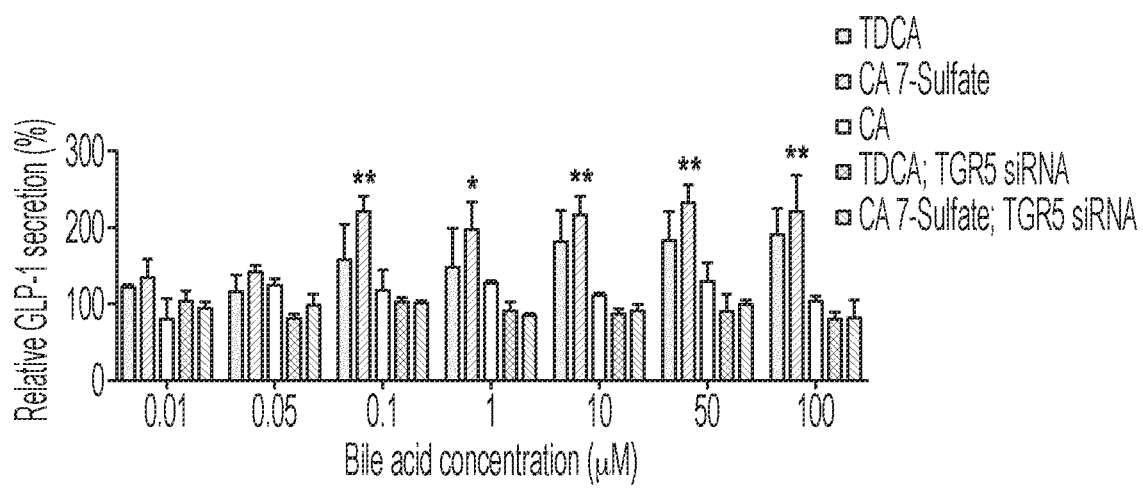
FIG. 4B shows that cholic acid-7-sulfate induces GLP-1 secretion in vitro better than the known GLP-1 inducer taurodeoxy cholic acid (TDCA), while cholic acid had no effect.

It was observed that sleeve mice show increase in GLP-1 in systemic circulation (FIG. 4A). Cholic acid-7-sulfate induces GLP-1 secretion in vitro better than the known GLP-1 inducer TDCA, while cholic acid had no effect (FIG. 4B and FIG. 9).

Figure 9A:
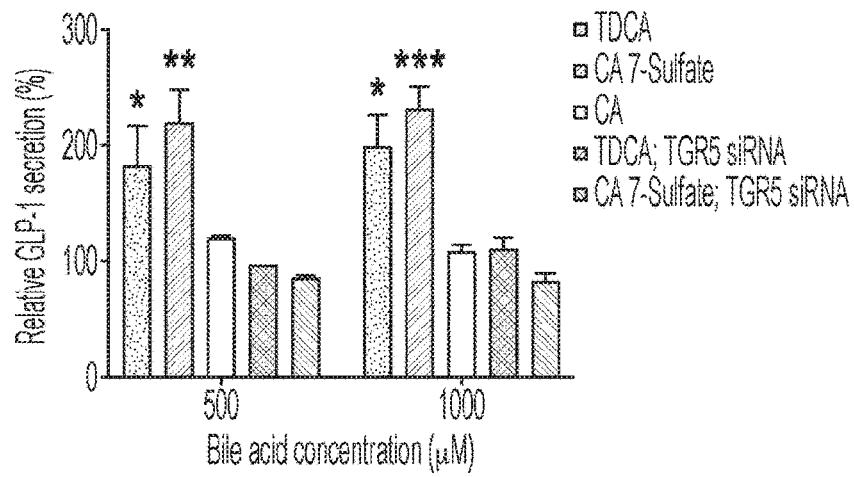
FIG. 9A shows that knockdown of TGR5 abolished GLP-1 secretion.

To identify a particular target of cholic acid-7-sulfate, it was discovered that cholic acid-7-sulfate-mediated induction of GLP-1 and requires TGR5. This was confirmed when knockdown of TGR5 abolished GLP-1 secretion (FIG. 4B and FIG. 9A). Therefore, cholic acid-7-sulfate is a TGR5 agonist and induces GLP-1 secretion in vitro.

Figures 4C, 4D:
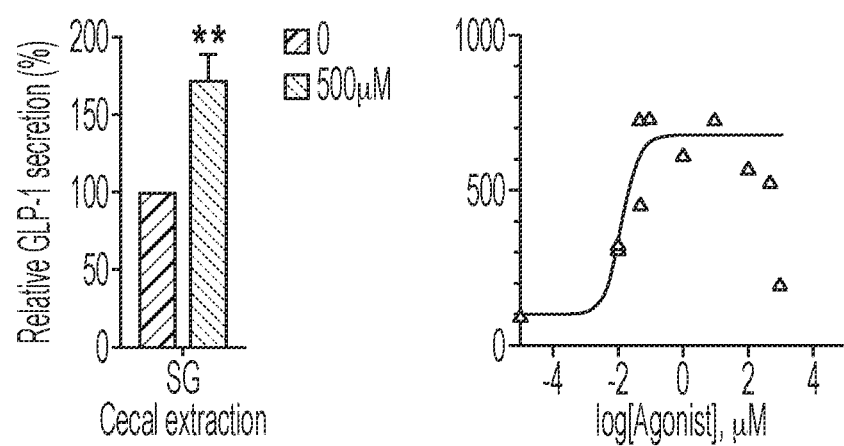
FIG. 4C shows that cholic acid-7-sulfate extracted from cecum of mice also has activity in inducing GLP-1 secretion in vitro.
FIG. 4D shows that cholic acid-7-sulfate activates TGR5 in L-cells, dose response curve shows an EC50 of 0.013 μM.
Figure 9B:
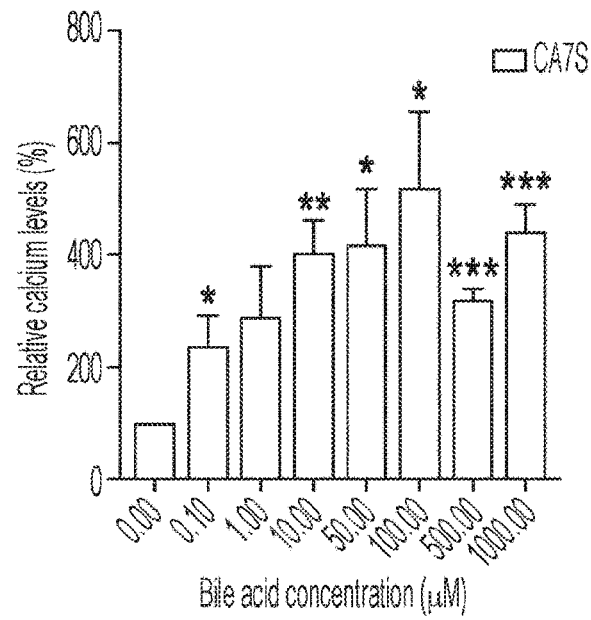
FIG. 9B shows that cholic acid-7-sulfate increases calcium levels in L-cells in vitro.
Figure 9C:
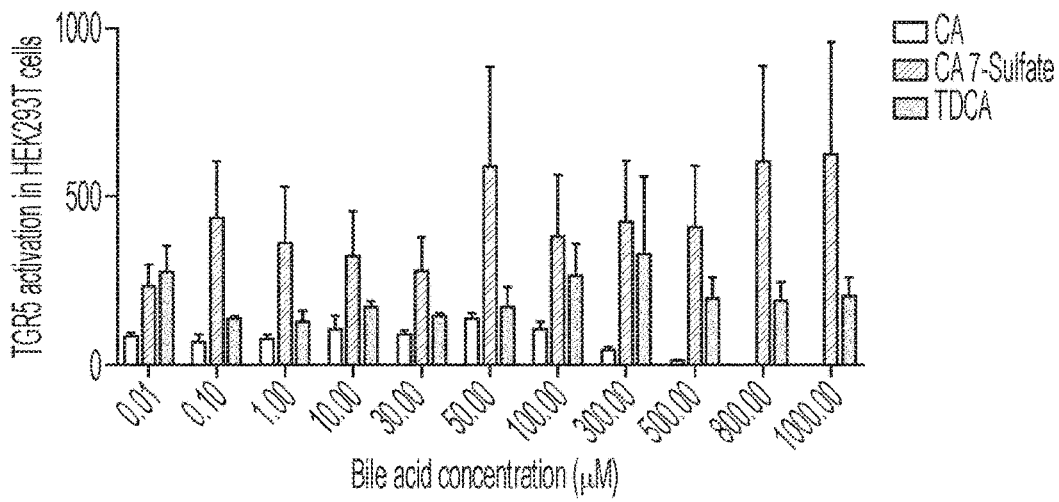
FIG. 9C shows that cholic acid-7-sulfate induces TGR5 activation in HEK293T cells.
Figure 10:
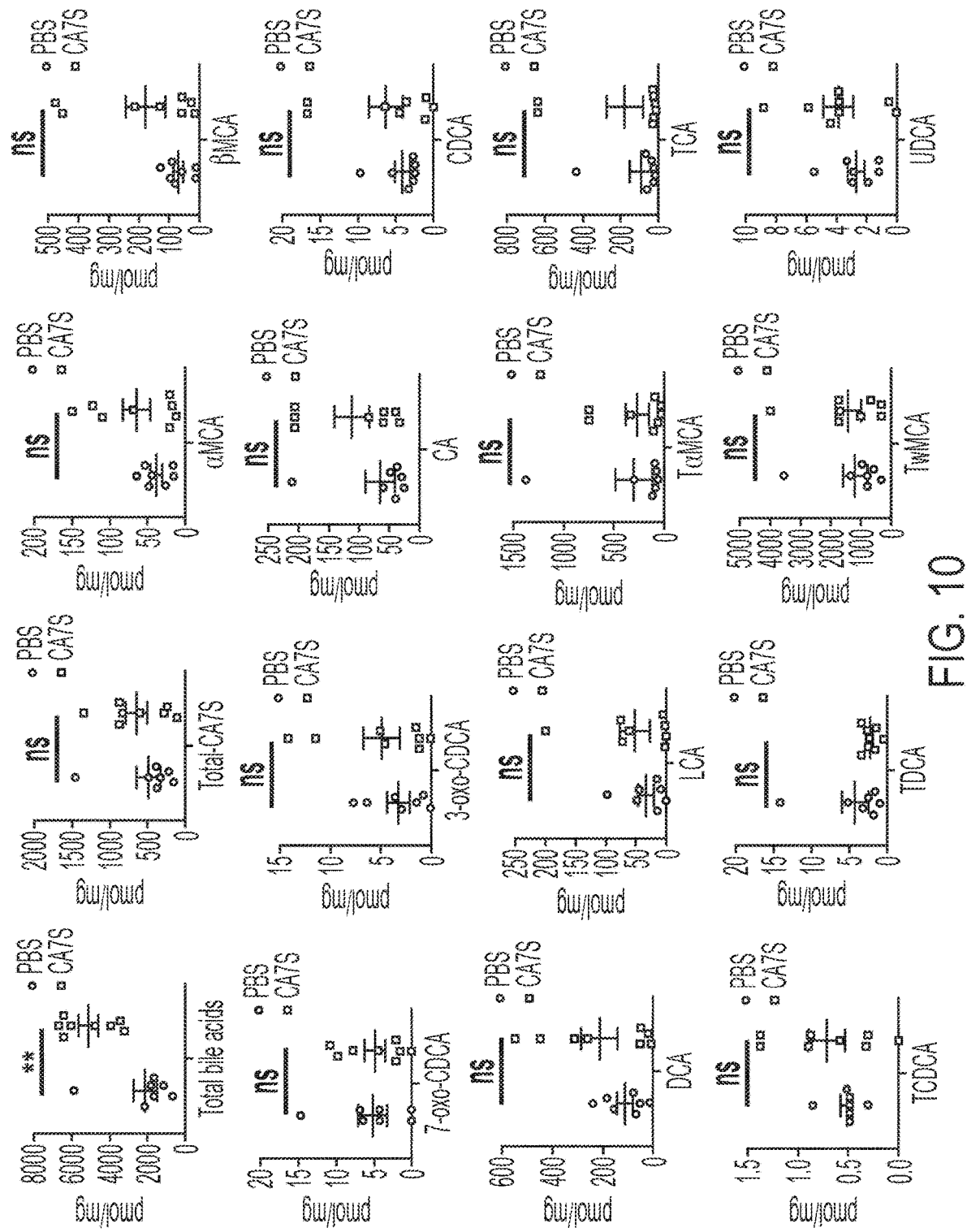
FIG. 10 shows that ectopic introduction of cholic acid-7-sulfate allowed only minor amounts to leak into systemic circulation and in the portal vein, and did not significantly affect other bile acids in the cecum, blood, or the portal vein.
Figure 11:
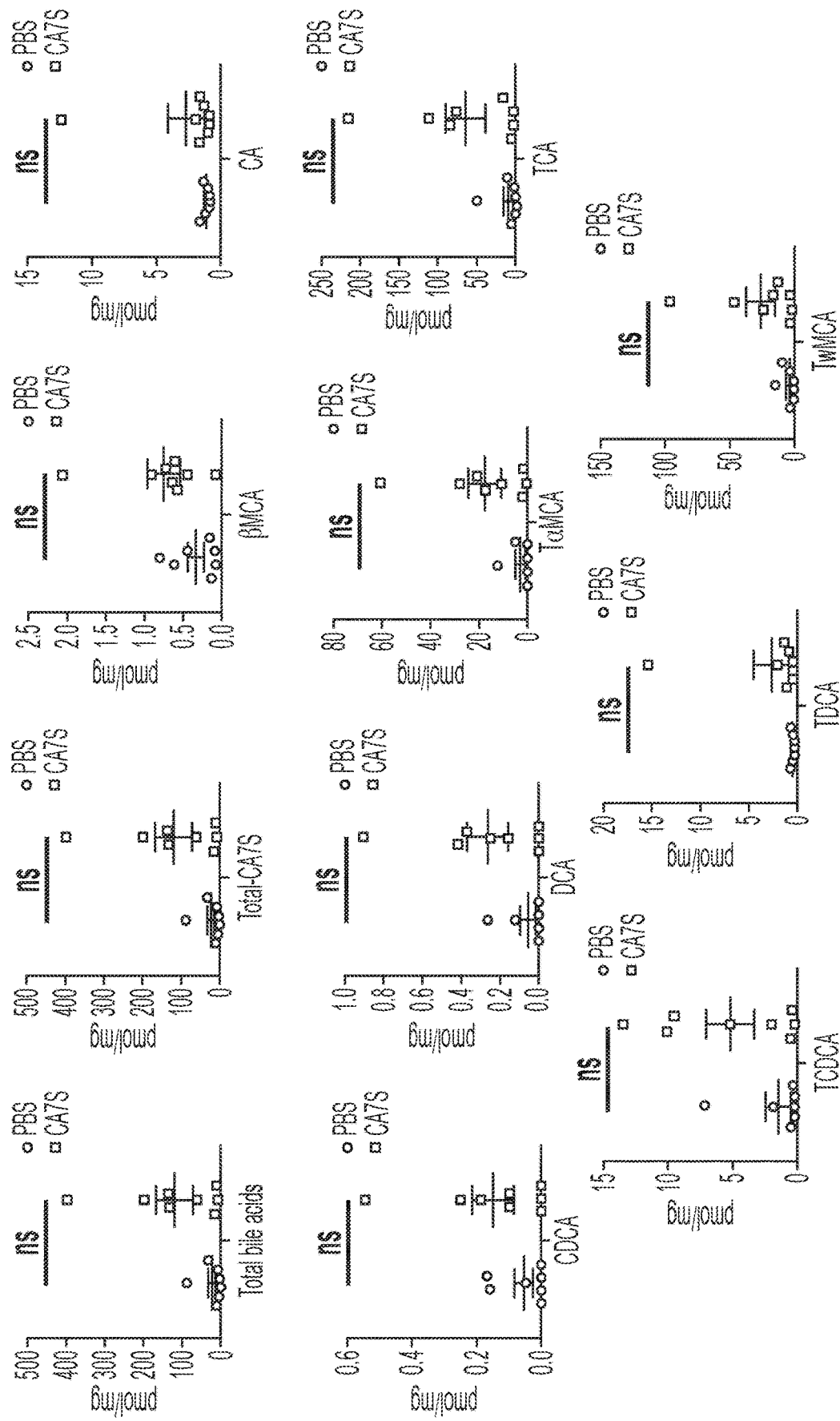
FIG. 11 shows that ectopic introduction of cholic acid-7-sulfate allowed only minor amounts to leak into systemic circulation and in the portal vein, and did not significantly affect other bile acids in the cecum, blood, or the portal vein.
Figure 12:
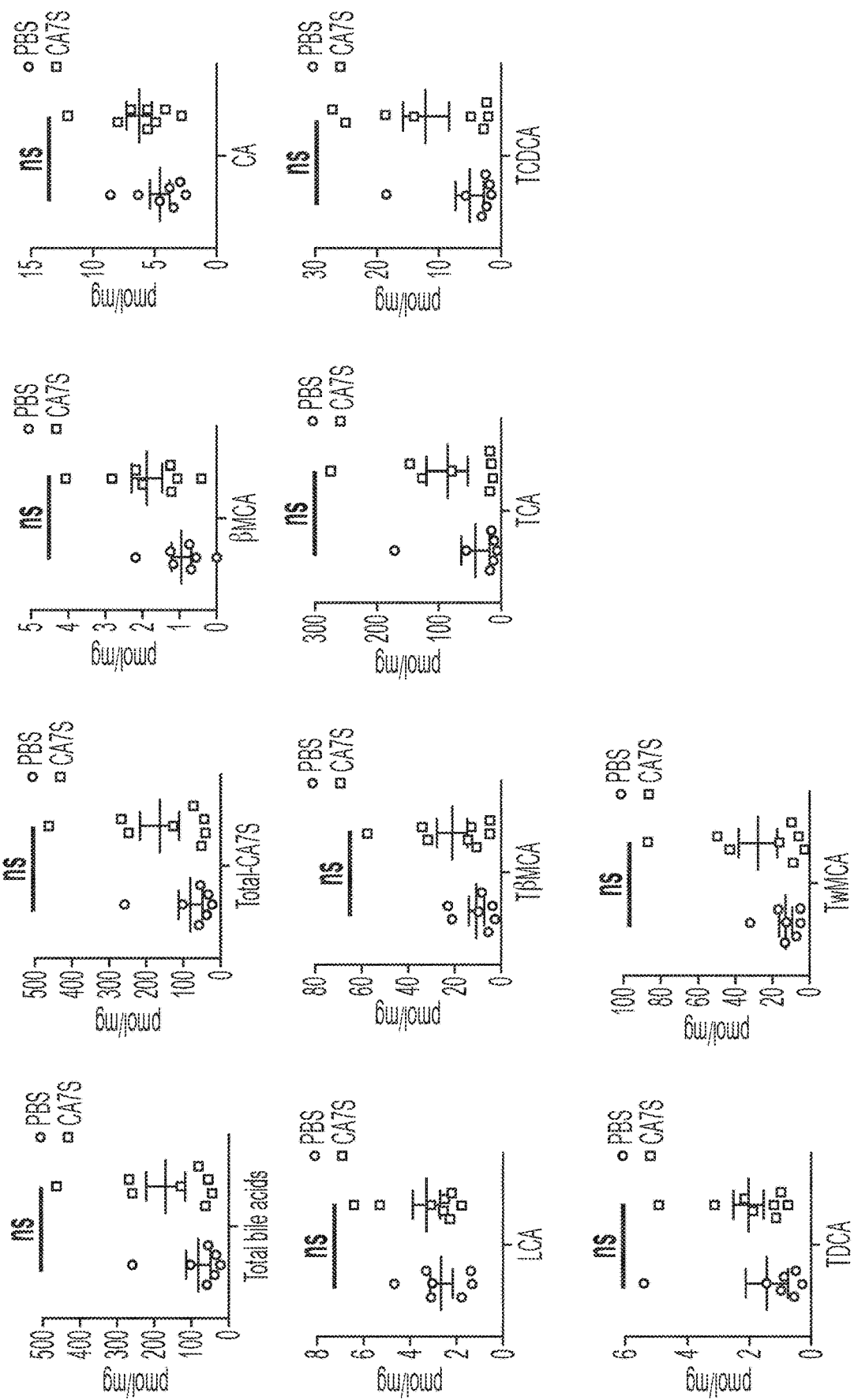
FIG. 12 shows that ectopic introduction of cholic acid-7-sulfate allowed only minor amounts to leak into systemic circulation and in the portal vein, and did not significantly affect other bile acids in the cecum, blood, or the portal vein.

To further investigate this mechanism, cholic acid-7-sulfate was extracted from cecum of mice and found to also exhibit activity inducing GLP-1 secretion in vitro (FIG. 4C). Cholic acid-7-sulfate activates TGR5 in L-cells, dose response curve shows an EC50 of 0.013 µM (FIG. 4D). Cholic acid-7-sulfate increased calcium levels in L-cells in vitro (FIG. 9B). Cholic acid-7-sulfate induces TGR5 activation in HEK293T cells (FIG. 9C).

Figure 5A:
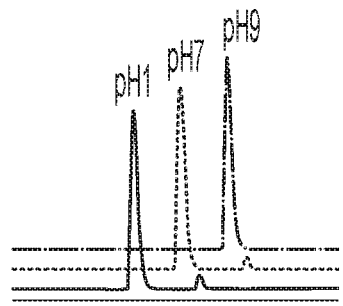
FIG. 5A-B shows that cholic acid-7-sulfate is stable in a wide range of pHs, and has no toxicity in intestinal Caco cells in vitro
Figure 5B:
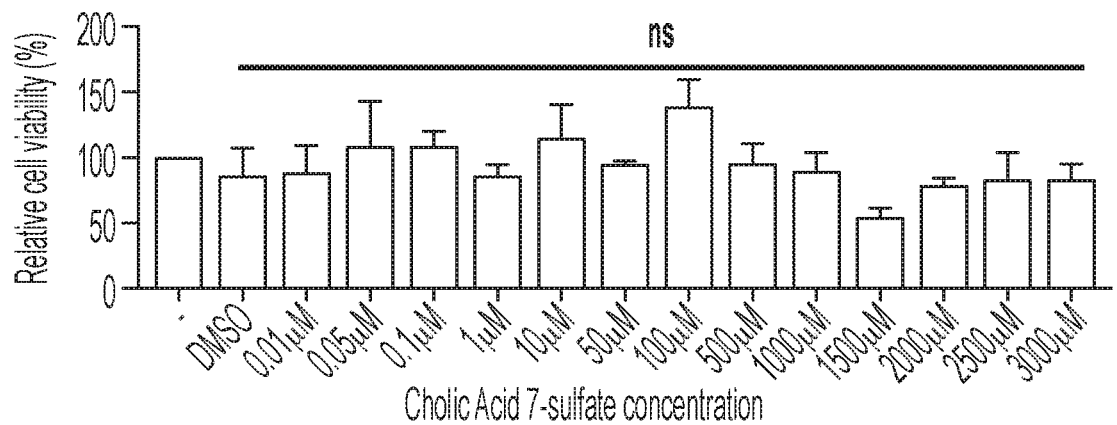
Figure 5C:
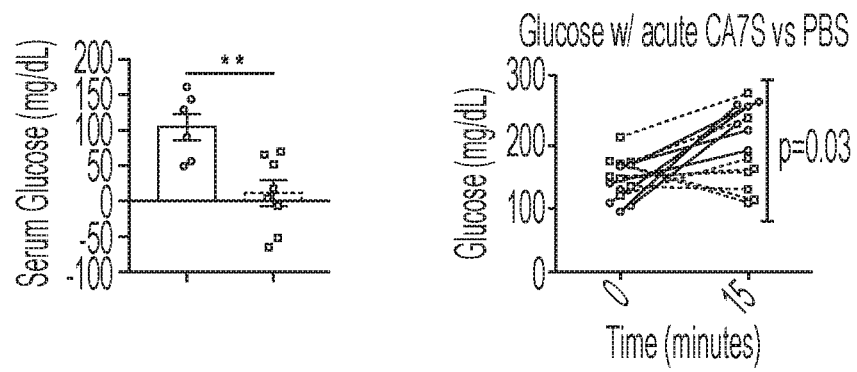
FIG. 5C-D shows that treatment of HFD-fed mice with cholic acid-7-sulfate in vivo reduced blood glucose levels and induced GLP-1 levels within 15 min. of treatment.
Figure 5D:
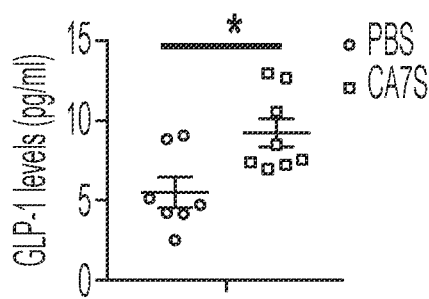
Figure 5E:
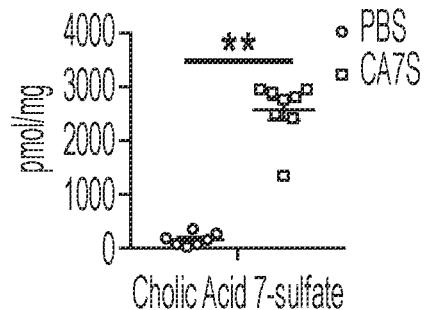
FIG. 5E shows that dosing with 1 mg cholic acid-7-sulfate resulted in ~2500 μM cholic acid-7-sulfate in the cecum, similar to the amounts we saw in sleeve-operated mice.
Figure 5F:
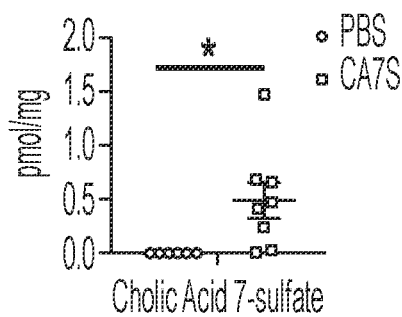
FIG. 5F-G shows that ectopic introduction of cholic acid-7-sulfate allowed only minor amounts to leak into systemic circulation and in the portal vein, and did not significantly affect other bile acids in the cecum, blood, or the portal vein.
Figure 5G:
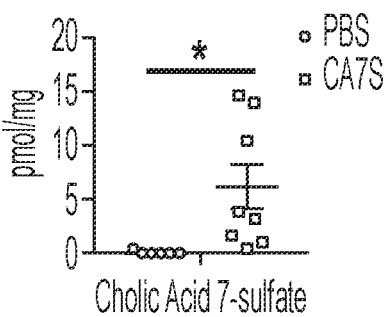
Figure 5H:
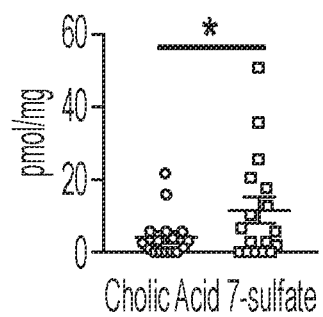
FIG. 5H shows that feces from human patients pre- and post-sleeve gastrectomy also have an increase in cholic acid-7-sulfate.

Cholic acid-7-sulfate is stable in a wide range of pHs, and has no toxicity in intestinal Caco cells in vitro (FIGS. 5A and 5B). Treatment of HFD-fed mice with cholic acid-7-sulfate in vivo reduced blood glucose levels and induced GLP-1 levels within 15 min. of treatment (FIGS. 5C and 5D). Therefore, acute cholic acid-7-sulfate treatment induces GLP-1 and reduces serum glucose levels in vivo. Dosing with 1 mg cholic acid-7-sulfate resulted in ~2500 µM cholic acid-7-sulfate in the cecum, similar to the amounts we saw in sleeve-operated mice (FIG. 5E). Ectopic introduction of cholic acid-7-sulfate allowed only minor amounts to leak into systemic circulation and in the portal vein, and did not significantly affect other bile acids in the cecum, blood, or the portal vein (FIGS. 5F and 5G, FIGS. 10, 11, and 12). Feces from human patients pre- and post-sleeve gastrectomy also have an increase in cholic acid-7-sulfate (FIG. 5H).

Figure 13:
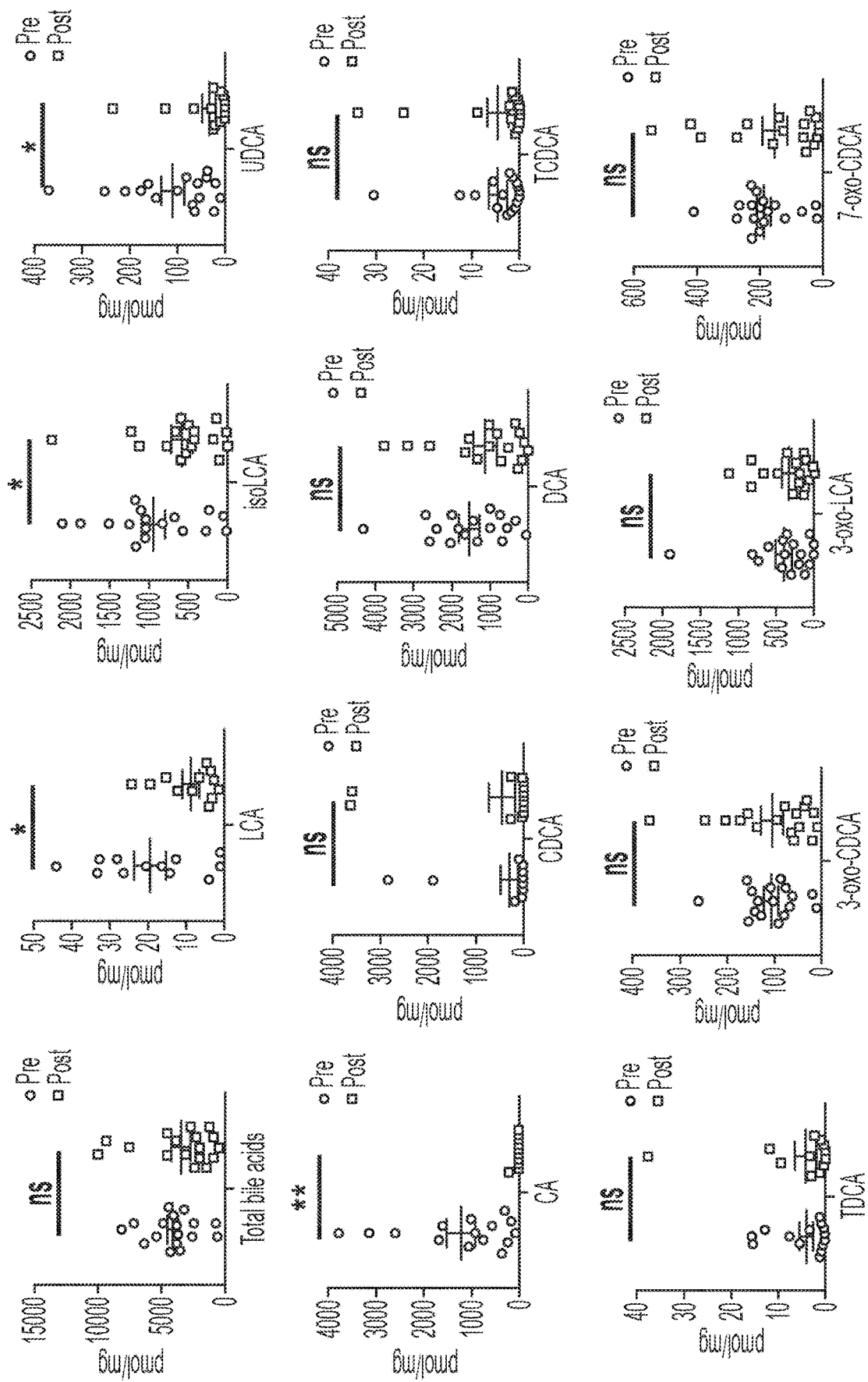
FIG. 13 shows that human fecal samples post-sleeve have a reduction in levels of secondary bile acids LCA, isolithocholic acid (iso-LCA), and ursodeoxy cholic acid (UDCA), similar to what we observed in mice post-sleeve. Other bile acids and total bile acids were not significantly affected, except for CA levels.

Human fecal samples post-sleeve have a reduction in levels of secondary bile acids LCA, iso-LCA, and UDCA, similar to what was observed in mice post-sleeve (FIG. 13). Other bile acids and total bile acids were not significantly affected, except for calcium levels. (FIG. 13).

Example 3. SULT2A Induction and Bile Acid Profile in Liver and Blood

Figure 14:
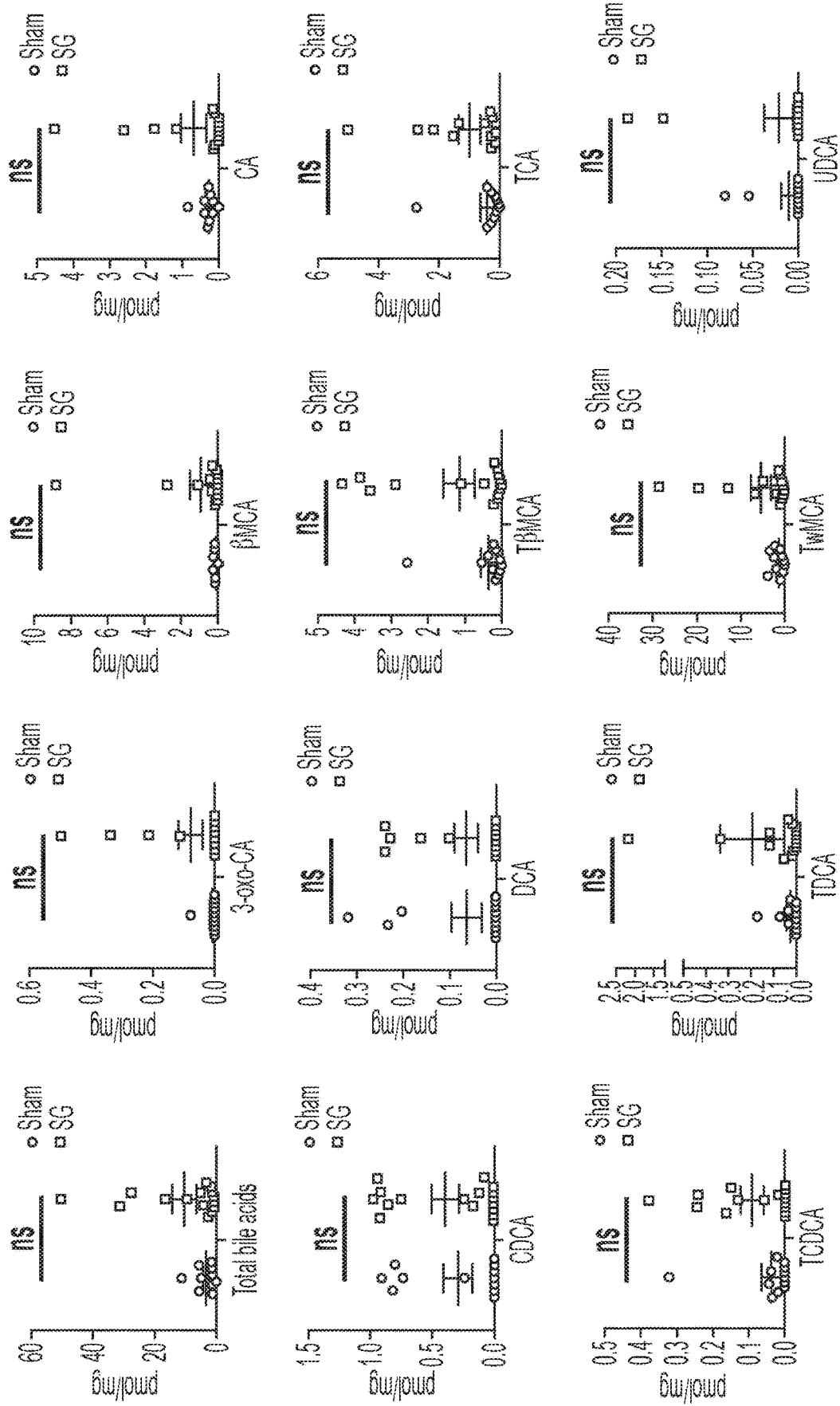
FIG. 14 shows that the portal vein had a very different repertoire of bile acids compared to circulating blood.

Sulfation is a detoxification method to excrete toxic bile acids. Bile acids have been shown to tightly regulate their own synthesis, conjugation, and sulfation. The liver is the major site for synthesis and sulfation of bile acids, therefore bile acids in the hepatic portal vein were analyzed to determine the origin of sulfated cholic acid and a mechanism for the increase in cholic acid-7-sulfate in sleeve mice. The hepatic portal vein is part of the enterohepatic circulation of bile acids. The liver receives 80% of its blood from the hepatic portal vein. The portal vein has a different repertoire of bile acids compared to circulating blood (FIG. 6B & FIG. 14).

Figure 6A:
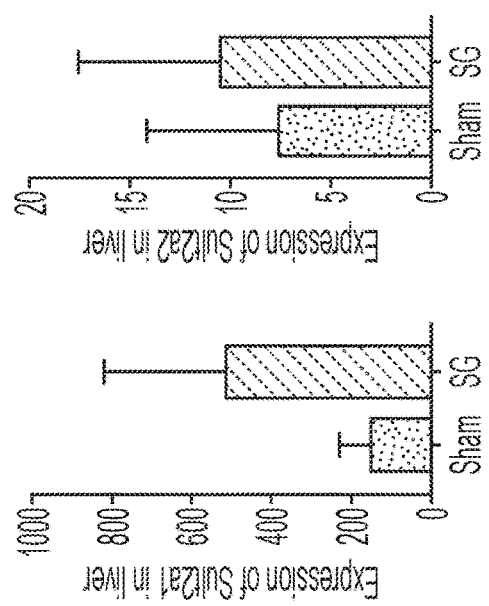
FIG. 6A shows that livers from mice exhibit an increase in SULT2A enzyme isoform 1, previously shown to sulfate bile acids.
Figure 6B:
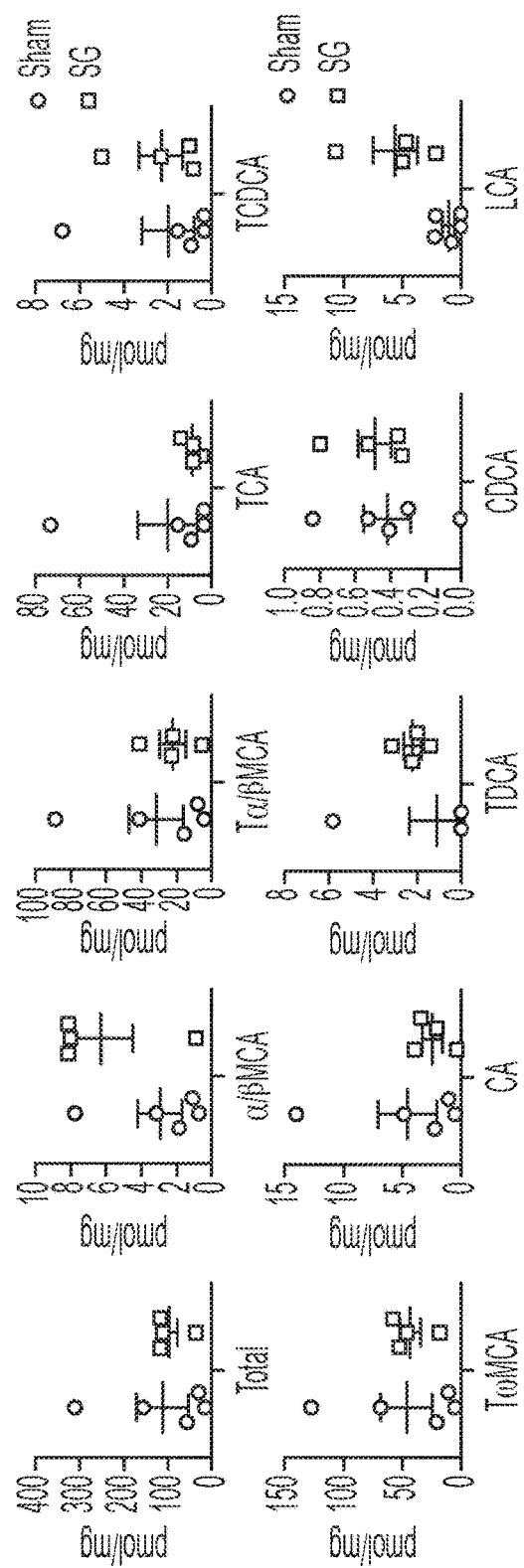
FIG. 6B shows that the portal vein has a different repertoire of bile acids compared to circulating blood.

Mice livers show an increase in SULT2A enzyme isoform 1, previously shown to sulfate bile acids (FIG. 6A).

Figure 6C:
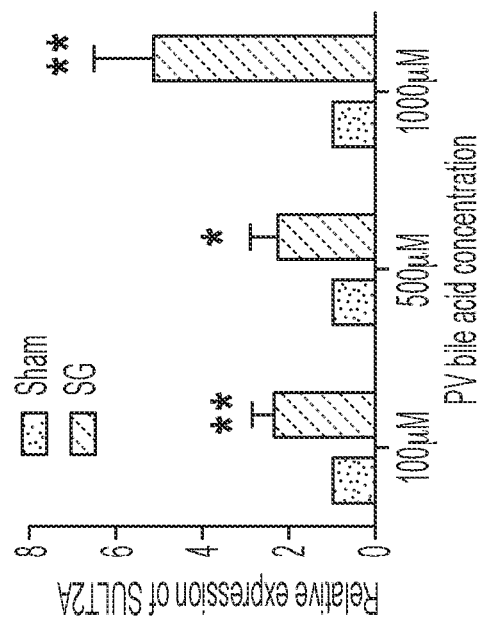
FIG. 6C shows that the bile acid pool in the portal vein of sleeve-operated mice significantly induced SULT2A1 compared to the portal vein bile acid pool in sham-operated mice.

To not be bound by a particular theory, it was hypothesized that bile acids in the hepatic portal vein signal in the liver to induce sulfation of cholic acid. Pools of bile acids were tested mimicking those observed in the sleeve- and sham-operated mouse portal veins in inducing SULT2A1 in vitro. Using HepG2 cells, it was observed that the bile acid pool in the portal vein of sleeve-operated mice significantly induced SULT2A1 compared to the portal vein bile acid pool in sham-operated mice (FIG. 6C).

Figure 6D:
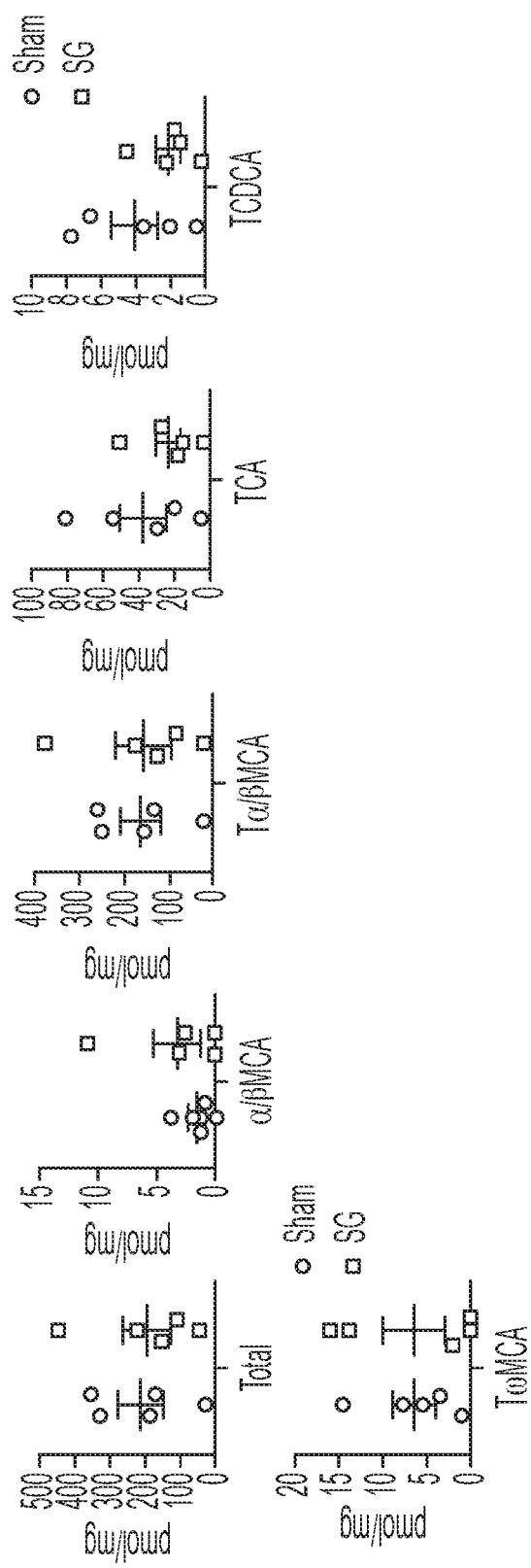

Bile acids are modified in the intestine by the microbiome. Therefore, the influence of the microbiome in inducing sulfation of bile acids in the liver was tested. Sleeve gastrectomy was performed and sham surgery on HFD-fed mice treated with antibiotics. Pools of bile acids mimicking those observed in the antibiotic-treated sleeve- and sham-operated mouse portal veins were tested inducing SULT2A1 in HepG2 cells. There was no difference in induction of SULT2A1 between the pools observed (FIGS. 6D and 6E).

Figure 15:
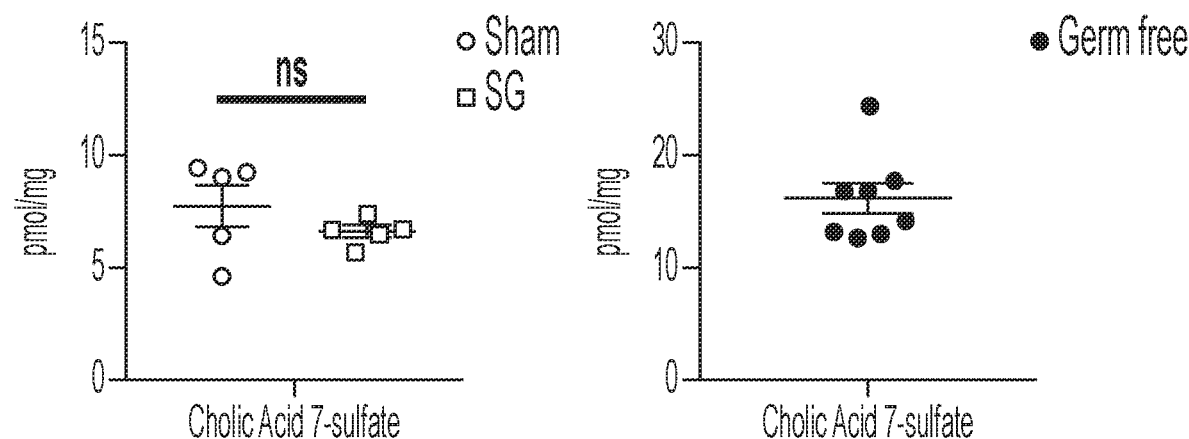
FIG. 15 shows that there is no cholic acid-7-sulfate in the liver and approximately 200-fold lower levels of cholic acid-7-sulfate in the cecum in antibiotic-treated mice compared to HFD-fed conventional mice.
Figure 16:
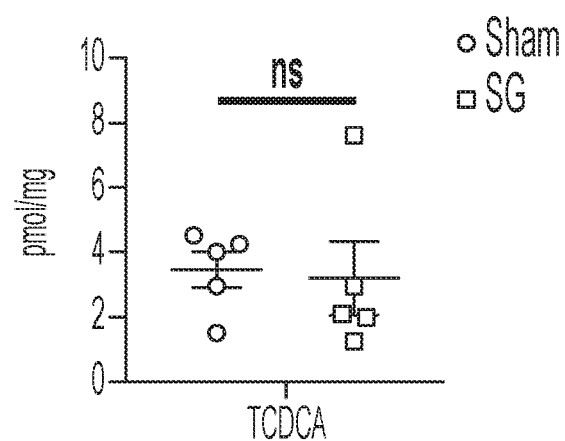
FIG. 16 shows TCDCA levels of sham and SG mice.

Consistently, it was observed that there was no cholic acid-7-sulfate in the liver and approximately 200-fold lower levels of cholic acid-7-sulfate in the cecum in antibiotic-treated mice (FIG. 14 and FIG. 15) compared to HFD-fed conventional mice. Also, there was no significant difference in cholic acid-7-sulfate levels between antibiotic-treated sleeve- and sham-operated mouse cecum (FIG. 9). This suggests that a microbiome is required for sulfation of cholic acid. In support of this hypothesis, germ-free animals fed a high fat diet also show 200-fold lower cholic acid-7-sulfate in their cecum (FIG. 9).

To test which bile acid(s) may be involved in inducing SULT2A1 enzyme, the bile acids in the portal vein that were significantly different between HFD-fed conventional mice and HFD-fed mice treated with antibiotics were analyzed. It was observed that LCA, TDCA, CA, and CDCA were absent in the antibiotic-treated mouse portal veins (FIG. 6D).

Amongst these, LCA induced SULT2A1 in HepG2, while others did not in all concentrations tested (FIG. 6F). LCA levels were also increased in sleeve mice compared to sham-operated, while the total bile acid levels did not differ significantly, suggesting that LCA is an inducer of SULT2A1 expression (FIG. 6B). To identify the receptor involved in LCA-mediated induction of SULT2A1 in liver cells, siRNA of known receptors was performed. The PXR receptor was consistently upregulated in mice post-sleeve in the liver (FIGS. 6G and 6H).

Example 4. Identification of Cholic Acid-7-Sulfate

Figure 17A:
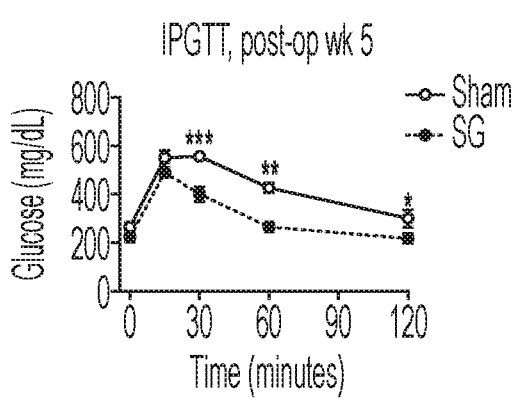
FIG. 17 shows cholic acid-7-sulfate (CA7S), a bile acid metabolite increased in mice and humans following sleeve gastrectomy, is a TGR5 agonist and induces GLP-1 secretion in vitro.
Figure 17B:
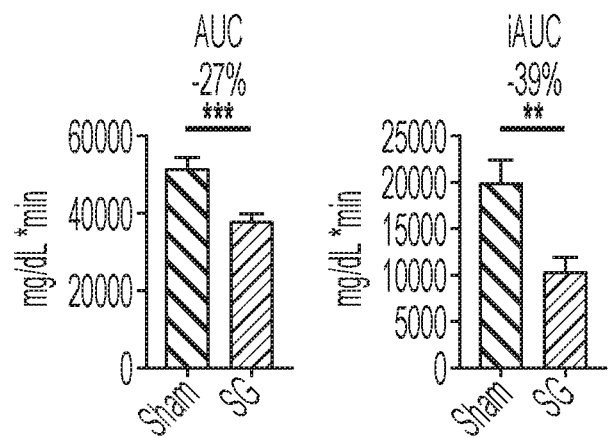
Figure 17C:
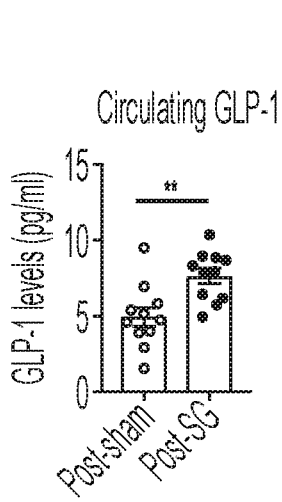
Figure 17D:
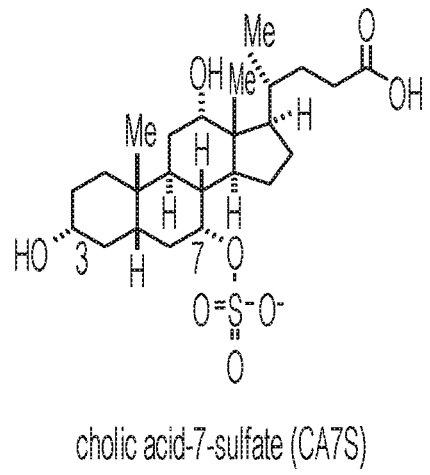
Figure 17E:
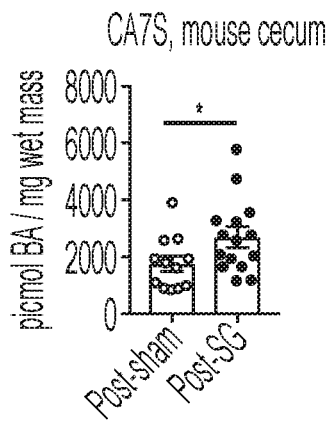
Figure 17F:
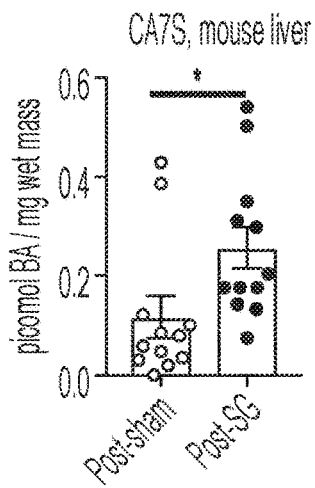
Figure 17G:
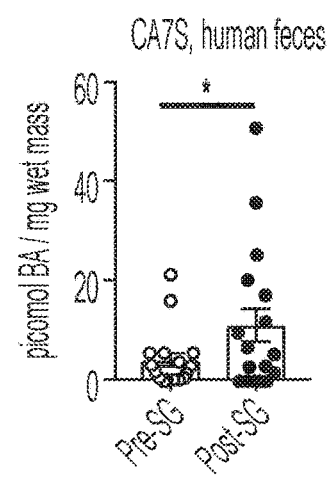

The individual bile acids in cecal contents of post-gastric sleeve (SG) and sham mice were quantified using UPLC-MS. A significant increase in a monosulfated, trihydroxy BA in cecal contents of SG mice was observed. Using NMR spectroscopy, the compound was identified as cholic acid-7-sulfate (CA7S) (FIGS. 17D and 17E). This molecule is a sulfated metabolite of cholic acid (CA), which is an abundant primary BA in both mice and humans. Sulfation of BAs predominantly occurs in the liver (Alnouti, Y. Toxicol. Sci. 2009, 108, 225-246). Increased levels of CA7S in the liver of SG mice were also found (FIG. 17F). CA7S was the only BA detected whose levels were significantly higher in SG mouse livers and cecal contents.

Bile acids in stool from human patients who had undergone SG were quantified. Fecal CA7S levels were also significantly increased in patients post-SG compared to their pre-surgery levels (FIG. 1G).

Example 5. CA7S Activation of Human TG R5 in HEK293T Cells

Figure 17H:
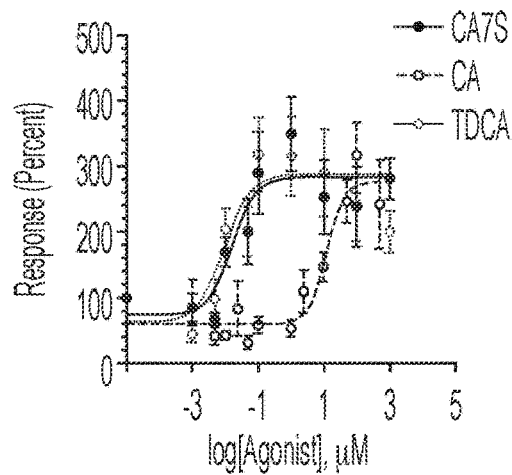

The activation of human TGR5 was examined in human embryonic kidney cells (HEK293T) by CA7S, CA, or tauro-deoxycholic acid (TDCA) which is a naturally occurring BA and potent TGR5 agonist (Brighton, C. A. et al. Endocrinology 2015 156, 3961-3970). It was found that CA7S activated human TGR5 in a dose-dependent manner and to a similar extent as TDCA. CA7S also displayed a lower $EC_{50}$ (0.17 µM) than CA (12.22 µM) (FIG. 17H).

Figure 17I:
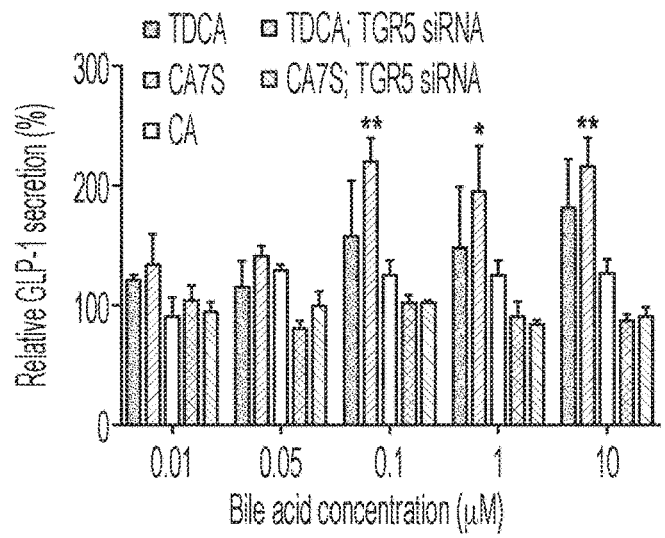

CA7S induced GLP-1 secretion in human intestinal L-cells (NCI-H716) to a similar degree as TDCA in a dose-dependent manner, while CA had no effect on GLP-1 secretion (FIGS. 17I and 21A). CA7S extracted directly from cecal contents of SG mice also induced GLP-1 secretion in vitro (FIG. 21B). Furthermore, siRNA-mediated knockdown of TGR5 abolished both CA7S and TDCA-mediated secretion of GLP-1 (FIGS. 17I, 21A, and 21C). This result indicates that induction of GLP-1 secretion by CA7S requires TGR5. TGR5 agonism also results in elevated intracellular calcium levels (Kuhre, R. E. et al. Journal of Molecular Endocrinology 2016, 56, 201-211). Consistent with this previous finding, we observed a dose-dependent increase in calcium levels in NCI-H716 cells treated with CA7S (FIG. 21D). Taken together, these results demonstrate that CA7S, a naturally occurring BA metabolite, is a potent TGR5 agonist and GLP-1 secretagogue.

Example 6. Evaluation of Acute Anti-Diabetic Effects In Vivo

Figures 18A, 18B:
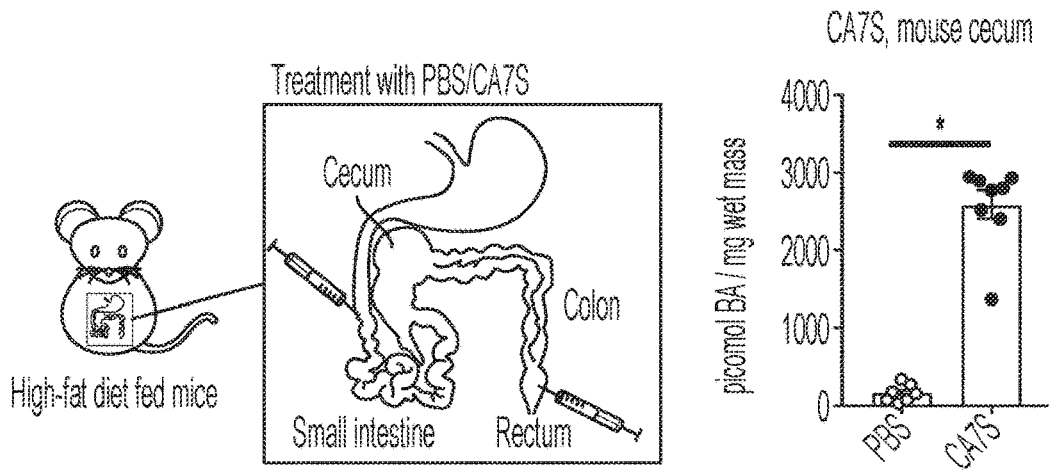
FIG. 18 shows acute CA7S administration induces GLP-1 and reduces serum glucose levels in vivo.

DIO mice were treated with either CA7S or PBS via duodenal and rectal catheters (FIG. 18A). Administration of 1 mg of CA7S resulted in an average of 2500 pmol/mg wet mass of CA7S in cecal contents, a concentration similar to observed post-SG levels (FIG. 17E, 18B, Table 1).

TABLE 1

Cholic acid-7-sulfate concentration in indicated tissues and blood

| Treatment | Tissue/blood | CA7S concentration (mean ± SEM) |
| --- | --- | --- |
| DIO mice; sham surgery | Cecum | 1726 ± 267 pmol/mg |
|  | Liver | 0.12 ± 0.04 pmol/mg |
|  | Portal vein | n.d. |
|  | Systemic blood | n.d. |
| DIO mice; sleeve gastrectomy | Cecum | 2661 ± 331 pmol/mg |
|  | Liver | 0.27 ± 0.04 pmol/mg |
|  | Portal vein | n.d. |
|  | Systemic blood | n.d. |
| DIO mice; enteral PBS | Cecum | 161.1 ± 46.4 pmol/mg |
|  | Portal vein | 0.07 ± 0.06 pmol/mg |
|  | Systemic blood | n.d. |
| DIO mice; enteral CA7S | Cecum | 2577 ± 185 pmol/mg |
|  | Portal vein | 6.13 ± 2.11 pmol/mg |
|  | Systemic blood | 0.5 ± 0.2 pmol/µl |
| DIO mice; PBS gavage | Cecum | 947 ± 349 pmol/mg |
|  | Portal vein | n.d. |
|  | Systemic blood | n.d. |
| DIO mice; CA7S gavage | Cecum | 14345 ± 1451 pmol/µl |
|  | Portal vein | 13.2 ± 7.7 pmol/µl |
|  | Systemic blood | n.d. | n.d. not detected, all data are presented as mean ± SEM.

Figures 18C, 18D:
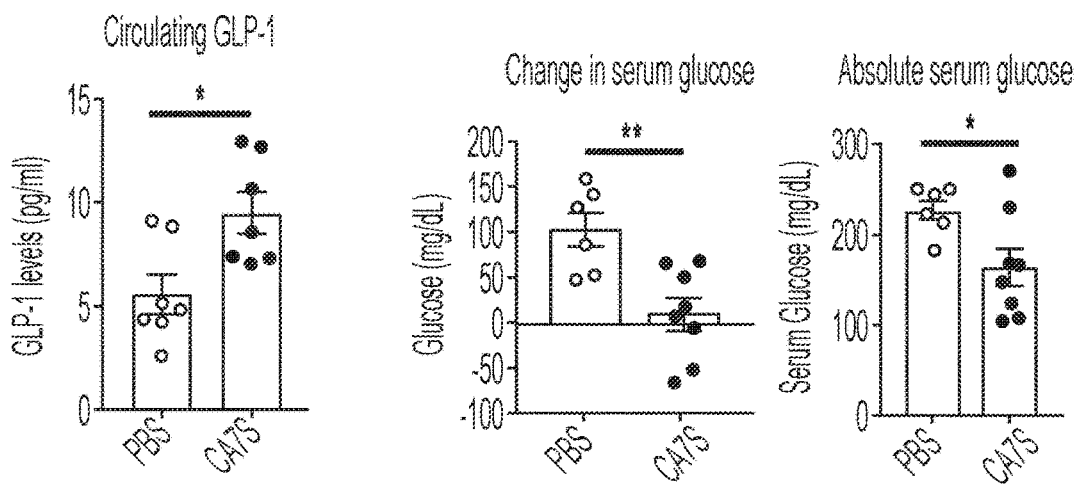
Figures 18E, 18F:
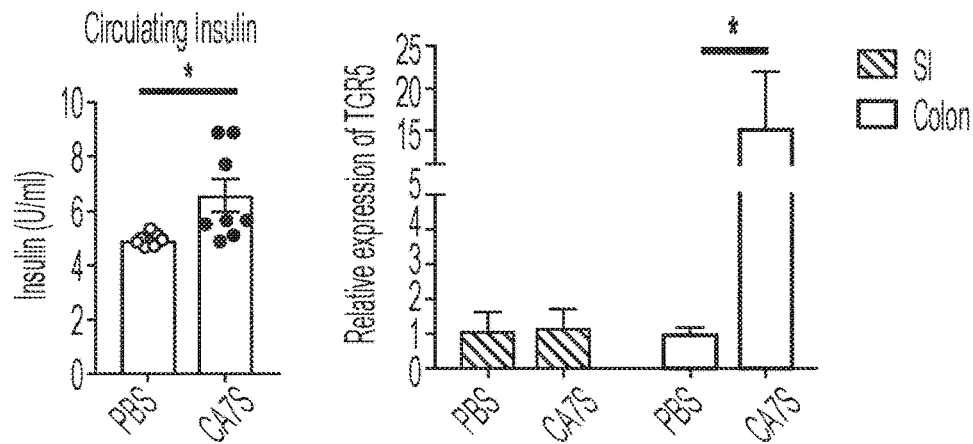

CA7S-treated mice displayed increased systemic GLP-1 levels compared to PBS-treated mice within 15 minutes (FIG. 18C). Moreover, CA7S-treated mice exhibited reduced blood glucose levels and increased insulin levels compared to PBS-treated mice (FIGS. 18D, 18E, and 21E). GLP-1-producing enteroendocrine L-cells are enriched in the distal compared to the proximal gut (Eissele, R. et al. Eur. J. Clin. Invest. 1992 22, 283-291; Harach, T. et al. Sci Rep 2012, 2, 430). It was observed that TGR5 expression was increased in the colon, but not the terminal ileum, of CA7S-treated mice (FIG. 18F). Without wishing to be bound by any particular theory, these results may suggest that in an acute setting, distal action of CA7S in the GI tract induces systemic glucose clearance and thus ameliorates hyperglycemia.

Example 7. Antidiabetic Effects of CA7S Over Prolonged Periods

Figure 19A:
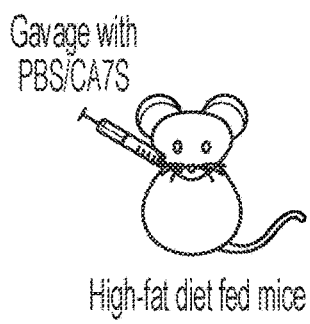
FIG. 19 shows CA7S gavage induces GLP-1 and improves glucose tolerance in vivo via GLP1 receptor.
Figure 19B:
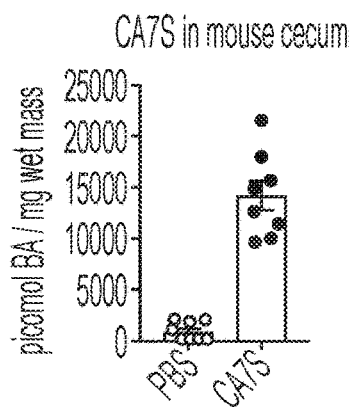
Figure 19C:
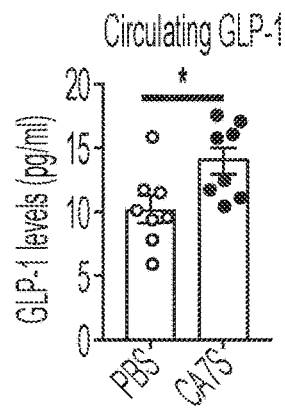

DIO mice were orally gavaged with CA7S at a dose of 100 mg/kg (FIG. 19A). Analysis of cecal contents 5 hours post-gavage showed an accumulation of 15,000 picomol/mg wet mass of CA7S (mean value, FIG. 19B), a concentration that is within an order of magnitude of the mean amount measured in post-SG mice. These data indicate that we had administered a physiologically relevant concentration of this metabolite. Systemic levels of GLP-1 were increased in CA7S-gavaged mice compared to PBS-treated mice 5 hours post-treatment (FIG. 19C). This result is consistent with the findings from enteral administration and demonstrates that oral CA7S treatment can increase circulating GLP-1 for several hours.

Figure 19D:
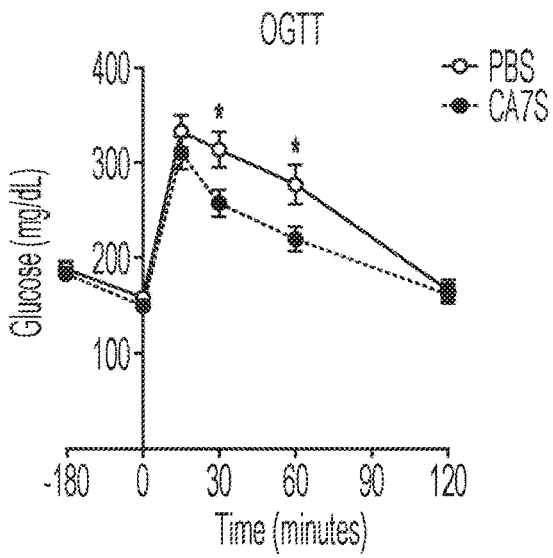
Figure 19E:
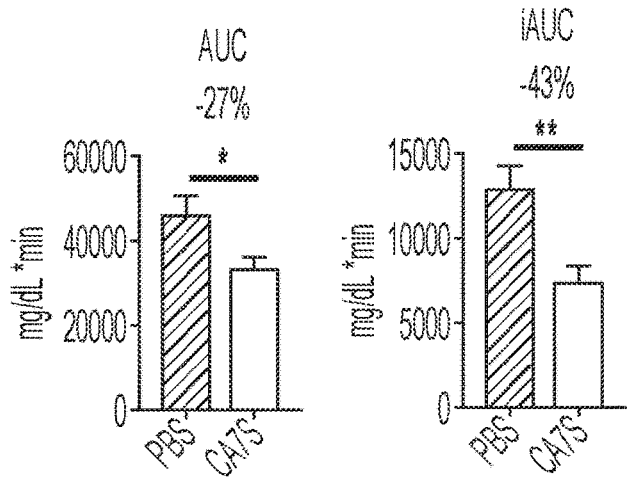

The effect of CA7S on glucose tolerance over time was also determined using an oral glucose tolerance test (OGTT). DIO mice were gavaged with CA7S (100 mg/kg) or PBS and then administered an oral glucose bolus 3 hours later. CA7S treatment resulted in an increased rate of blood glucose clearance (FIG. 19D). Moreover, the total and incremental areas under the glucose versus time curves (AUC and iAUC) were significantly decreased in CA7S-compared to vehicle-treated mice (FIG. 19E).

Example 8. Dependency of Anti-Diabetic Effects of CA7S on GLP-1

Figure 19F:
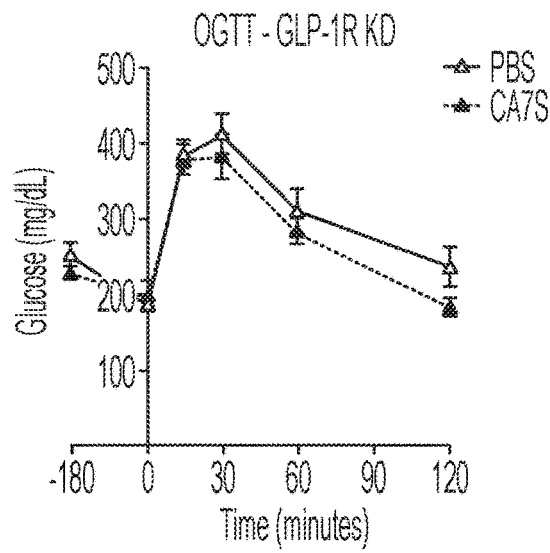
Figure 19G:
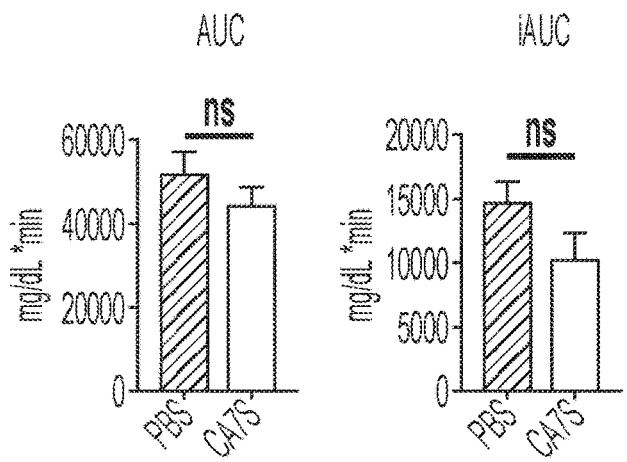
Figure 19H:
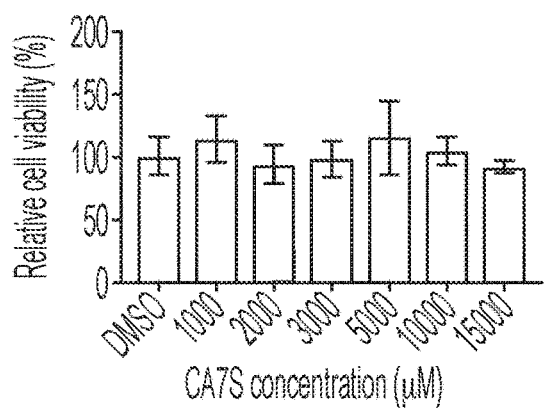
Figure 19I:
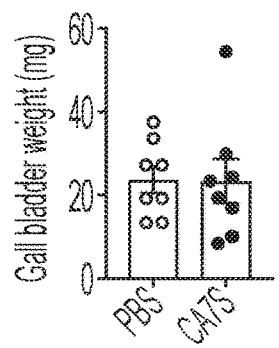
Figure 22:
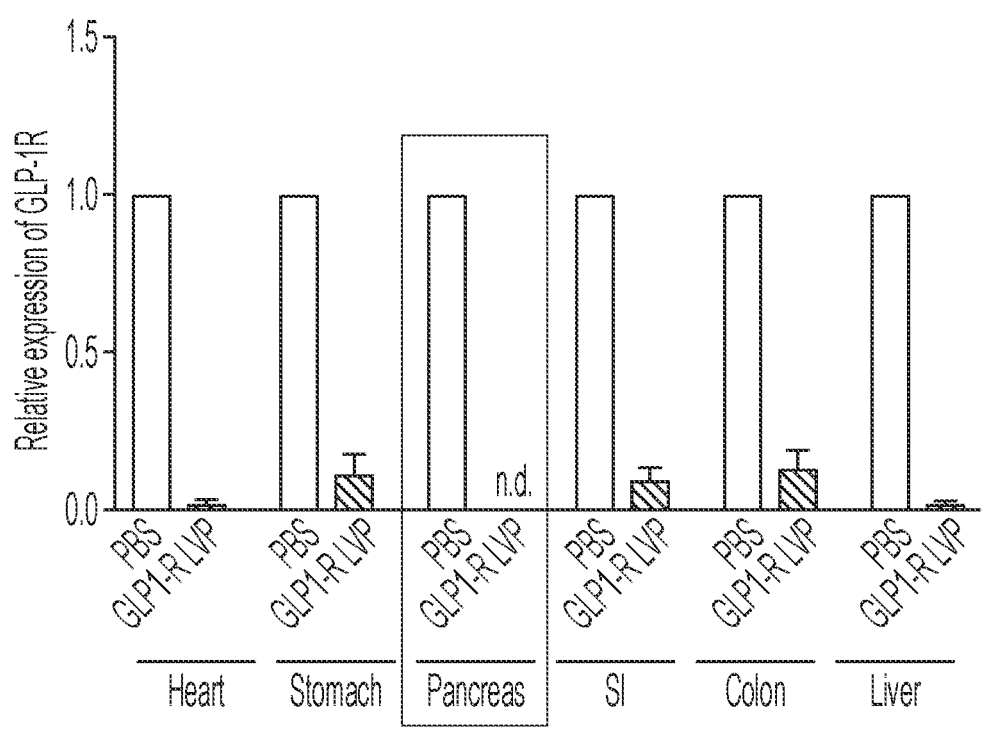
FIG. 22 shows GLP-1R shRNA knockdown efficiency and stability of CA7S.

Lentiviral shRNA-mediated knockdown of GLP-1R was carried out in vivo. DIO mice were injected intraperitoneally with $5\times10^5$ shRNA lentiviral particles targeting GLP-1R. At day 3 post-injection, expression of GLP-1R in the intestines, heart, liver, and stomach was significantly reduced, and importantly, the expression of GLP-1R was undetectable in the pancreas (FIG. 22A). Mice were then gavaged with CA7S (100 mg/kg) or PBS and subjected to an OGTT 3 hours post-gavage. There were no significant differences in the glycemic curves or AUCs between CA7S-treated and PBS-treated mice in the absence of GLP-1R, suggesting that in an acute setting, the blood glucose clearing-effects of CA7S are largely dependent on GLP-1 (FIGS. 19F and 19G).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating diabetes, the method comprising: administering to a subject in need thereof an agent that increases the level of cholic acid-7-sulfate in the subject, wherein the agent is cholic acid-7-sulfate, or a pharmaceutically acceptable salt thereof.

2. The method of claim 1, wherein the agent induces GLP-1 secretion from a target cell.

3. The method of claim 1, wherein the agent is formulated in a pharmaceutical composition.

4. The method of claim 3, wherein the pharmaceutical composition is formulated to restrict delivery of the agent to the gastrointestinal tract of the subject.

5. The method of claim 1, wherein the diabetes is type I, type II, neonatal, or maturity onset diabetes in the young.

6. The method of claim 1, wherein the step of administering reduces glucose levels in the serum of a subject.

7. The method of claim 1, wherein the subject is a mammal.

8. The method of claim 7, wherein the mammal is a human.

9. The method of claim 2, wherein the target cell is an enteroendocrine cell, an epithelial cell, an L-cell, or a neuron.

10. The method of claim 1 further comprising administering to the subject in need thereof an additional pharmaceutical agent.

11. The method of claim 1 further comprising administering to the subject in need thereof an anti-diabetic agent.

12. The method claim 1 further comprising administering to the subject in need thereof an anti-diabetic agent selected from the group consisting of insulin, insulin analogs, nateglinide, repaglinide, metformin, thiazolinediones, glitazones, glisoxepid, glyburide, glibenclamide, acetohexamide, chloropropamide, glibornuride, tolbutamide, tolazamide, glipizide, carbutamide, gliquidone, glyhexamide, phenbutamide, tolcyclamide, glimepiride, and gliclazide.

13. The method of claim 1 further comprising administering to the subject in need thereof a dipeptidyl peptidase 4 (DPP-4) inhibitor.

14. The method of claim 1 further comprising administering to the subject in need thereof a DPP-4 inhibitor selected from the group consisting of sitagliptin, linagliptin, alogliptin, saxagliptin, and vildagliptin.

15. The method of claim 12, wherein the glitazone is troglitazone, pioglitazone, or rosiglitazone.

16. The method of claim 1, wherein the agent increases the activity of TGR5.

17. The method of claim 16, wherein the activity of TGR5 is increased by at least 50% as compared to a control.

18. The method of claim 2, wherein the secretion of GLP1 is increased by at least 50% as compared to a control.

19. The method of claim 5, wherein the diabetes is type II diabetes.

20. The method of claim 1, wherein the agent is administered orally.

\* \* \* \* \*

```
                        SEQUENCE LISTING

<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 1
cggaattcgc acttggtcct tgtgctct                                          28

<210> SEQ ID NO 2
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 2
gtctcgagtt agttcaagtc caggtcga                                          28

<210> SEQ ID NO 3
<211> LENGTH: 20
<212> TYPE: DNA
<213> ORGANISM: Homo sapiens

<400> SEQUENCE: 3
cctaggaagt gccagtgcag                                                   20

<210> SEQ ID NO 4
<211> LENGTH: 20
<212> TYPE: DNA
<213> ORGANISM: Homo sapiens

<400> SEQUENCE: 4
cttgggtggt aggcaatgct                                                   20

<210> SEQ ID NO 5
<211> LENGTH: 20
<212> TYPE: DNA
<213> ORGANISM: Homo sapiens

<400> SEQUENCE: 5
cctggcgtcg tgattagtga                                                   20

<210> SEQ ID NO 6
<211> LENGTH: 20
<212> TYPE: DNA
<213> ORGANISM: Homo sapiens
```

```
<400> SEQUENCE: 6
cgagcaagac gttcagtcct                                               20

<210> SEQ ID NO 7
<211> LENGTH: 20
<212> TYPE: DNA
<213> ORGANISM: Mus musculus

<400> SEQUENCE: 7
agggcttgat ggtggctatc                                               20

<210> SEQ ID NO 8
<211> LENGTH: 20
<212> TYPE: DNA
<213> ORGANISM: Mus musculus

<400> SEQUENCE: 8
ggacacttga ggggcttcat                                               20

<210> SEQ ID NO 9
<211> LENGTH: 20
<212> TYPE: DNA
<213> ORGANISM: Mus musculus

<400> SEQUENCE: 9
attggagctg gaattaccgc                                               20

<210> SEQ ID NO 10
<211> LENGTH: 20
<212> TYPE: DNA
<213> ORGANISM: Mus musculus

<400> SEQUENCE: 10
cggctaccac atccaaggaa                                               20
```